United States Patent
Yamazaki et al.

(10) Patent No.: US 9,766,541 B2
(45) Date of Patent: Sep. 19, 2017

(54) POSITIVE-TYPE RESIST COMPOSITION, METHOD FOR FORMING RESIST PATTERN, PHOTO-REACTIVE QUENCHER, AND POLYMERIC COMPOUND

(71) Applicant: TOKYO OHKA KOGYO CO., LTD., Kawasaki-shi (JP)

(72) Inventors: Hiroto Yamazaki, Kawasaki (JP); Yoshitaka Komuro, Kawasaki (JP); Masatoshi Arai, Kawasaki (JP); Daisuke Kawana, Kawasaki (JP); Kenta Suzuki, Kawasaki (JP); Tatsuya Fujii, Kawasaki (JP)

(73) Assignee: TOKYO OHKA KOGYO CO., LTD., Kawasaki-Shi (JP)

(*) Notice: Subject to any disclaimer, the term of this patent is extended or adjusted under 35 U.S.C. 154(b) by 0 days.

(21) Appl. No.: 15/186,044

(22) Filed: Jun. 17, 2016

(65) Prior Publication Data

US 2016/0376233 A1 Dec. 29, 2016

(30) Foreign Application Priority Data

Jun. 26, 2015 (JP) .................. 2015-129169

(51) Int. Cl.

| | | |
|---|---|---|
| G03F 7/004 | (2006.01) | |
| G03F 7/039 | (2006.01) | |
| G03F 7/20 | (2006.01) | |
| G03F 7/32 | (2006.01) | |
| C08F 216/10 | (2006.01) | |
| G03F 7/038 | (2006.01) | |
| H01L 21/027 | (2006.01) | |
| C07C 65/10 | (2006.01) | |
| C07C 309/06 | (2006.01) | |
| C07C 309/12 | (2006.01) | |
| C07C 309/19 | (2006.01) | |
| C07C 381/12 | (2006.01) | |

(52) U.S. Cl.
CPC .......... *G03F 7/0045* (2013.01); *C07C 65/10* (2013.01); *C07C 309/06* (2013.01); *C07C 309/12* (2013.01); *C07C 309/19* (2013.01); *C07C 381/12* (2013.01); *C08F 216/10* (2013.01); *G03F 7/004* (2013.01); *G03F 7/0046* (2013.01); *G03F 7/038* (2013.01); *G03F 7/039* (2013.01); *G03F 7/0397* (2013.01); *G03F 7/2059* (2013.01); *G03F 7/322* (2013.01); *H01L 21/0274* (2013.01); *C07C 2602/42* (2017.05); *C07C 2603/74* (2017.05)

(58) Field of Classification Search
CPC ...... G03F 7/004; G03F 7/0045; G03F 7/0046; G03F 7/038; G03F 7/0397; H01L 21/0271; C07C 309/65; C07C 381/12

USPC ............... 430/270.1, 913; 526/243; 560/117
See application file for complete search history.

(56) References Cited

U.S. PATENT DOCUMENTS

| | | | | |
|---|---|---|---|---|
| 7,442,485 | B2 * | 10/2008 | Oshima | ................ B41C 1/1008 |
| | | | | 101/467 |
| 7,642,368 | B2 * | 1/2010 | Sumino | ................ C07C 381/12 |
| | | | | 558/412 |
| 8,507,575 | B2 * | 8/2013 | Matsumura | .......... G03F 7/0045 |
| | | | | 520/1 |
| 8,609,317 | B2 * | 12/2013 | Ichikawa | ................ C07C 62/22 |
| | | | | 430/270.1 |
| 8,815,490 | B2 * | 8/2014 | Matsuda | ................. C08F 20/26 |
| | | | | 430/270.1 |
| 9,045,398 | B2 * | 6/2015 | Suzuki | ................. C07C 309/06 |
| 9,244,347 | B2 * | 1/2016 | Komuro | ............... C07C 381/12 |
| 9,316,915 | B2 * | 4/2016 | Hatakeyama | ......... G03F 7/2037 |
| 2005/0064329 | A1 | 3/2005 | Takahashi | |
| 2011/0014567 | A1 * | 1/2011 | Ichikawa | ............... C07C 62/22 |
| | | | | 430/270.1 |

(Continued)

FOREIGN PATENT DOCUMENTS

| | | |
|---|---|---|
| JP | A-2011-253017 | 12/2001 |
| JP | A-2005-091976 | 4/2005 |

*Primary Examiner* — Amanda C Walke
(74) *Attorney, Agent, or Firm* — Knobbe Martens Olson & Bear LLP

(57) ABSTRACT

A positive-type resist composition which generates an acid upon exposure and whose solubility in an alkali developing solution increases under the action of an acid, the composition including a base material component whose solubility in an alkali developing solution increases under the action of an acid; and a compound represented by the following general formula (m0):

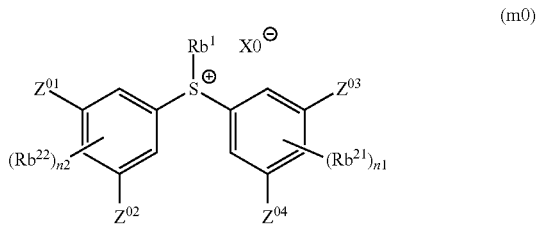

(m0)

$Z^{01}$ to $Z^{04}$ each independently represent a substituent having electron withdrawing properties, $Rb^{21}$ and $Rb^{22}$ each independently represent an alkyl group, an alicyclic hydrocarbon group which may have a substituent, or a hydroxyl group, $Rb^{1}$ represents an aryl group which may have a substituent, an alkyl group, or an alkenyl group, n1 and n2 represent an integer of 0 to 3, and $X0^{-}$ represents an organic anion.

16 Claims, No Drawings

(56) References Cited

U.S. PATENT DOCUMENTS

| | | | |
|---|---|---|---|
| 2011/0293900 A1 | 12/2011 | Tomeba et al. | |
| 2012/0237876 A1* | 9/2012 | Maruyama | C08F 12/20 430/285.1 |
| 2013/0177852 A1* | 7/2013 | Yoon | G03F 7/031 430/285.1 |

* cited by examiner

POSITIVE-TYPE RESIST COMPOSITION, METHOD FOR FORMING RESIST PATTERN, PHOTO-REACTIVE QUENCHER, AND POLYMERIC COMPOUND

CROSS-REFERENCE TO RELATED APPLICATIONS

Priority is claimed on Japanese Patent Application No. 2015-129169, filed Jun. 26, 2015, the content of which is incorporated herein by reference.

BACKGROUND OF THE INVENTION

Field of the Invention

The present invention relates to a positive-type resist composition, a method for forming a resist pattern, a photo-reactive quencher, and a polymeric compound.

Background Art

In lithography techniques, for example, a resist film composed of a resist material is formed on a substrate, and the resist film is subjected to selective exposure of radial rays such as light or electron beams through a mask having a predetermined pattern, followed by development, thereby forming a resist pattern having a predetermined shape with respect to the resist film.

A resist material in which the exposed areas become soluble in a developing solution is called a positive-type, and a resist material in which the exposed areas become insoluble in a developing solution is called a negative-type.

In recent years, in the production of semiconductor elements and liquid crystal display elements, advances in lithography techniques have led to rapid progress in the field of pattern miniaturization.

As a resist material which can be formed into a pattern of a minute dimension, conventionally, a chemically amplified resist composition is used, which includes a base material component whose solubility in a developing solution changes under the action of an acid and an acid generator component which generates an acid upon exposure. When a resist film formed by using the resist composition is selectively exposed at the time of forming a resist pattern, in the exposed areas, an acid is generated from the acid generator component. In the case where a resist material in which the exposed areas become soluble in a developing solution is used, a positive-type resist pattern whose solubility in a developing solution is changed by the change of a polarity of the exposed areas under the action of the acid is formed.

For the resist pattern of the minute dimension, various lithography properties such as reduced line width roughness (LWR), satisfactory sensitivity, and satisfactory resolution are required. In order to obtain the satisfactory lithography properties, the acid generator component were reviewed in various ways.

For example, Japanese Unexamined Patent Application, Publication No. 2011-253017 discloses a resist composition which can reduce LWR and a probe defect by adopting an acid generator component including a fluorine atom in a predetermined amount.

In addition, Japanese Unexamined Patent Application, Publication No. 2005-91976 discloses a resist composition which can improve the lithography properties such as line edge roughness by adopting an acid generator component having a triphenylsulfonium structure including a fluorine atom in a predetermined amount.

SUMMARY OF THE INVENTION

Henceforth, as the lithography techniques become further advanced and the resist pattern becomes gradually smaller, improvement in various lithography properties of the resist material is required.

In the case where the acid generator in the related art disclosed in Japanese Unexamined Patent Application, Publication No. 2011-253017 and Japanese Unexamined Patent Application, Publication No. 2005-91976 is used, there is still room for improvement in the various lithography properties.

The present invention has been made taking the aforementioned circumstances into consideration, and an object thereof is to provide a resist composition which can form a resist pattern having excellent lithography properties, and a method for forming a resist pattern using the resist composition.

According to a first aspect of the present invention, there is provided a positive-type resist composition which generates an acid upon exposure and whose solubility in an alkali developing solution increases under the action of an acid, the composition including: a base material component (A) whose solubility in an alkali developing solution increases under the action of an acid; and a compound (m) represented by the following general formula (m0).

[Chemical formula 1]

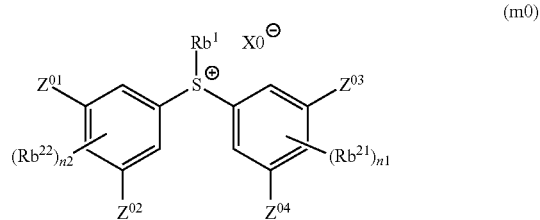

(m0)

In general formula (m0), $Z^{01}$ to $Z^{04}$ each independently represent a substituent having electron withdrawing properties, $Rb^{21}$ and $Rb^{22}$ each independently represent an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^1$ represents an aryl group which may have a substituent, an alkyl group which may have a substituent, or an alkenyl group which may have a substituent, n1 and n2 each independently represent an integer of 0 to 3, and $X0^-$ represents an organic anion.

According to a second aspect of the present invention, there is provided a positive-type resist composition which generates an acid upon exposure and whose solubility in an alkali developing solution increases under the action of an acid, the composition including: a base material component (A) whose solubility in an alkali developing solution increases under the action of an acid and which includes a resin component (A2) including a polymeric compound having a structural unit (a6) derived from a compound represented by the following general formula (a6-1).

[Chemical formula 2]

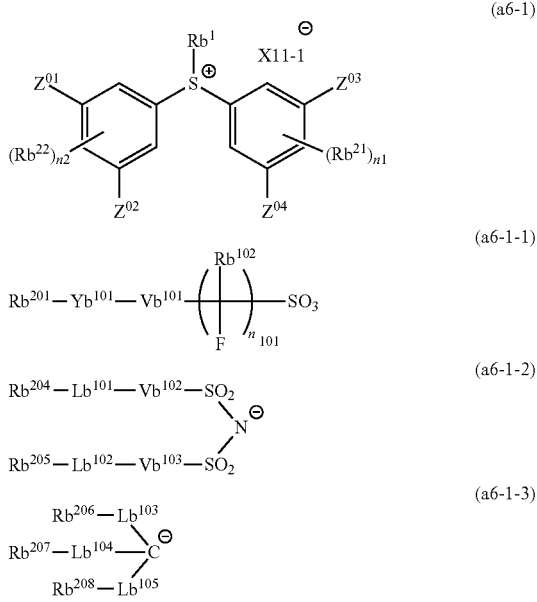

In general formula (a6-1), $Z^{01}$ to $Z^{04}$ each independently represent a substituent having electron withdrawing properties, $Rb^{21}$ and $Rb^{22}$ each independently represent an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^{1}$ represents an aryl group which may have a substituent, an alkyl group which may have a substituent, or an alkenyl group which may have a substituent, and n1 and n2 each independently represent an integer of 0 to 3.

X11-1⁻ represents an organic anion represented by any one of general formulae (a6-1-1) to (a6-1-3). In general formulae (a6-1-1) to (a6-1-3), $Rb^{201}$ represents a chain-like alkenyl group which may have a substituent, $Rb^{204}$ represents a cyclic group which may have a substituent, a chain-like alkyl group which may have a substituent, or a chain-like alkenyl group which may have a substituent, and $Rb^{205}$ represents a chain-like alkenyl group which may have a substituent.

$Rb^{206}$ to $Rb^{208}$ each independently represent a cyclic group which may have a substituent, a chain-like alkyl group which may have a substituent, or a chain-like alkenyl group which may have a substituent, with the proviso that at least one of $Rb^{206}$ to $Rb^{208}$ represents a chain-like alkenyl group which may have a substituent.

$Rb^{102}$ represents a fluorine atom or a fluorinated alkyl group having 1 to 5 carbon atoms. $Yb^{101}$ represents a single bond, or a divalent linking group including an oxygen atom. $Vb^{101}$ to $Vb^{103}$ each independently represent a single bond, an alkylene group, a fluorinated alkylene group, an arylene group, or a fluorinated arylene group. $Lb^{101}$ and $Lb^{102}$ each independently represent a single bond, or an oxygen atom. $Lb^{103}$ to $Lb^{105}$ each independently represent a single bond, —CO—, or —SO$_2$—. $n_{101}$ is 0 or 1.

According to a third aspect of the present invention, there is provided a method for forming a resist pattern including: forming a resist film using the positive-type resist composition according to any one of the first or second aspect on a support; exposing the resist film; and developing the exposed resist film to form a resist pattern.

According to a fourth aspect of the present invention, there is provided a photo-reactive quencher including a compound (md) represented by the following general formula (m0-d).

[Chemical formula 3]

In general formula (m0-d), $Z^{01}$ to $Z^{04}$ each independently represent a substituent having electron withdrawing properties, $Rb^{21}$ and $Rb^{22}$ each independently represent an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^{1}$ represents an aryl group which may have a substituent, an alkyl group which may have a substituent, or an alkenyl group which may have a substituent, and n1 and n2 each independently represent an integer of 0 to 3.

X0⁻ represents an organic anion represented by any one of general formulae (d1-an-1) to (d1-an-3).

In general formulae (d1-an-1) to (d1-an-3), $Rd^{1}$ to $Rd^{4}$ represent a cyclic group which may have a substituent, a chain-like alkyl group which may have a substituent, or a chain-like alkenyl group which may have a substituent. However, two or more fluorine atoms are not bonded to a carbon atom adjacent to the S atom (shown in formula (d1-an-2)) in $Rd^{2}$. $Yd^{1}$ represents a single bond, or a divalent linking group.

According to a fifth aspect of the present invention, there is provided a polymeric compound including a structural unit derived from a compound represented by the following general formula (a6-1).

[Chemical formula 4]

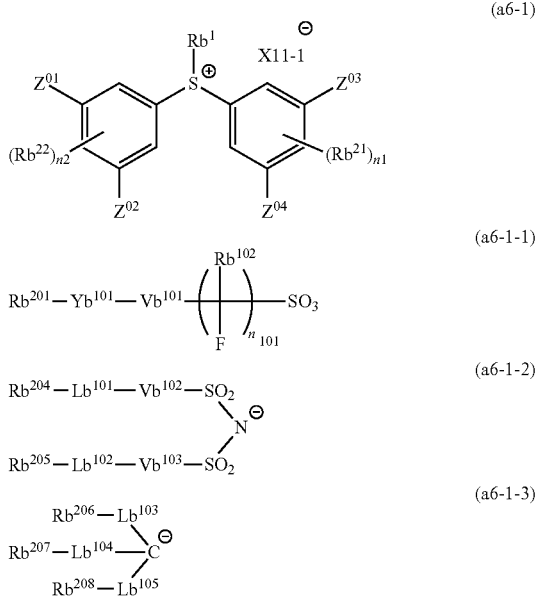

In general formula (a6-1), $Z^{01}$ to $Z^{04}$ each independently represent a substituent having electron withdrawing properties, $Rb^{21}$ and $Rb^{22}$ each independently represent an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^1$ represents an aryl group which may have a substituent, an alkyl group which may have a substituent, or an alkenyl group which may have a substituent, and n1 and n2 each independently represent an integer of 0 to 3.

X11-1⁻ represents an organic anion represented by any one of general formulae (a6-1-1) to (a6-1-3). In general formulae (a6-1-1) to (a6-1-3), $Rb^{201}$ represents a chain-like alkenyl group which may have a substituent, $Rb^{204}$ represents a cyclic group which may have a substituent, a chain-like alkyl group which may have a substituent, or a chain-like alkenyl group which may have a substituent, and $Rb^{205}$ represents a chain-like alkenyl group which may have a substituent.

$Rb^{206}$ to $Rb^{208}$ each independently represent a cyclic group which may have a substituent, a chain-like alkyl group which may have a substituent, or a chain-like alkenyl group which may have a substituent, with the proviso that at least one of $Rb^{206}$ to $Rb^{208}$ represents a chain-like alkenyl group which may have a substituent.

$Rb^{102}$ represents a fluorine atom or a fluorinated alkyl group having 1 to 5 carbon atoms. $Yb^{101}$ represents a single bond, or a divalent linking group including an oxygen atom. $Vb^{101}$ to $Vb^{103}$ each independently represent a single bond, an alkylene group, a fluorinated alkylene group, an arylene group, or a fluorinated arylene group. $Lb^{101}$ and $Lb^{102}$ each independently represent a single bond, or an oxygen atom. $Lb^{103}$ to $Lb^{105}$ each independently represent a single bond, —CO—, or —SO$_2$—. $n_{101}$ is 0 or 1.

According to the present invention, it is possible to provide a resist composition which can form a resist pattern having excellent lithography properties, and a method for forming a resist pattern using the resist composition.

DETAILED DESCRIPTION OF THE INVENTION

In the present description and claims, the term "aliphatic" is a relative concept used in relation to the term "aromatic", and defines a group or a compound that has no aromaticity.

The term "alkyl group" includes a linear, branched or cyclic, monovalent saturated hydrocarbon group, unless otherwise specified. The same applies for an alkyl group within an alkoxy group.

The term "alkylene group" includes a linear, branched or cyclic, divalent saturated hydrocarbon group, unless otherwise specified.

A "halogenated alkyl group" is a group in which a part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which a part or all of the hydrogen atoms of an alkyl group or an alkylene group is substituted with a fluorine atom.

The term "structural unit" refers to a monomer unit that contributes to the formation of a polymeric compound (resin, polymer, copolymer).

A "structural unit derived from an acrylic ester" refers to a structural unit that is formed by the cleavage of the ethylenic double bond of an acrylic ester.

An "acrylic ester" refers to a compound in which the terminal hydrogen atom of the carboxy group of acrylic acid ($CH_2$=CH—COOH) is substituted with an organic group.

With respect to the acrylic ester, the hydrogen atom bonded to the carbon atom present on the α-position may be substituted with a substituent. The substituent ($R^\alpha$) that may substitute the hydrogen atom bonded to the carbon atom present on the α-position is an atom other than the hydrogen atom or a group, and examples thereof include an alkyl group having 1 to 5 carbon atoms, a halogenated alkyl group having 1 to 5 carbon atoms, and a hydroxyalkyl group. A carbon atom on the α-position of an acrylic ester refers to the carbon atom bonded to the carbonyl group, unless specified otherwise.

Hereinafter, an acrylic ester having a substituent which substitutes the hydrogen atom bonded to the carbon atom present on the α-position is sometimes referred to as "α-substituted acrylic ester". Further, acrylic esters and α-substituted acrylic esters are collectively referred to as "(α-substituted) acrylic ester".

A "structural unit derived from a hydroxystyrene derivative" refers to a structural unit that is formed by the cleavage of the ethylenic double bond of hydroxystyrene or a hydroxystyrene derivative.

The term "hydroxystyrene derivative" includes compounds in which the hydrogen atom at the α-position of hydroxystyrene is substituted with a substituent such as an alkyl group or a halogenated alkyl group; and derivatives thereof. Examples of the derivatives thereof include hydroxystyrene in which the hydrogen atom of the hydroxyl group is substituted with an organic group and which may have a substituent which substitutes the hydrogen atom on the α-position; and hydroxystyrene which has a substituent other than a hydroxyl group bonded to the benzene ring and may have a substituent which substitutes the hydrogen atom on the α-position. Here, the α-position (carbon atom on the α-position) refers to the carbon atom having the benzene ring bonded thereto, unless specified otherwise.

As the substituent which substitutes the hydrogen atom on the α-position of hydroxystyrene, the same substituents as those described above for the substituent on the α-position of the aforementioned α-substituted acrylic ester can be exemplified.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes a compound in which the hydrogen atom at the α-position of vinylbenzoic acid is substituted with other substituents such as an alkyl group or a halogenated alkyl group; and derivatives thereof. Examples of the derivatives thereof include vinylbenzoic acid in which the hydrogen atom of the carboxy group is substituted with an organic group and may have a substituent which substitutes the hydrogen atom on the α-position; and vinylbenzoic acid which has a substituent other than a hydroxyl group and a carboxy group bonded to the benzene ring and may have a substituent which substitutes the hydrogen atom on the α-position. Here, the α-position (carbon atom on the α-position) refers to the carbon atom having the benzene ring bonded thereto, unless specified otherwise.

The term "styrene derivative" includes a compound in which the hydrogen atom on the α-position of styrene is substituted with other substituents such as an alkyl group and a halogenated alkyl group.

A "structural unit derived from styrene" or "structural unit derived from a styrene derivative" refers to a structural unit that is formed by the cleavage of the ethylenic double bond of styrene or a styrene derivative.

As for the alkyl group as a substituent on the α-position, a linear or branched alkyl group is preferable, and examples thereof include alkyl groups having 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Examples of the halogenated alkyl group as the substituent on the α-position include a group in which a part or all of the hydrogen atoms of the aforementioned "alkyl group as the substituent on the α-position" is substituted with halogen atoms. Examples of the halogen atom include a fluorine atom, a chlorine atom, a bromine atom and an iodine atom, and a fluorine atom is particularly preferable.

Examples of the hydroxyalkyl group as the substituent on the α-position include a group in which a part or all of the hydrogen atoms of the aforementioned "alkyl group as the substituent on the α-position" is substituted with a hydroxyl group. The number of hydroxyl groups in the hydroxyalkyl group is preferably 1 to 5, and most preferably 1.

A case with the description "may have a substituent" includes both of the case where the hydrogen atom (—H) is substituted with a monovalent group and the case where the methylene group (—CH$_2$—) is substituted with a divalent group.

The term "exposure" is used as a general concept that includes irradiation with any form of radiation.

Positive-Type Resist Composition

The positive-type resist composition (hereinafter, simply referred to as "a resist composition") according to the first aspect of the present invention is a positive-type resist composition which generates an acid upon exposure and whose solubility in an alkali developing solution increases under the action of an acid, and includes a base material component (A) whose solubility in an alkali developing solution increases under the action of an acid, and a compound (m) represented by the following general formula (m0).

[Chemical formula 5]

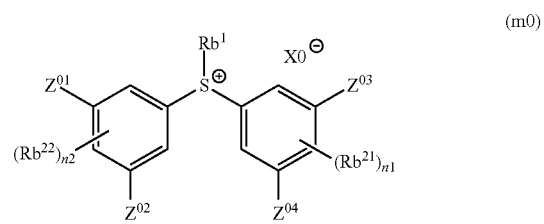

(m0)

In general formula (m0), $Z^{01}$ to $Z^{04}$ each independently represent a substituent having electron withdrawing properties, $Rb^{21}$ and $Rb^{22}$ each independently represent an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^1$ represents an aryl group which may have a substituent, an alkyl group which may have a substituent, or an alkenyl group which may have a substituent, n1 and n2 each independently represent an integer of 0 to 3, and X0$^-$ represents an organic anion.

The positive-type resist composition has an acid generating ability which generates an acid upon exposure, and the component (A) may generate an acid upon exposure or an additive component separately mixed with the component (A) may generate an acid upon exposure.

Specifically, in the embodiment, in the positive-type resist composition, (1) The composition may contain an acid generator component (B) which generates an acid upon exposure;

(2) The component (A) may be a component which generates an acid upon exposure; and (3) The component (A) is a component which generates an acid upon exposure, and further the component (B) may be contained.

In other words, in cases of the aforementioned (2) and (3), the component (A) is a "base material component which generates an acid upon exposure and whose solubility in a developing solution increases under the action of an acid". As the component (A) of this case, for example, a polymeric compound having a structural unit (a6) derived from a compound represented by the following general formula (a6-1) is preferable. As this polymeric compound, a resin having a structural unit which generates an acid upon exposure can be used. As the structural unit which generates an acid upon exposure, a well-known compound can be used.

In the embodiment, the aforementioned case (1) is particularly preferable for the resist composition.

Examples of the base material component (A) whose solubility in an alkali developing solution increases under the action of an acid and which is contained in the positive-type resist composition according to the first aspect of the present invention include the same component as the base material component (A) which will be described below in the first embodiment of the present invention.

Compound (m)

The compound (m) is represented by the following general formula (m0). The compound (m) is decomposed by exposure to generate an acid.

[Chemical formula 6]

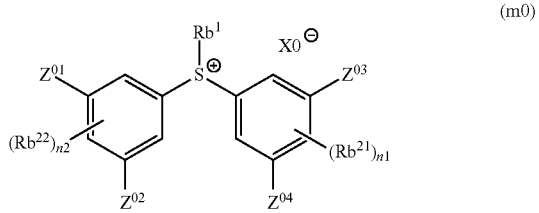

(m0)

In general formula (m0), $Z^{01}$ to $Z^{04}$ each independently represent a substituent having electron withdrawing properties, $Rb^{21}$ and $Rb^{22}$ each independently represent an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^{1}$ represents an aryl group which may have a substituent, an alkyl group which may have a substituent, or an alkenyl group which may have a substituent, n1 and n2 each independently represent an integer of 0 to 3, and $XO^{-}$ represents an organic anion.

$Z^{01}$ to $Z^{04}$

In general formula (m0), $Z^{01}$ to $Z^{04}$ each independently represent a substituent having electron withdrawing properties.

Examples of the substituent having electron withdrawing properties for $Z^{01}$ to $Z^{04}$ include a halogen atom, a halogenated alkyl group, an ester group, a sulfoxide group, a cyano group, an amide group, a carboxy group, and a carbonyl group.

Among these substituents, a halogen atom or a halogenated alkyl group is preferable from a viewpoint of improving sensitivity of the resist composition.

As the halogen atom, a fluorine atom or a chlorine atom is preferable and a fluorine atom is more preferable.

As the halogenated alkyl group, a halogenated alkyl group having 1 to 5 carbon atoms is preferable, a halogenated alkyl group having 1 to 3 carbon atoms is more preferable, and a trifluoromethyl group is particularly preferable.

The substituents having electron withdrawing properties for $Z^{01}$ to $Z^{04}$ each independently may be the same as or different from each other, but $Z^{01}$ to $Z^{04}$ are preferably the same substituent having electron withdrawing properties, $Z^{01}$ to $Z^{04}$ are more preferably the same halogen atoms, and $Z^{01}$ to $Z^{04}$ are particularly preferably fluorine atoms, from a viewpoint of obtaining easy operability in synthesis.

$Rb^{21}$ and $Rb^{22}$

In general formula (m0), $Rb^{21}$ and $Rb^{22}$ each independently represent an alkyl group, an alicyclic hydrocarbon group which may have a substituent, or a hydroxyl group. However, the aforementioned substituents having electron withdrawing properties are not included in the substituent for $Rb^{21}$ and $Rb^{22}$.

Alkyl Group

The alkyl group for $Rb^{21}$ and $Rb^{22}$ is preferably a linear or branched alkyl group having 1 to 5 carbon atoms. Examples thereof include a methyl group, an ethyl group, a propyl group, an isopropyl group, an n-butyl group, an isobutyl group, a tert-butyl group, a pentyl group, an isopentyl group, and a neopentyl group.

Alicyclic Hydrocarbon Group which May have a Substituent

The alicyclic hydrocarbon group for $Rb^{21}$ and $Rb^{22}$ may be polycyclic or monocyclic. As the monocyclic alicyclic hydrocarbon group, a group in which one or more hydrogen atoms are removed from monocycloalkane is preferable. The monocycloalkane preferably has 3 to 8 carbon atoms and examples thereof include cyclopentane, cyclohexane, and cyclooctane. As the polycyclic alicyclic hydrocarbon group, a group in which one or more hydrogen atoms are removed from polycycloalkane is preferable. The polycycloalkane preferably has 7 to 12 carbon atoms and examples thereof include adamantane, norbornane, isobornane, tricyclodecane, and tetracyclododecane.

As the substituent for $Rb^{21}$ and $Rb^{22}$, an alkyl group can be exemplified.

The alkyl group as the substituent is preferably an alkyl group having 1 to 5 carbon atoms, and more preferably a methyl group, an ethyl group, a propyl group, an n-butyl group, or a tert-butyl group.

Among the above, as for $Rb^{21}$ and $Rb^{22}$, an alkyl group is preferable. The alkyl group is preferably an alkyl group having 1 to 5 carbon atoms, more preferably an alkyl group having 1 to 3 carbon atoms, and particularly preferably a methyl group or an ethyl group.

$Rb^{1}$ $Rb^{1}$ represents an aryl group which may have a substituent, an alkyl group which may have a substituent, or an alkenyl group which may have a substituent.

Aryl Group which May have a Substituent

As the aryl group for $Rb^{1}$, an unsubstituted aryl group having 6 to 20 carbon atoms can be exemplified, and a phenyl group or a naphthyl group is preferable.

Alkyl Group which May have a Substituent or Alkenyl Group which May have a Substituent The alkyl group for $Rb^{1}$ is preferably a chain-like or cyclic alkyl group having 1 to 30 carbon atoms.

The alkenyl group for $Rb^{1}$ preferably has 2 to 10 carbon atoms.

Substituent for $Rb^{1}$

Examples of the substituent which $Rb^{1}$ may have include an alkyl group, a halogen atom, a halogenated alkyl group, a carbonyl group, a cyano group, an amino group, an aryl group, an arylthio group, and the group represented by any one of the following general formulae (ca-r-1) to (ca-r-7).

[Chemical formula 7]

—O—R$^{\prime 201}$     [ca-r-1]

[ca-r-2]

[ca-r-3]

[ca-r-4]

-continued

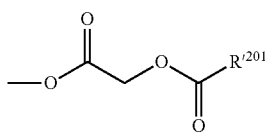
[ca-r-5]

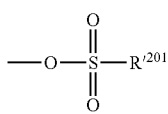
[ca-r-6]

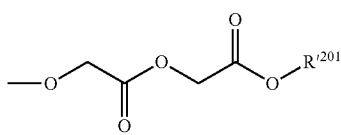
[ca-r-7]

In general formulae (ca-r-1) to (ca-r-7), each $R'^{201}$ independently represents a hydrogen atom, a cyclic group, a chain-like alkyl group, or a chain-like alkenyl group, which may have a substituent.

As the cyclic group which may have a substituent, the chain-like alkyl group which may have a substituent, or the chain-like alkenyl group which may have a substituent for $R'^{201}$, the same group as an acid dissociable group represented by general formula (a1-r-2) shown below as the cyclic group which may have a substituent or the chain-like alkyl group which may have a substituent can be exemplified, in addition to the same group as for $R^{101}$ of general formula (b-1) shown in a second embodiment described below.

As for $Rb^1$, the aryl group which may have a substituent is preferable.

n1 and n2 n1 and n2 each independently represent an integer of 0 to 3, and is more preferably 0 or 1.

A cation moiety of the compound represented by general formula (m0) is preferably a cation moiety represented by the following general formula (m0-1).

[Chemical formula 8]

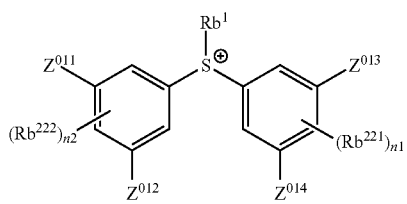
(m0-1)

In general formula (m0-1),
$Z^{011}$ to $Z^{014}$ each independently represent a halogen atom,
$Rb^{221}$ and $Rb^{222}$ each independently represent an alkyl group,
$Rb^1$ represents an aryl group which may have a substituent, an alkyl group which may have a substituent, or an alkenyl group which may have a substituent, and
n1 and n2 each independently represent an integer of 0 to 3.

In general formula (m0-1), $Z^{011}$ to $Z^{014}$ each independently represent a halogen atom, a fluorine atom or a chlorine atom is preferable, and a fluorine atom is more preferable.

In general formula (m0-1), $Rb^{221}$ and $Rb^{222}$ each independently represent an alkyl group, and examples of the alkyl group include the same group as the alkyl group described for $Rb^{21}$ and $Rb^{22}$ of general formula (m0). Among these, as for $Rb^{221}$ and $Rb^{222}$, a methyl group or an ethyl group is preferable and a methyl group is more preferable.

In general formula (m0-1), the description for $Rb^1$, n1, and n2 is the same as the description for $Rb^1$, n1, and n2 of general formula (m0).

Further, as the cation moiety of the compound represented by general formula (m0), a cation moiety represented by the following general formula (m0-1-1) is more preferable.

[Chemical formula 9]

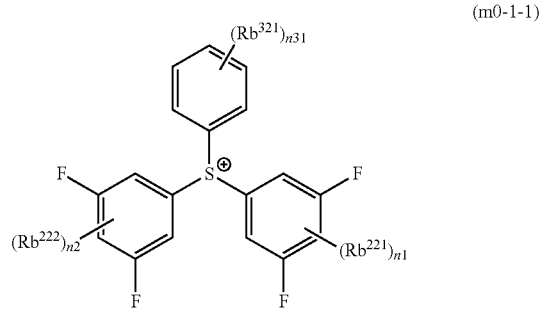
(m0-1-1)

In general formula (m0-1-1),
$Rb^{221}$ and $Rb^{222}$ each independently represent an alkyl group,
n1 and n2 each independently represent an integer of 0 to 3,
$Rb^{321}$ represents an alkyl group, or a substituent represented by any one of general formulae (ca-r-1) to (ca-r-7), and
n31 represents an integer of 0 to 5.

In general formula (m0-1-1), as the alkyl group for $Rb^{221}$ and $Rb^{222}$, an alkyl group having 1 to 5 carbon atoms is preferable, an alkyl group having 1 to 3 carbon atoms is more preferable, and a methyl group or an ethyl group is particularly preferable.

n31 represents an integer of 0 to 5, and more preferably an integer of 0 to 3.

In general formula (m0-1-1), $Rb^{321}$ represents an alkyl group or a substituent represented by any one of general formulae (ca-r-1) to (ca-r-7).

In the case where $Rb^{321}$ is an alkyl group, a methyl group or an ethyl group is preferable.

In the case where $Rb^{321}$ is a substituent represented by any one of general formulae (ca-r-1) to (ca-r-7), a group represented by general formula (ca-r-1) is preferable. In this case, as for $R'^{201}$ in the group represented by general formula (ca-r-1), an unsubstituted alkyl group having 1 to 5 carbon atoms is preferable.

Hereinafter, examples of a cation moiety of a compound (m0) will be shown.

[Chemical formula 10]

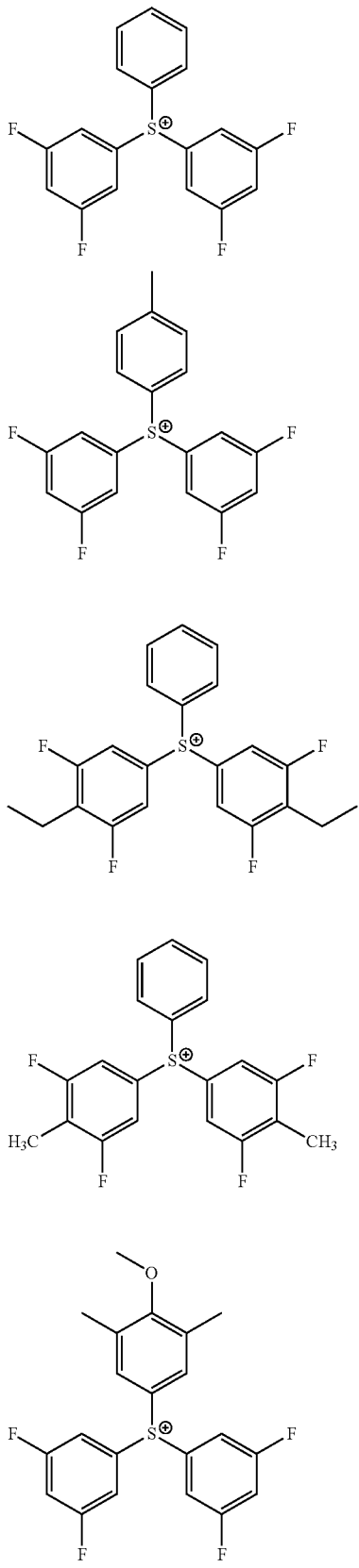

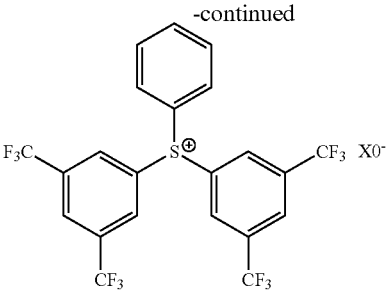

An organic anion represented by X0⁻ is not particularly limited, and various organic anions of the compounds known for an acid generator for a chemically amplified-type resist until now can be used.

Examples of the organic anion represented by X0⁻ include sulfonate anion, sulfonyl imide anion, sulfonyl methide anion, camphor sulfonate anion, and carboxylate anion.

More specifically, the organic anion represented by X0⁻ is preferably an anion represented by any one of general formulae (m-an-1) to (m-an-3) shown below, or the same anion as the organic anion represented by any one of general formulae (d1-1) to (d1-3) can be exemplified.

The content ratio of the compound (m) in the positive-type resist composition according to the first aspect of the present invention is not particularly limited, and the content ratio can be appropriately adjusted depending on the desired properties of the positive-type resist composition.

The compound (m) represented by general formula (m0) shown above can generate an acid by being decomposed by exposure. The cation moiety of the compound (m) has a structure which is easily decomposed as the substituent having electron withdrawing properties is introduced thereto. Therefore, according to the positive-type resist composition of the present invention, an effect of increasing sensitivity at the time of forming a resist pattern is obtained.

Method for Producing a Compound (m)

A method for producing the compound (m) will be described.

The method for producing the compound (m) is not particularly limited, and the compound (m) can be produced by using the well-known method, for example, by the following first to third steps.

The compound (m) can be produced by, for example, the producing method which includes a first step of reacting a compound represented by general formula (m1) with thionyl chloride (or a thionyl chloride derivative) to synthesize a compound represented by general formula (m2); a second step of introducing a desired substituent to the obtained compound represented by general formula (m2) to obtain a compound represented by general formula (m3); and a third step of obtaining a compound (m0) by exchanging salts with the obtained compound represented by general formula (m3).

[Chemical formula 11]

First step

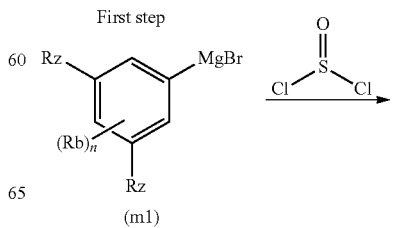

(m1)

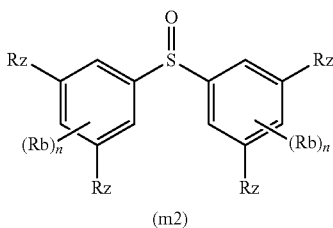

(m2)

In the formulae, Rz corresponds to $Z^{01}$ to $Z^{04}$ of general formula (m0) and each Rz independently represents a substituent having electron withdrawing properties.

Rb corresponds to $Rb^{21}$ and $Rb^{22}$ of general formula (m0), and each Rb independently represents an alkyl group, an alicyclic hydrocarbon group which may have a substituent, or a hydroxyl group.

n corresponds to n1 and n2 of general formula (m0) and each n independently represents an integer of 0 to 3.

[Chemical formula 12]

Second Step

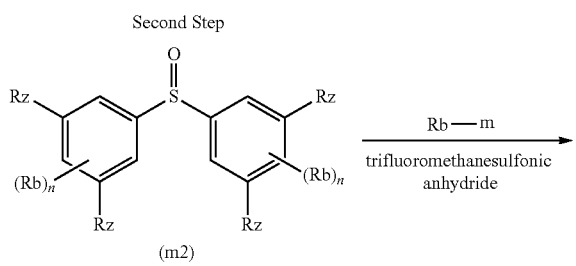

(m3)

In the formulae, Rz corresponds to $Z^{01}$ to $Z^{04}$ of general formula (m0) and each Rz independently represents a substituent having electron withdrawing properties.

Rb corresponds to $Rb^{21}$ and $Rb^{22}$ of general formula (m0) and each Rb independently represents an alkyl group, an alicyclic hydrocarbon group which may have a substituent, or a hydroxyl group.

n corresponds to n1 and n2 of general formula (m0) and each n independently represents an integer of 0 to 3.

Rb-m represents a compound having an aryl group which may have a substituent, an alkyl group which may have a substituent, or an alkenyl group which may have a substituent.

$Rb^1$ represents an aryl group which may have a substituent, an alkyl group which may have a substituent, or an alkenyl group which may have a substituent.

[Chemical formula 13]

Third Step

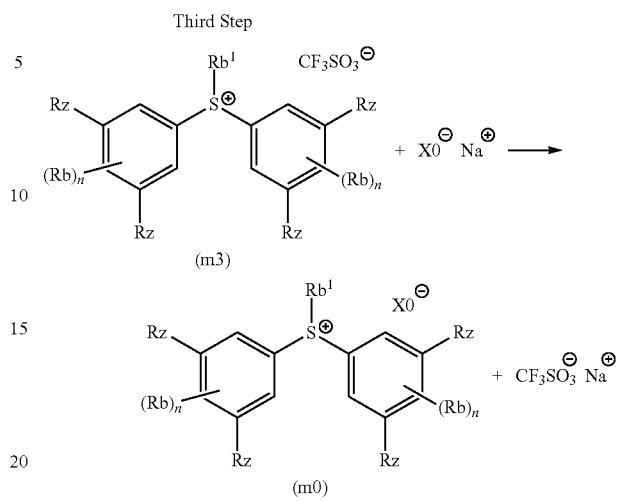

(m0)

In the formulae, Rz corresponds to $Z^{01}$ to $Z^{04}$ of general formula (m0) and each Rz independently represents a substituent having electron withdrawing properties.

Rb corresponds to $Rb^{21}$ and $Rb^{22}$ of general formula (m0) and each Rb independently represents an alkyl group, an alicyclic hydrocarbon group which may have a substituent, or a hydroxyl group.

n corresponds to n1 and n2 of general formula (m0) and each n independently represents an integer of 0 to 3. $X0^-$ represents an organic anion.

$Rb^1$ represents an aryl group which may have a substituent, an alkyl group which may have a substituent, or an alkenyl group which may have a substituent.

As for each compound represented by formulae (m1) to (m3) shown above, a commercially available compound may be used or a compound synthesized by the well-known producing method may be used.

As a solvent used in the first step to second step, the thionyl chloride used, the compounds (m1) to (m3), the compound Rb-m, trifluoromethane sulfonic acid anhydride, or the like can be dissolved, any compound which does not react with the above, and examples thereof include dichloromethane, dichloroethane, chloroform, tetrahydrofuran, N,N-dimethylformamide, acetonitrile, and propionitrile.

In the third step, it is possible to derive the compound (m0) by exchanging salts with an anion represented by any one of general formulae (m-an-1) to (m-an-3) shown below, or an organic anion represented by any one of general formulae (d1-1) to (d1-3) shown below.

After the reaction is finished, a compound in a reaction liquid may be isolated or purified. The well-known method can be used for isolation and purification, and for example, any one of condensation, solvent extraction, distillation, crystallization, recrystallization, and chromatography can be used alone or two or more thereof can be used in combination.

The structure of the compound obtained according to the above can be confirmed by a general organic analysis method such as a $^1$H-nuclear magnetic resonance (NMR) spectrometry, a $^{13}$C-NMR spectrometry, a $^{19}$F-NMR spectrometry, an infrared absorption (IR) spectrometry, mass spectrometry (MS), elementary analysis, and an X-ray crystal diffraction method.

As the positive-type resist composition according to the first aspect of the present invention, positive-type resist compositions of respective first and second embodiments shown below can be exemplified.

First Embodiment

A positive-type resist composition of the first embodiment (hereinafter, referred to as a "first positive-type resist composition") is a positive-type resist composition which generates an acid upon exposure and whose solubility in an alkali developing solution increases under the action of an acid, and the composition includes a base material component (A) whose solubility in an alkali developing solution increases under the action of an acid (hereinafter, referred to as "component (A)"), an acid generator component (B1) which generates an acid upon exposure (hereinafter, referred to as "component (B1)"), and a photo-reactive quencher (D1) (hereinafter, referred to as "component (D1)"), in which the component (B1) includes the compound (m).

If a resist film is formed by using the first positive-type resist composition and the resist film is selectively exposed, an acid is generated from the component (B1) in the exposed areas. Due to this action of the acid, solubility in an alkali developing solution of the component (A) is increased. Meanwhile, solubility in an alkali developing solution of the component (A) is not increased in the unexposed areas. Therefore, a difference in solubility in an alkali developing solution occurs between the exposed areas and the unexposed areas. Therefore, if the exposed resist film is alkali-developed, the exposed areas are removed and a positive-type resist pattern is formed.

Component (A)

The base material component (A) whose solubility in an alkali developing solution increases under the action of an acid, which is included in the positive-type resist composition of the present invention, will be described.

In the embodiment, the "base material component" is an organic compound having a film forming ability and an organic compound having a molecular weight of 500 or more is preferably used. If the molecular weight of the organic compound is 500 or more, the film forming ability is improved and additionally, a photosensitive resin pattern of a nano-level is easily formed.

The organic compound used as the base material component is classified into a non-polymer and a polymer.

A non-polymer having a molecular weight of 500 to less than 4,000 is normally used. The "low molecular compound" described below indicates a non-polymer having a molecular weight of 500 to less than 4,000.

A polymer having a molecular weight of 1,000 or more is normally used. The "resin" described below indicates a polymer having a molecular weight of 1,000 or more.

As the molecular weight of the polymer, a weight average molecular weight in terms of polystyrene obtained by gel permeation chromatography (GPC) is used.

As the component (A), the resin may be used, the low molecular compound may be used, and these may be used in combination.

The component (A) is a component whose solubility in an alkali developing solution increases under the action of an acid.

Also, component (A) of the embodiment may be a component which generates an acid upon exposure.

The component (A) of the embodiment preferably includes a resin component (A1) whose solubility in an alkali developing solution changes. The resin component (A1) preferably includes a structural unit (a9) represented by general formula (a9-1) or a structural unit (a10) including an aromatic hydrocarbon group having a hydroxy group.

Further, in addition to the aforementioned structural unit (a9) or (a10), the component (A) preferably includes a structural unit (hereinafter, may be referred to as a "structural unit (a1)") including an acid decomposable group whose polarity increases under the action of an acid, a structural unit (a12) represented by general formula (a12-1), a structural unit (hereinafter, may be referred to as a "structural unit (a2)") having a —SO$_2$-containing cyclic group, a lactone-containing cyclic group, a carbonate-containing cyclic group, or a heterocyclic group other than these, a structural unit (hereinafter, may be referred to as a "structural unit (a3)") including a polar group-containing aliphatic hydrocarbon group, or a structural unit (hereinafter, may be referred to as a "structural unit (a4)") including a non-acid-dissociative cyclic group.

Structural Unit (a9)

The structural unit (a9) is represented by the following general formula (a9-1).

[Chemical formula 14]

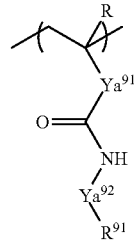

(a9-1)

In general formula (a9-1), R represents a hydrogen atom, an alkyl group having 1 to 5 carbon atoms, or a halogenated alkyl group having 1 to 5 carbon atoms. $Ya^{91}$ represents a single bond or a divalent linking group, $R^{91}$ represents a hydrocarbon group which may have a substituent, and $Ya^{92}$ represents a divalent linking group.

In general formula (a9-1), R represents a hydrogen atom, an alkyl group having 1 to 5 carbon atoms, or a halogenated alkyl group having 1 to 5 carbon atoms.

The alkyl group having 1 to 5 carbon atoms is preferably a linear or branched alkyl group having 1 to 5 carbon atoms, and examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group in which a part or all of the hydrogen atoms of the alkyl group having 1 to 5 carbon atoms is substituted with a halogen atom. Examples of the halogen atom include a fluorine atom, a chlorine atom, a bromine atom, and an iodine atom, and a fluorine atom is particularly preferable.

As for R, a hydrogen atom, an alkyl group having 1 to 5 carbon atoms, or a fluorinated alkyl group having 1 to 5 carbon atoms is preferable, and a hydrogen atom or a methyl group is most preferable, from a viewpoint of easy industrial availability.

n is a natural number and is preferably 1 to 5 and more preferably 1 to 3.

In general formula (a9-1), as the divalent linking group for $Ya^{91}$, the same divalent linking group for $Ya^{21}$ of formula (a2-1) shown below can be exemplified. $Ya^{91}$ is preferably a single bond.

In formula (a9-1), as the divalent linking group for $Ya^{92}$, the same divalent linking group for $Ya^{91}$ and the same divalent linking group for $Ya^{21}$ of formula (a2-1) can be exemplified. Among these, in the divalent linking group for $Ya^{92}$ of formula (a9-1), as the divalent hydrocarbon group which may have a substituent, a linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable, and examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

As the branched aliphatic hydrocarbon group, a branched alkylene group is preferable, and examples thereof include an alkylalkylene group including an alkylmethylene group such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, and —C($CH_2CH_3$)$_2$—; an alkylethylene group such as —CH($CH_3$)$CH_2$—, —CH($CH_3$)CH($CH_3$)—, —C($CH_3$)$_2CH_2$—, —CH($CH_2CH_3$)$CH_2$—, and —C($CH_2CH_3$)$_2$—$CH_2$—; an alkyltrimethylene group such as —CH($CH_3$)$CH_2CH_2$— and —$CH_2$CH($CH_3$)$CH_2$—; an alkyltetramethylene group such as —CH($CH_3$)$CH_2CH_2CH_2$— and —$CH_2$CH($CH_3$)$CH_2CH_2$—. An alkyl group of the alkylalkylene group is preferably a linear alkyl group having 1 to 5 carbon atoms.

In addition, in the divalent linking group for $Ya^{92}$ of formula (a9-1), examples of the divalent linking group which may have a hetero atom include —O—, —C(=O)—O—, —C(=O)—, —O—C(=O)—O—, —C(=O)—NH—, —NH—, —NH—C(=NH)— (H may be substituted with a substituent such as an alkyl group, an acyl group), —S—, —S(=O)$_2$—, —S(=O)$_2$—O—, —C(=S)—, a group represented by general formulae —$Y^{21}$—O—$Y^{22}$—, —$Y^{21}$—O—, —$Y^{21}$—C(=O)—O—, —C(=O)—O—$Y^{21}$, [$Y^{21}$—C(=O)—O]$_{m'}$—$Y^{22}$—, or —$Y^{21}$—O—C(=O)—$Y^{22}$— (in the formulae, $Y^{21}$ and $Y^{22}$ each independently represent a divalent hydrocarbon group which may have a substituent, O represents an oxygen atom, and m' represents an integer of 0 to 3). Among these, —C(=O)— or —C(=S)— is preferable.

In general formula (a9-1), examples of the hydrocarbon group for $R^{91}$ include an alkyl group, a monovalent alicyclic hydrocarbon group, an aryl group, and an aralkyl group.

The alkyl group for $R^{91}$ preferably has 1 to 8 carbon atoms, more preferably 1 to 6 carbon atoms, and still more preferably 1 to 4 carbon atoms, and the alkyl group may be linear or branched. Specific preferred examples thereof include a methyl group, an ethyl group, a propyl group, a butyl group, a hexyl group, and an octyl group.

The monovalent alicyclic hydrocarbon group for $R^{91}$ preferably has 3 to 20 carbon atoms, more preferably 3 to 12 carbon atoms, and the alicyclic hydrocarbon group may be polycyclic or monocyclic. As the monocyclic alicyclic hydrocarbon group, a group in which one or more hydrogen atoms are removed from monocycloalkane is preferable. The monocycloalkane preferably has 3 to 6 carbon atoms, and examples thereof include cyclobutane, cyclopentane, and cyclohexane. As the polycyclic alicyclic hydrocarbon group, a group in which one or more hydrogen atoms are removed from polycycloalkane is preferable, the polycycloalkane preferably has 7 to 12 carbon atoms, and examples thereof include adamantane, norbornane, isobornane, tricyclodecane, and tetracyclododecane.

The aryl group for $R^{91}$ preferably has 6 to 18 carbon atoms and more preferably 6 to 10 carbon atoms, and specifically, a phenyl group is particularly preferable.

The aralkyl group for $R^{91}$ preferably has 7 to 10 carbon atoms and examples of the aralkyl group having 7 to 10 carbon atoms include an arylalkyl group such as a benzyl group, a phenethyl group, a 1-naphthylmethyl group, a 2-naphthylmethyl group, a 1-naphthylethyl group, and a 2-naphthylethyl group.

In the hydrocarbon group for $R^{91}$, a part or all of the hydrogen atoms of the hydrocarbon group is preferably substituted with a fluorine atom, and 30% to 100% of the hydrogen atom of the hydrocarbon group is more preferably substituted with a fluorine atom. Among these, a perfluoroalkyl group in which the hydrogen atom of the aforementioned alkyl group is entirely substituted with a fluorine atom is particularly preferable.

The hydrocarbon group for $R^{91}$ may have a substituent. Examples of the substituent include a halogen atom, an oxo group (=O), a hydroxyl group (—OH), an amino group (—$NH_2$), and —$SO_2$—$NH_2$. In addition, a carbon atom configuring the hydrocarbon group may be partially substituted with a substituent including a hetero atom. Examples of the substituent including a hetero atom include —O—, —NH—, —N=, —C(=O)—O—, —S—, —S(=O)$_2$—, and —S(=O)$_2$—O—.

Examples of the hydrocarbon group having a substituent for $R^{91}$ include the lactone-containing cyclic group represented by any one of general formulae (a2-r-1) to (a2-r-7).

Examples of the hydrocarbon group having a substituent for $R^{91}$ include each —$SO_2$-containing cyclic group represented by general formulae (a5-r-1) to (a5-r-4) shown below; a substituted aryl group represented by the following chemical formula, and a monovalent heterocyclic group. In the following formulae (r-ar-1) to (r-ar-8) and (r-hr-1) to (r-hr-10), "*" represents a valence bond for $Ya^{92}$.

[Chemical formula 15]

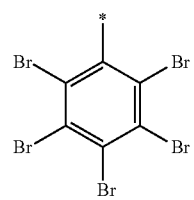

(r-ar-1)

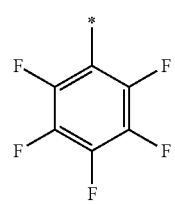

(r-ar-2)

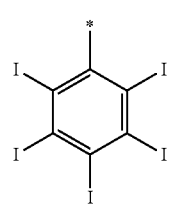

(r-ar-3)

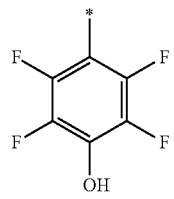 (r-ar-4)
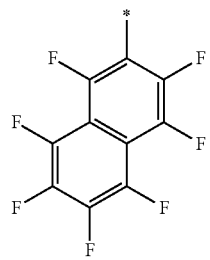 (r-ar-5)
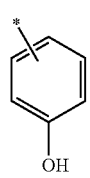 (r-ar-6)
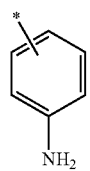 (r-ar-7)
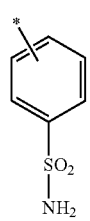 (r-ar-8)
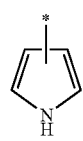 (r-hr-1)
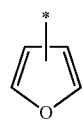 (r-hr-2)
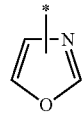 (r-hr-3)
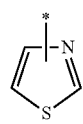 (r-hr-4)
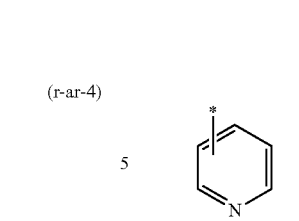 (r-hr-5)
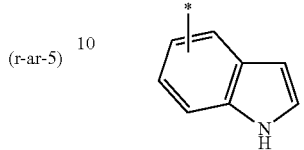 (r-hr-6)
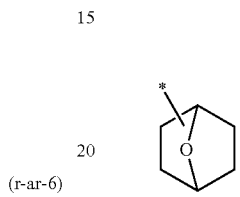 (r-hr-7)
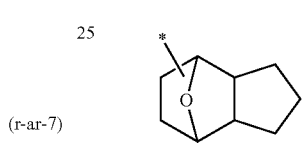 (r-hr-8)
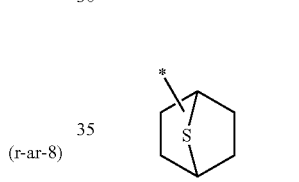 (r-hr-9)
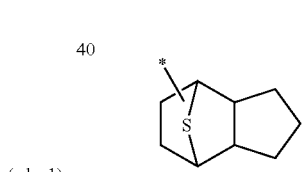 (r-hr-10)
Examples of the structural unit represented by the following general formula (a9-1) will be shown. Among the following formulae, $R^\alpha$ represents a hydrogen atom, a methyl group, or a trifluoromethyl group.
[Chemical formula 16]
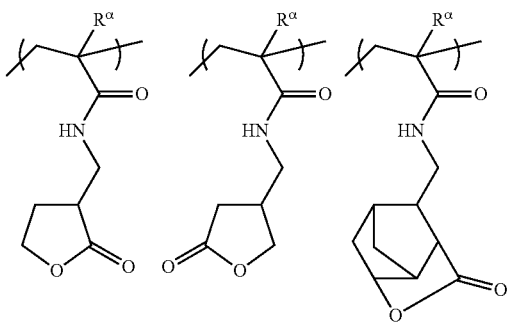

-continued

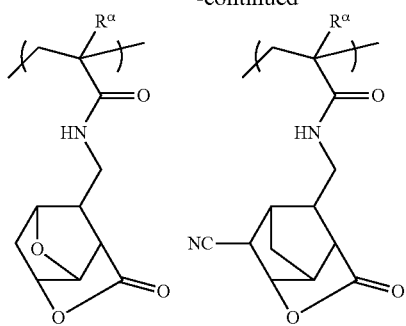

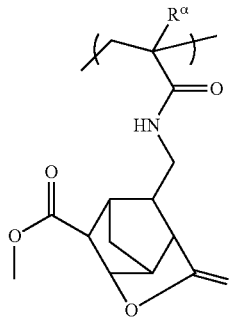

[Chemical formula 17]

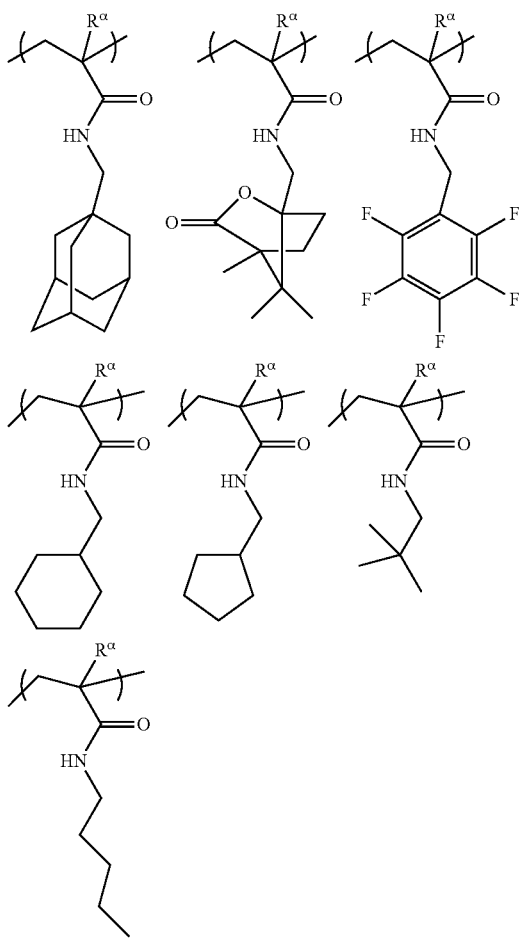

The structural unit represented by general formula (a9-1) is preferably a structural unit represented by the following general formula (a9-1-1).

[Chemical formula 18]

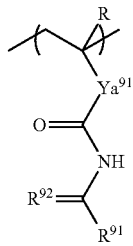
(a9-1-1)

In the formula, R represents a hydrogen atom, an alkyl group having 1 to 5 carbon atoms, or a halogenated alkyl group having 1 to 5 carbon atoms. $Ya^{91}$ represents a single bond or a divalent linking group, $R^{91}$ represents a hydrocarbon group which may have a substituent, and $R^{92}$ represents an oxygen atom or a sulfur atom.

In general formula (a9-1-1), the description for $Ya^{91}$, $R^{91}$, and R is the same as the description mentioned above. Also, $R^{92}$ represents an oxygen atom or a sulfur atom.

Examples of the structural unit represented by general formula (a9-1-1) will be shown below. In the following formulae, $R^\alpha$ represents a hydrogen atom, a methyl group, or a trifluoromethyl group.

[Chemical formula 19]

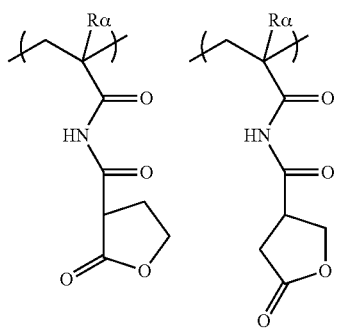

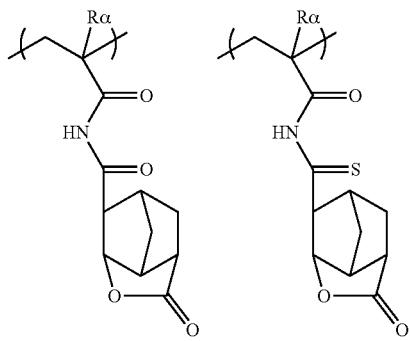

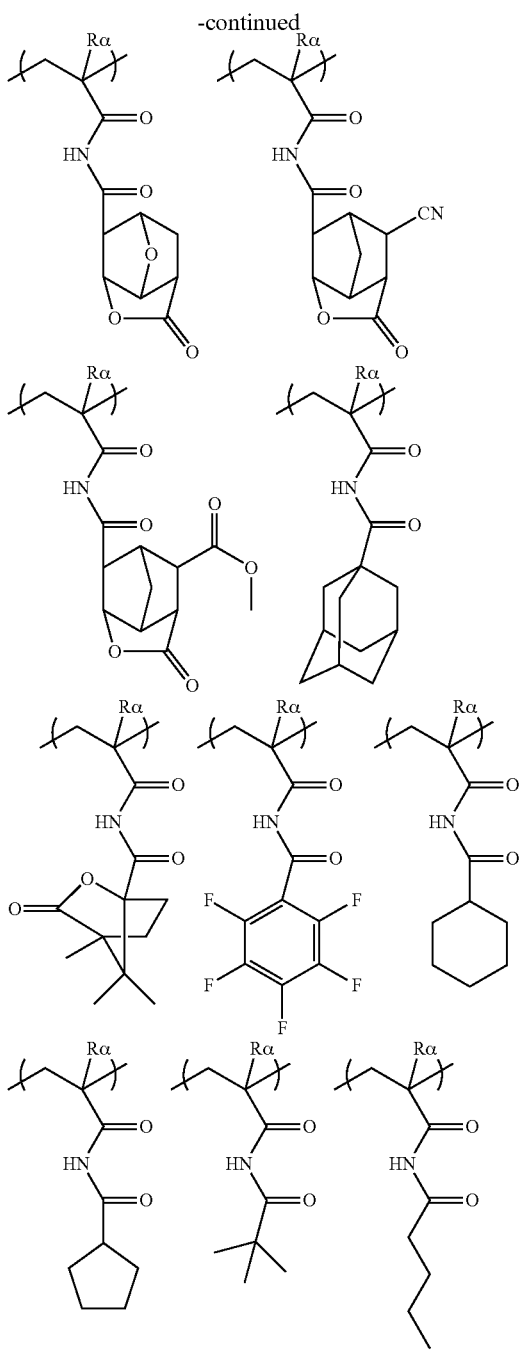

The type of the structural unit (a9) included in the component (A1) may be one or two or more.

In the case where the component (A1) includes the structural unit (a9), the ratio of the structural unit (a9) is preferably 1 mol % to 60 mol %, more preferably 3 mol % to 55 mol %, and particularly preferably 10 mol % to 50 mol % with respect to all of the structural units configuring the component (A1). If the ratio of the structural unit (a9) is set to the lower limit or more, lithography properties such as developing properties and EL margin are improved, and if the ratio is set to the upper limit or less, a good balance can be easily achieved with the other structural units.

Structural Unit (a10)

The structural unit (a10) is a structural unit including an aromatic hydrocarbon group having a hydroxy group.

Preferred examples of the structural unit (a10) include a structural unit (a10) represented by any one of the following general formulae (a10)-1-1 and (a10)-1-2, the following general formulae (a10)-2-1 and (a10)-2-2, the following general formulae (a10)-3-1 to (a10)-3-4, and the following general formulae (a10)-4-1 to (a10)-4-4.

[Chemical formula 20]

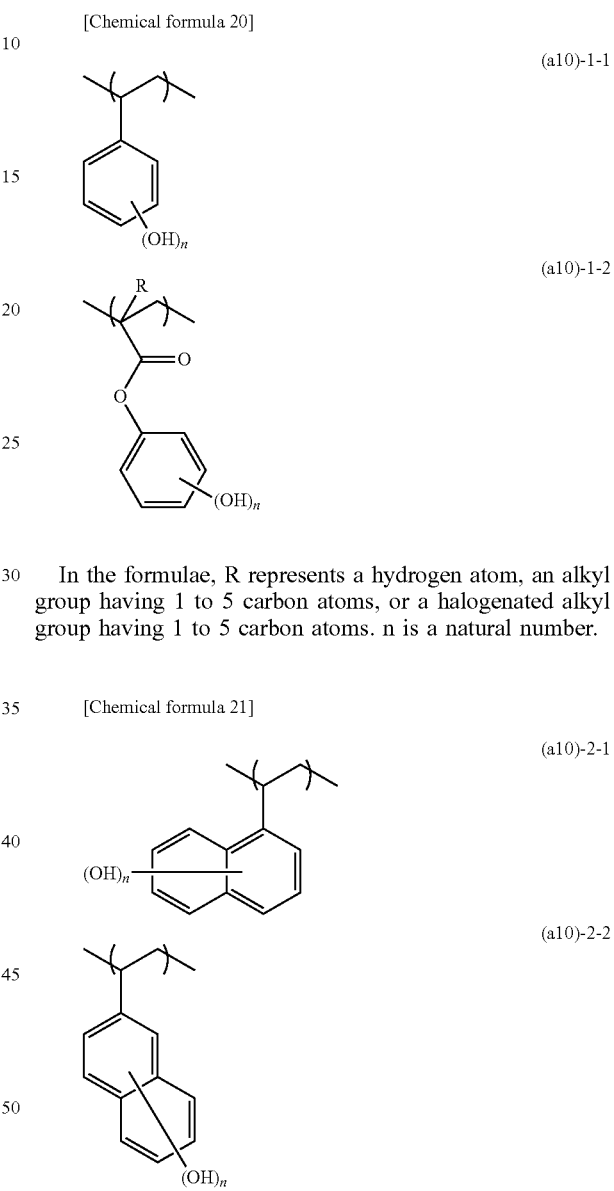

In the formulae, R represents a hydrogen atom, an alkyl group having 1 to 5 carbon atoms, or a halogenated alkyl group having 1 to 5 carbon atoms. n is a natural number.

[Chemical formula 21]

In the formulae, n is a natural number.

[Chemical formula 22]

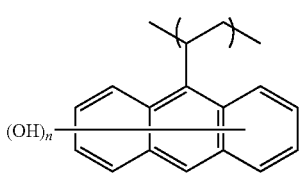

-continued (a10)-3-2

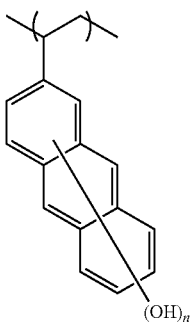

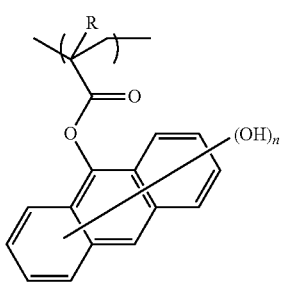

(a10)-3-3

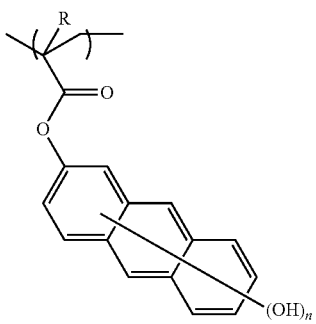

(a10)-3-4

In the formulae, R represents a hydrogen atom, an alkyl group having 1 to 5 carbon atoms, or a halogenated alkyl group having 1 to 5 carbon atoms. n is a natural number.

[Chemical formula 23]

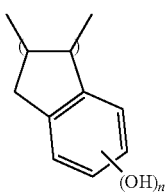

(a10)-4-1

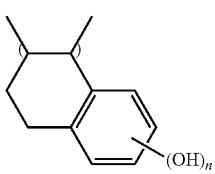

(a10)-4-2

-continued (a10)-4-3

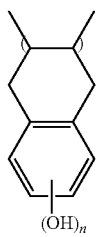

(a10)-4-4

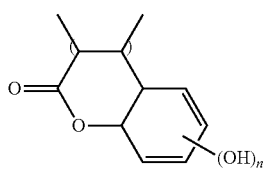

In the formulae, R represents a hydrogen atom, an alkyl group having 1 to 5 carbon atoms, or a halogenated alkyl group having 1 to 5 carbon atoms. n is a natural number.

In each structural unit (a10) represented by general formulae (a10)-1-2 and (a10)-3-3 to (a10)-3-4, R represents a hydrogen atom, an alkyl group having 1 to 5 carbon atoms, or a halogenated alkyl group having 1 to 5 carbon atoms.

The alkyl group having 1 to 5 carbon atoms is preferably a linear or branched alkyl group having 1 to 5 carbon atoms, and examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group in which a part or all of the hydrogen atoms of the alkyl group having 1 to 5 carbon atoms is substituted with a halogen atom. Examples of the halogen atom include a fluorine atom, a chlorine atom, a bromine atom, and an iodine atom, and a fluorine atom is particularly preferable.

As for R, a hydrogen atom, an alkyl group having 1 to 5 carbon atoms, or a fluorinated alkyl group having 1 to 5 carbon atoms is preferable, a hydrogen atom or a methyl group is most preferable from a viewpoint of easy industrial availability.

n is a natural number and is preferably 1 to 9, more preferably 1 to 7, particularly preferably 1 to 5, and extremely preferably 1 to 3.

Examples of the structural unit represented by general formula (a10)-1-1 will be shown below.

[Chemical formula 24]

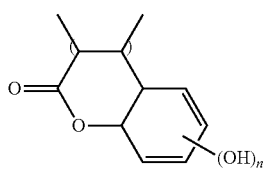

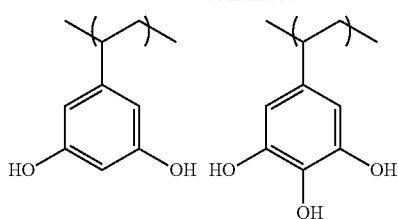

Examples of the structural unit represented by general formula (a10)-1-2 will be shown below.

[Chemical formula 25]

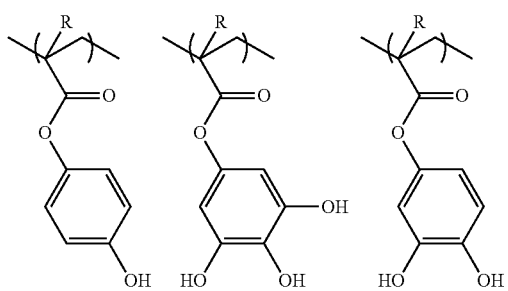

Examples of the structural unit represented by general formula (a10)-2-1 will be shown below.

[Chemical formula 26]

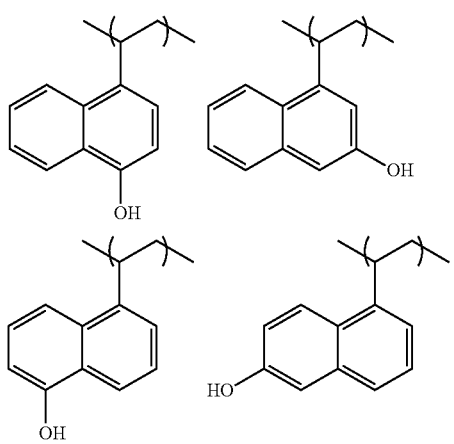

Examples of the structural unit represented by general formula (a10)-2-2 will be shown below.

[Chemical formula 27]

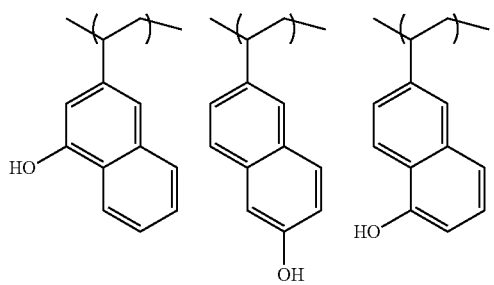

Examples of the structural unit represented by general formula (a10)-3-1 will be shown below.

[Chemical formula 28]

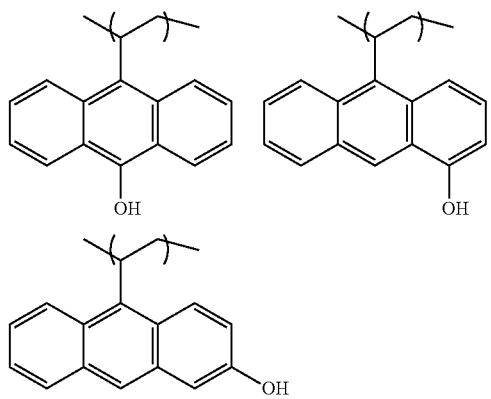

Examples of the structural unit represented by general formula (a10)-3-2 will be shown below.

[Chemical formula 29]

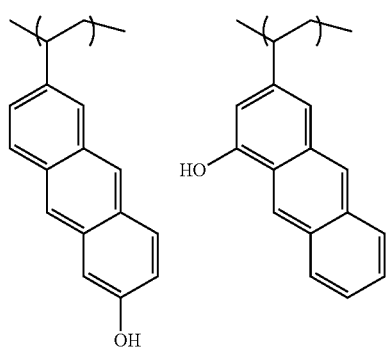

-continued
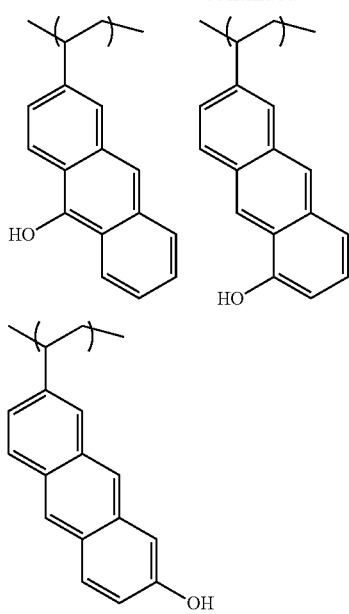
Examples of the structural unit represented by general formula (a10)-3-3 will be shown below.
[Chemical formula 30]
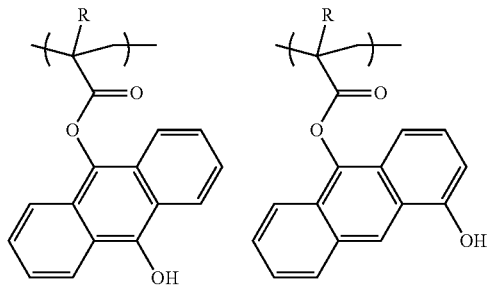
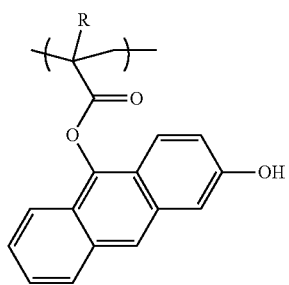
Examples of the structural unit represented by general formula (a10)-3-4 will be shown below.
[Chemical formula 31]
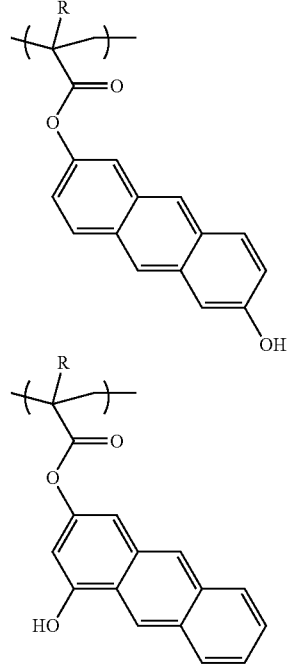
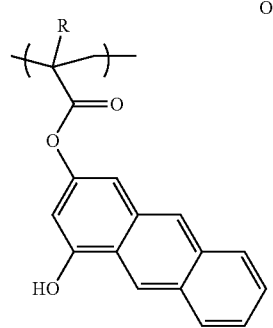
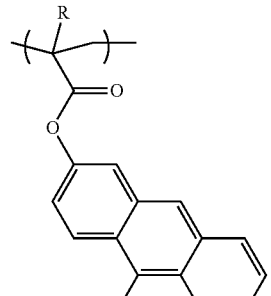
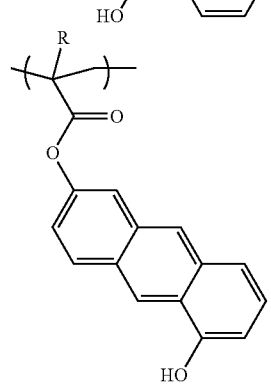
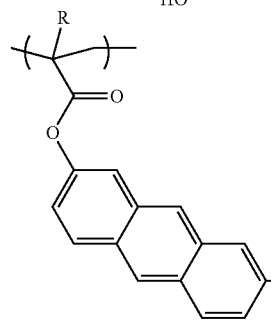

Examples of the structural unit represented by general formula (a10)-4-1 will be shown below.

[Chemical formula 32]

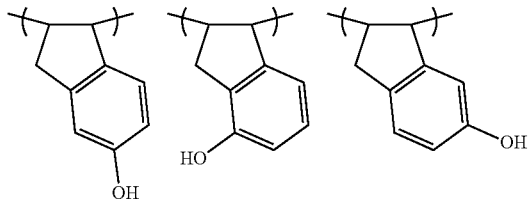

Examples of the structural unit represented by general formula (a10)-4-2 will be shown below.

[Chemical formula 33]

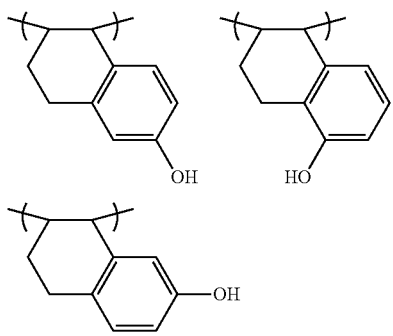

Examples of the structural unit represented by general formula (a10)-4-3 will be shown below.

[Chemical formula 34]

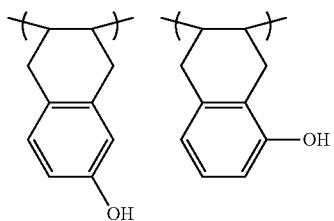

Examples of the structural unit represented by general formula (a10)-4-4 will be shown below.

[Chemical formula 35]

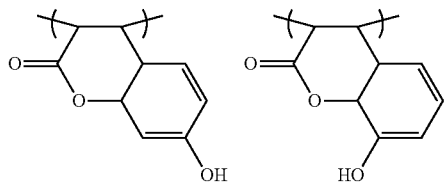

-continued

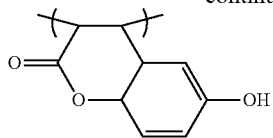

The type of the structural unit (a10) included in the component (A1) may be one or two or more.

In the case where the component (A1) has the structural unit (a10), the ratio of the structural unit (a10) is preferably 1 mol % to 60 mol % and more preferably 10 mol % to 50 mol % with respect to all of the structural units configuring the component (A1). If the ratio of the structural unit (a10) is set to the lower limit or more, lithography properties such as developing properties and EL margin are improved, and if the ratio is set to the upper limit or less, a good balance can be easily achieved with the other structural units.

Structural Unit (a1)

The structural unit (a1) is a structural unit containing an acid decomposable group that exhibits increased polarity by the action of an acid.

The term "acid decomposable group" refers to a group in which at least a part of the bond in the structure thereof is cleaved by the action of an acid.

Examples of acid decomposable groups which exhibit increased polarity by the action of acid include groups which are decomposed by the action of an acid to form a polar group.

Examples of the polar group include a carboxy group, a hydroxyl group, an amino group and a sulfo group ($—SO_3H$). Among these, a polar group containing —OH in the structure thereof (hereafter, referred to as "OH-containing polar group") is preferable, a carboxy group or a hydroxyl group is more preferable, and a carboxy group is particularly preferable.

More specifically, as an example of an acid decomposable group, a group in which the aforementioned polar group is protected with an acid dissociable group (such as a group in which the hydrogen atom of the OH-containing polar group is protected with an acid dissociable group) can be given.

The "acid dissociable group" refers to both (i) a group in which the bond between the acid dissociable group and the adjacent atom is cleaved by the action of an acid; and (ii) a group in which one of the bonds is cleaved by the action of an acid, and then a decarboxylation reaction occurs, thereby cleaving the bond between the acid dissociable group and the adjacent atom.

It is necessary that the acid dissociable group that constitutes the acid decomposable group is a group which exhibits a lower polarity than the polar group generated by the dissociation of the acid dissociable group. Thus, when the acid dissociable group is dissociated by the action of an acid, a polar group exhibiting a higher polarity than that of the acid dissociable group is generated, thereby increasing the polarity. As a result, the polarity of the entire component (A1) is increased. By the increase in the polarity, the solubility in an alkali developing solution changes and, the solubility in an organic developing solution is relatively decreased.

The acid dissociable group is not particularly limited, and any of the groups known conventionally as acid dissociable groups for the base resins of chemically amplified resists can be used.

Examples of the acid dissociable group for protecting the carboxy group or hydroxyl group as a polar group include the acid dissociable group represented by general formula (a1-r-1) shown below (hereafter, for the sake of convenience, sometimes referred to as "acetal-type acid dissociable group").

[Chemical formula 36]

(a1-r-1)

In the formula, $Ra'^1$ and $Ra'^2$ represent a hydrogen atom or an alkyl group; and $Ra'^3$ represents a hydrocarbon group, provided that $Ra'^3$ may be bonded to $Ra'^1$ or $Ra'^2$. "*" represents a valence bond.

In formula (a1-r-1), as the alkyl group for $Ra'^1$ and $Ra'^2$, the same alkyl groups as those described in the above alkyl groups as the substituent which may be bonded to the carbon atom on the α-position of the aforementioned α-substituted alkylester can be used, while a methyl group or ethyl group is preferable, and a methyl group is particularly preferable.

The hydrocarbon group for $Ra'^3$ is preferably an alkyl group having 1 to 20 carbon atoms, more preferably an alkyl group having 1 to 10 carbon atoms, and still more preferably a linear or branched alkyl group. Examples thereof include a methyl group, an ethyl group, a propyl group, an isopropyl group, an n-butyl group, an isobutyl group, a tert-butyl group, a pentyl group, an isopentyl group, a neopentyl group, a 1,1-dimethylethyl group, a 1,1-diethylpropyl group, a 2,2-dimethylpropyl group and a 2,2-dimethylbutyl group.

In the case where $Ra'^3$ represents a cyclic hydrocarbon group, the cyclic hydrocarbon group may be aliphatic or aromatic, and may be polycyclic or monocyclic. As the monocyclic aliphatic hydrocarbon group, a group in which one hydrogen atom is removed from a monocycloalkane is preferable. The monocycloalkane preferably has 3 to 8 carbon atoms, and examples thereof include cyclopentane, cyclohexane and cyclooctane. As the polycyclic aliphatic hydrocarbon group, a group in which one hydrogen atom is removed from a polycycloalkane is preferable, and the polycycloalkane preferably has 7 to 12 carbon atoms. Examples of the polycycloalkane include adamantane, norbornane, isobornane, tricyclodecane and tetracyclododecane.

In the case where the hydrocarbon group is an aromatic hydrocarbon group, examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings is substituted with a hetero atom. Examples of the hetero atom in the aromatic hetero rings include an oxygen atom, a sulfur atom and a nitrogen atom.

Examples of the aromatic hydrocarbon group include a group in which one hydrogen atom is removed from the aforementioned aromatic hydrocarbon ring (aryl group); and a group in which one hydrogen atom of the aforementioned aryl group is substituted with an alkylene group (an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain in the arylalkyl group) preferably has 1 to 4 carbon atoms, more preferably 1 or 2, and most preferably 1.

In the case where $Ra'^3$ is bonded to $Ra'^1$ or $Ra'^2$ to form a ring, the cyclic group is preferably a 4- to 7-membered ring, and more preferably a 4- to 6-membered ring. Examples of the cyclic group include a tetrahydropyranyl group and a tetrahydrofuranyl group.

Examples of the acid dissociable group for protecting the carboxy group as a polar group include the acid dissociable group represented by general formula (a1-r-2) shown below (hereafter, with respect to the acid dissociable group represented by the following formula (a1-r-2), the acid dissociable group constituted of alkyl groups is referred to as "tertiary alkyl ester-type acid dissociable group").

[Chemical formula 37]

(a1-r-2)

In general formula (a1-r-2), $Ra'^4$ to $Ra'^6$ each independently represent a hydrocarbon group, provided that $Ra'^5$ and $Ra'^6$ may be mutually bonded to form a ring. "*" represents a valence bond.

As the hydrocarbon group for $Ra'^4$ to $Ra'^6$, the same groups as those described above for $Ra'^3$ can be mentioned. $Ra'^4$ is preferably an alkyl group having 1 to 5 carbon atoms. In the case where $Ra'^5$ and $Ra'^6$ are mutually bonded to form a ring, a group represented by general formula (a1-r2-1) shown below can be mentioned.

On the other hand, in the case where $Ra'^4$ to $Ra'^6$ are not mutually bonded and independently represent a hydrocarbon group, the group represented by general formula (a1-r2-2) shown below can be mentioned.

[Chemical formula 38]

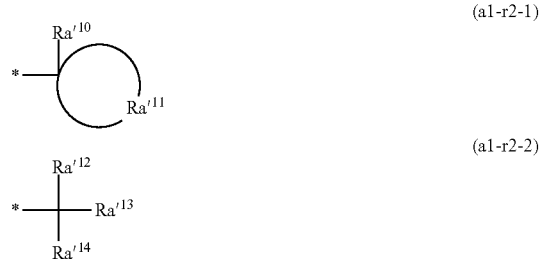

In general formula (a1-r2-1) or (a1-r2-2), $Ra'^{10}$ represents an alkyl group having 1 to 10 carbon atoms; $Ra'^{11}$ is a group which forms an aliphatic cyclic group together with a carbon atom having $Ra'^{10}$ bonded thereto; and $Ra'^{12}$ to $Ra'^{14}$ each independently represent a hydrocarbon group. "*" represents a valence bond.

In the formula (a1-r2-1), as the alkyl group having 1 to 10 carbon atoms for $Ra'^{10}$, the same groups as described above for the linear or branched alkyl group for $Ra'^3$ in the formula (a1-r-1) are preferable. In the formula (a1-r-1), as the aliphatic cyclic group which is formed by $Ra'^{11}$, the same groups as those described above for the cyclic alkyl group for $Ra'^3$ in the formula (a1-r-1) are preferable.

In the formula (a1-r2-2), it is preferable that $Ra'^{12}$ and $Ra'^{14}$ each independently represent an alkyl group having 1 to 10 carbon atoms, and it is more preferable that the alkyl group is the same group as described above for the linear or branched alkyl group for $Ra'^3$ in the formula (a1-r-1), it is still more preferable that the alkyl group is a linear alkyl group having 1 to 5 carbon atoms, and it is particularly preferable that the alkyl group is a methyl group or an ethyl group.

In the formula (a1-r2-2), it is preferable that $Ra'^{13}$ is the same group as described above for the linear, branched or cyclic alkyl group as the hydrocarbon group for $Ra'^3$ in the formula (a1-r-1). Among these, the same cyclic alkyl group as those describe above for $Ra'^3$ is more preferable.

Examples of the formula (a1-r2-1) are shown below. In the formulae shown below, "*" represents a valence bond.

[Chemical formula 39]

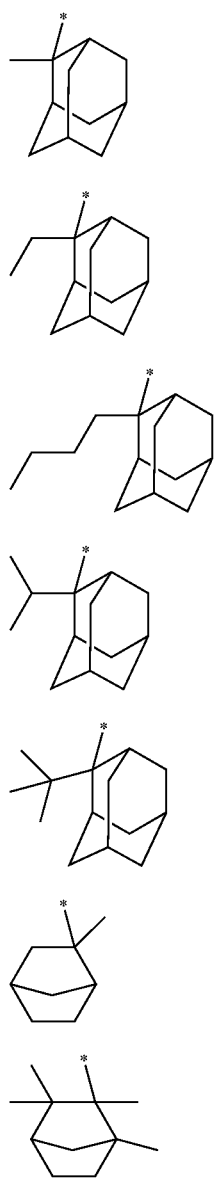

(r-pr-m1)

(r-pr-m2)

(r-pr-m3)

(r-pr-m4)

(r-pr-m5)

(r-pr-m6)

(r-pr-m7)

-continued

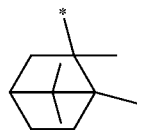

(r-pr-m8)

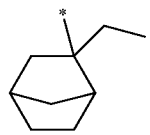

(r-pr-m9)

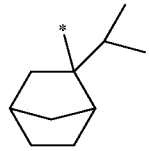

(r-pr-m10)

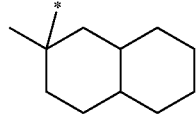

(r-pr-m11)

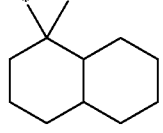

(r-pr-m12)

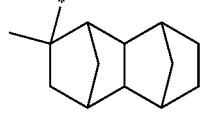

(r-pr-m13)

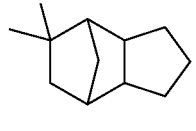

(r-pr-m14)

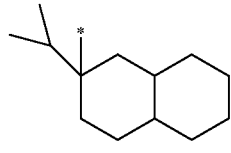

(r-pr-m15)

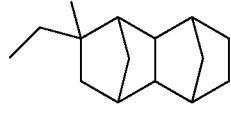

(r-pr-m16)

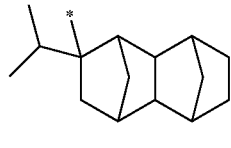

(r-pr-m17)

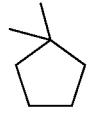

(r-pr-s1)

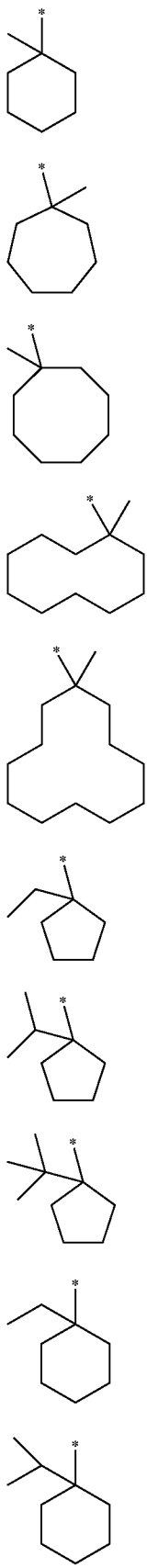
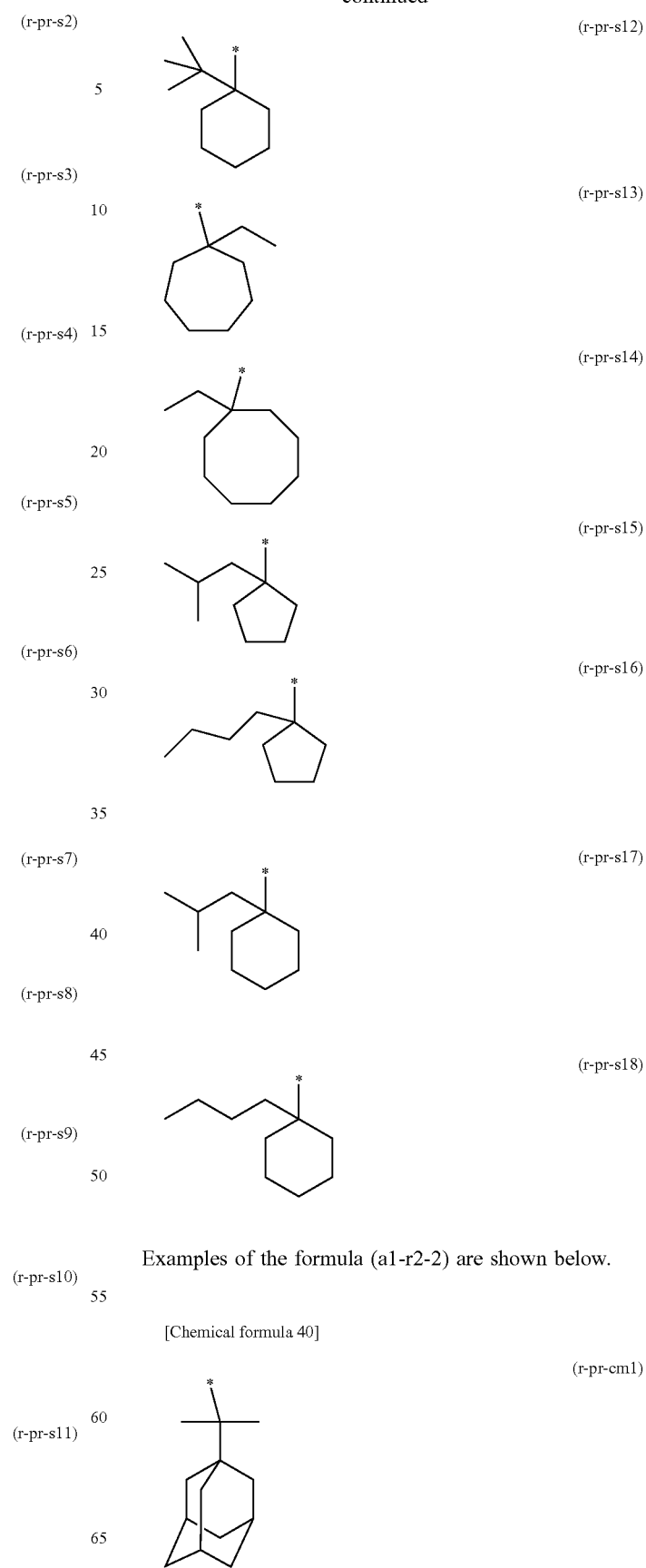
Examples of the formula (a1-r2-2) are shown below.
[Chemical formula 40]
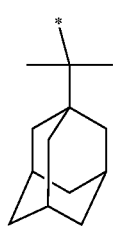
(r-pr-cm1)

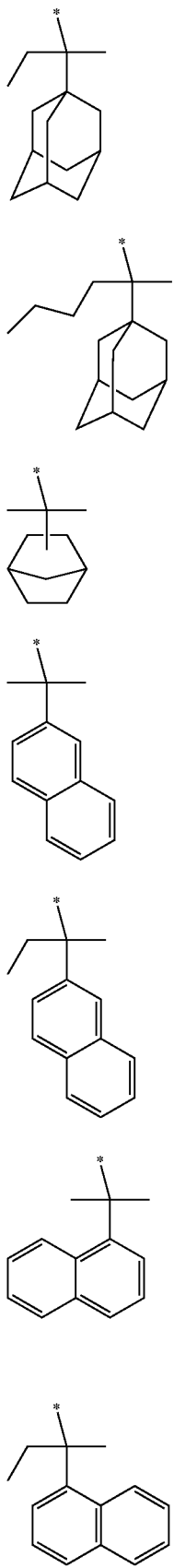
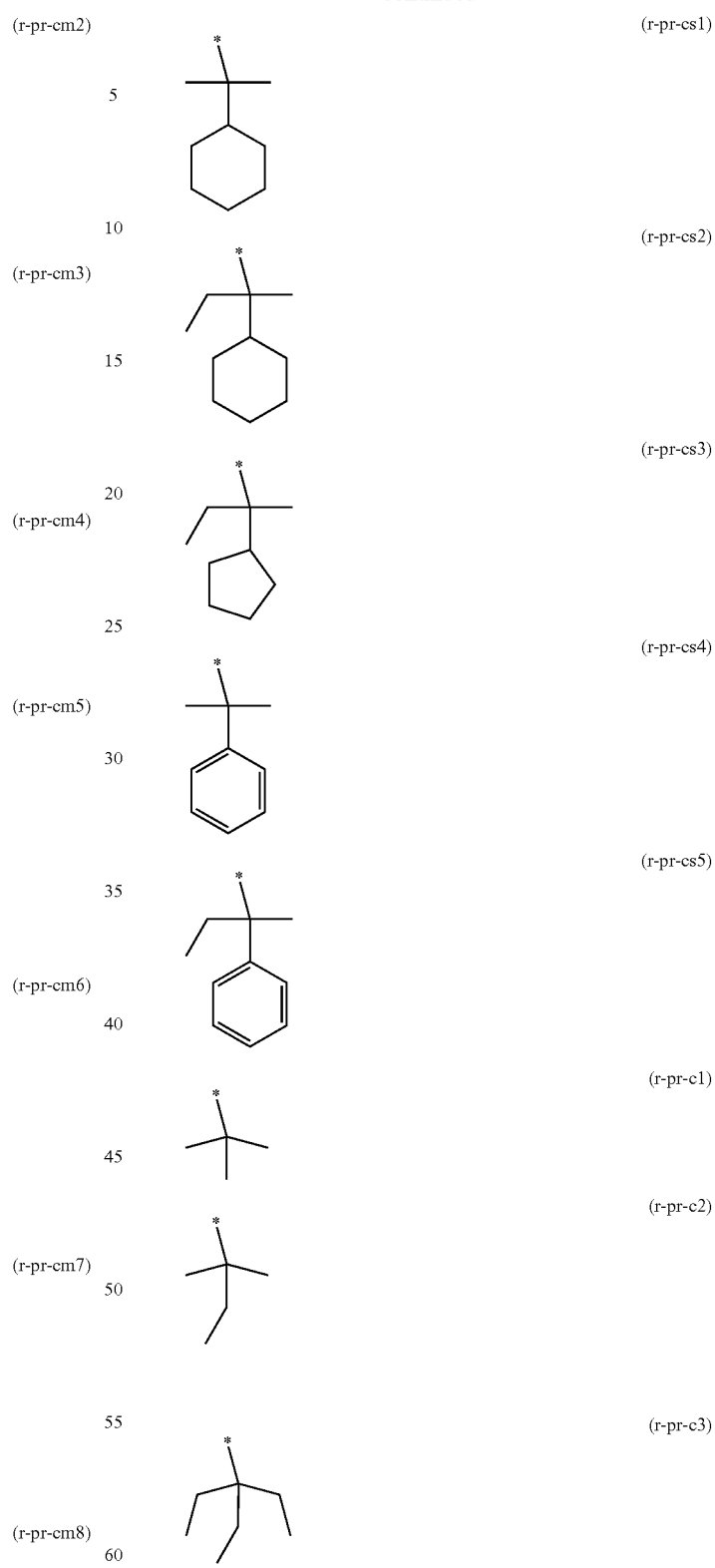
Examples of the acid dissociable group for protecting a hydroxyl group as a polar group include the acid dissociable group represented by general formula (a1-r-3) shown below (hereafter, referred to as "tertiary alkyloxycarbonyl-type acid dissociable group").

[Chemical formula 41]

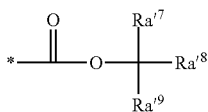

(a1-r-3)

In general formula (a1-r-3), $Ra'^7$ to $Ra'^9$ each independently represent an alkyl group. "*" represents a valence bond.

In the formula (a1-r-3), $Ra'^7$ to $Ra'^9$ are preferably an alkyl group having 1 to 5 carbon atoms, and more preferably an alkyl group having 1 to 3 carbon atoms.

Further, the total number of carbon atoms in the alkyl group is preferably 3 to 7, more preferably 3 to 5, and most preferably 3 or 4.

Examples of the structural unit (a1) include a structural unit derived from an acrylic ester in which the hydrogen atom bonded to the carbon atom on the α-position may be substituted with a substituent and which contains an acid decomposable group which exhibits increased polarity by the action of an acid; a structural unit derived from hydroxystyrene or a hydroxystyrene derivative in which at least a part of the hydrogen atom of the hydroxyl group is protected with a substituent containing an acid decomposable group; and a structural unit derived from vinylbenzoic acid or a vinylbenzoic acid derivative in which at least a part of the hydrogen atom in —C(=O)—OH is protected with a substituent containing an acid decomposable group.

As the structural unit (a1), among the above, a structural unit derived from acrylic ester, in which a hydrogen atom bonded to the carbon atom on the α-position may be substituted with a substituent, is preferable.

As the structural unit (a1), a structural unit represented by the following general formula (a1-1) or (a1-2) is preferable.

[Chemical formula 42]

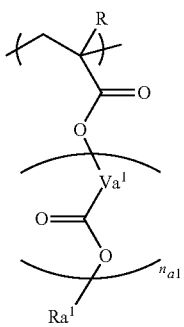

(a1-1)

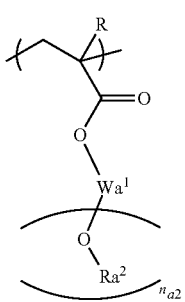

(a1-2)

In general formula (a1-1) or (a1-2), R represents a hydrogen atom, an alkyl group having 1 to 5 carbon atoms, or a halogenated alkyl group having 1 to 5 carbon atoms. $Va^1$ represents a divalent hydrocarbon group which may have an ether bond, a urethane bond, or an amide bond, $n_{a1}$ is 0 to 2, and $Ra^1$ represents an acid dissociable group represented by general formulae (a1-r-1) and (a1-r-2). $Wa^1$ represents a hydrocarbon group having a valence of $n_{a2}+1$, $n_{a2}$ is 1 to 3, and $Ra^2$ represents an acid dissociable group represented by general formula (a1-r-1) or (a1-r-3).

In general formula (a1-1), the alkyl group having 1 to 5 carbon atoms is preferably a linear or branched alkyl group having 1 to 5 carbon atoms, and examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group in which a part or all of the hydrogen atoms of the alkyl group having 1 to 5 carbon atoms is substituted with a halogen atom. Examples of the halogen atom include a fluorine atom, a chlorine atom, a bromine atom, and an iodine atom, and a fluorine atom is particularly preferable.

As for R, a hydrogen atom, an alkyl group having 1 to 5 carbon atoms, or a fluorinated alkyl group having 1 to 5 carbon atoms is preferable, from a viewpoint of easy industrial availability, and a hydrogen atom or a methyl group is most preferable.

The hydrocarbon group for $Va^1$ may be an aliphatic hydrocarbon group or an aromatic hydrocarbon group. The aliphatic hydrocarbon group means a hydrocarbon group having no aromaticity. The aliphatic hydrocarbon group for $Va^1$ as a divalent hydrocarbon group may be saturated or unsaturated and, normally, the saturated aliphatic hydrocarbon group is preferable.

Examples of the aliphatic hydrocarbon group include a linear or branched aliphatic hydrocarbon group and an aliphatic hydrocarbon group having a ring in the structure.

Also, examples of $Va^1$ include a group in which the divalent hydrocarbon group is bonded via an ether bond, a urethane bond, or an amide bond.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable, and examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

As the branched aliphatic hydrocarbon group, a branched alkylene group is preferable, and examples thereof include an alkylalkylene group including an alkylmethylene group such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, and —C($CH_2CH_3$)$_2$—; an alkylethylene group such as —CH($CH_3$)$CH_2$—, —CH($CH_3$)CH($CH_3$)—, —C($CH_3$)$_2CH_2$—, —CH($CH_2CH_3$)$CH_2$—, and —C($CH_2CH_3$)$_2$—$CH_2$—; an alkyltrimethylene group such as —CH($CH_3$)$CH_2CH_2$— and —$CH_2$CH($CH_3$)$CH_2$—; and an alkyltetramethylene group such as —CH($CH_3$)$CH_2CH_2CH_2$— and —$CH_2$CH($CH_3$)$CH_2CH_2$—. The alkyl group in the alkylalkylene group is preferably an alkyl group having 1 to 5 carbon atoms.

As examples of the aliphatic hydrocarbon group containing a ring in the structure thereof, an alicyclic hydrocarbon group (a group in which two hydrogen atoms are removed from an aliphatic hydrocarbon ring), a group in which the alicyclic hydrocarbon group is bonded to the terminal of the aforementioned linear or branched aliphatic hydrocarbon group, and a group in which the alicyclic hydrocarbon group is interposed within the aforementioned linear or branched aliphatic hydrocarbon group, can be given. As the linear or branched aliphatic hydrocarbon group, the same groups as those described above can be used.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which two hydrogen atoms are removed from a monocycloalkane is preferable. The monocycloalkane preferably has 3 to 6 carbon atoms, and examples thereof include cyclopentane and cyclohexane. As the polycyclic aliphatic hydrocarbon group, a group in which two hydrogen atoms are removed from a polycycloalkane is preferable, and the polycycloalkane group preferably has 7 to 12 carbon atoms. Examples of the polycycloalkane include adamantane, norbornane, isobornane, tricyclodecane and tetracyclododecane.

The aromatic hydrocarbon group is a hydrocarbon group having an aromatic ring.

The aromatic hydrocarbon group as the divalent hydrocarbon group for $Va^1$ preferably has 3 to 30 carbon atoms, more preferably 5 to 30, still more preferably 5 to 20, still more preferably 6 to 15, and most preferably 6 to 10. Here, the number of carbon atoms present in a substituent(s) is not included in the number of carbon atoms of the aromatic hydrocarbon group.

Examples of the aromatic ring contained in the aromatic hydrocarbon group include an aromatic hydrocarbon ring, such as benzene, biphenyl, fluorene, naphthalene, anthracene and phenanthrene; and an aromatic hetero ring in which part of the carbon atoms constituting the aforementioned aromatic hydrocarbon ring is substituted with a hetero atom. Examples of the hetero atom present in the aromatic hetero ring include an oxygen atom, a sulfur atom and a nitrogen atom.

Examples of the aromatic hydrocarbon group include a group in which two hydrogen atoms are removed from the aromatic hydrocarbon ring (arylene group); a group obtained by substituting one hydrogen atom on a group (aryl group) in which one hydrogen atom is removed from the aromatic hydrocarbon ring with an alkylene group (a group obtained by removing one hydrogen atom from an ary moeity in an arylalkyl group such as a benzyl group, a phenethyl group, a 1-naphthylmethyl group, a 2-naphthylmethyl group, a 1-naphthylethyl group, or a 2-naphthylethyl group). The alkylene group (alkyl chain in the arylalkyl group) preferably has 1 to 4 carbon atom, more preferably 1 or 2, and most preferably 1.

In the aforementioned formula (a1-2), the hydrocarbon group for $Wa^1$ having a valence of $n_{a2}+1$ may be either an aliphatic hydrocarbon group or an aromatic hydrocarbon group. The aliphatic hydrocarbon group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. As the examples thereof, the same groups as those described above for $Va^1$ in the aforementioned formula (a1-1) can be mentioned.

The valence of $n_{a2}+1$ is preferably divalent, trivalent or tetravalent, more preferably divalent or trivalent.

As the structural unit (a1-2), a structural unit represented by general formula (a1-2-01) shown below is particularly preferable.

[Chemical formula 43]

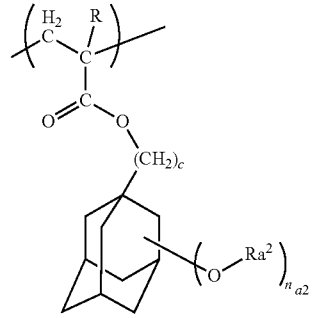

(a1-2-01)

In the formula (a1-2-01), $Ra^2$ represents an acid dissociable group represented by the aforementioned formula (a1-r-1) or (a1-r-3); $n_{a2}$ represents an integer of 1 to 3, preferably 1 or 2, and more preferably 1; c represents an integer of 0 to 3, preferably 0 or 1, and more preferably 1. R is the same as defined above.

Examples of the structural units (a1-1) and (a1-2) are shown below. In the formulae shown below, $R^\alpha$ represents a hydrogen atom, a methyl group or a trifluoromethyl group.

[Chemical formula 44]

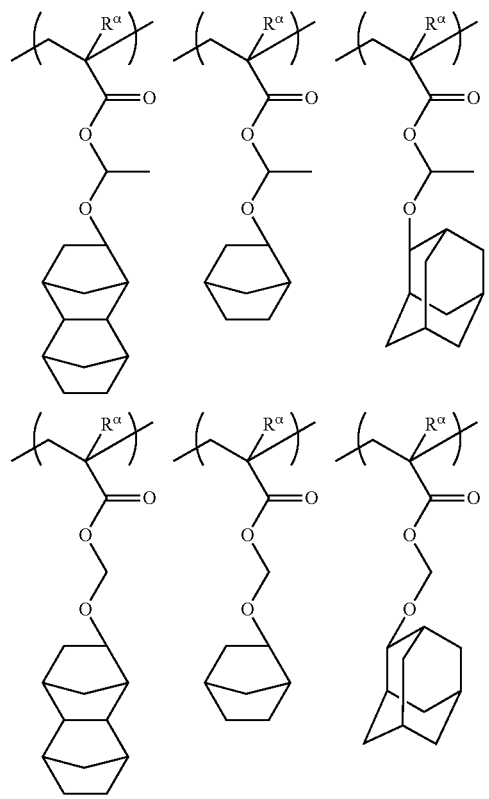

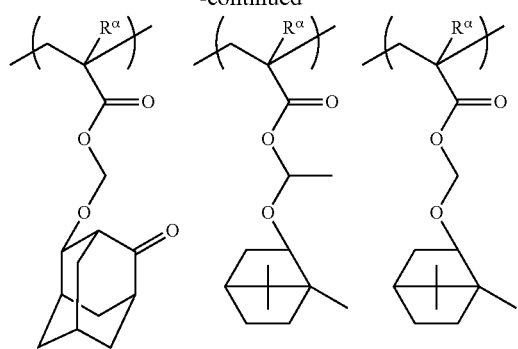
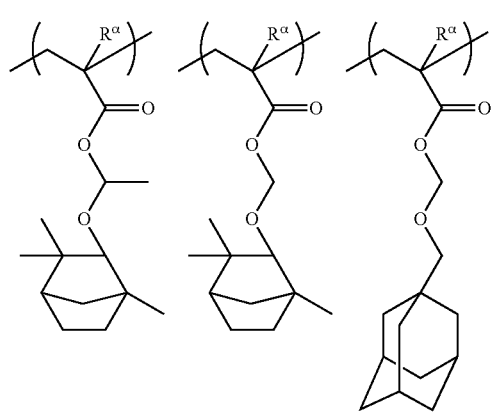
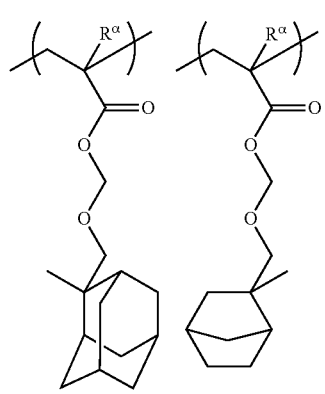
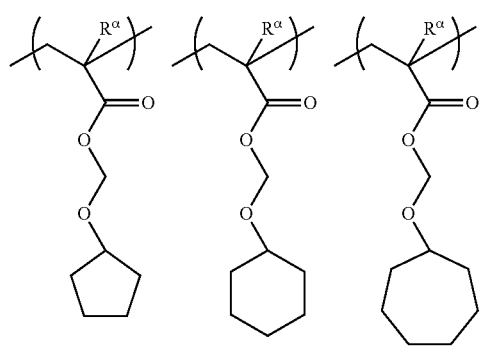
[Chemical formula 45]
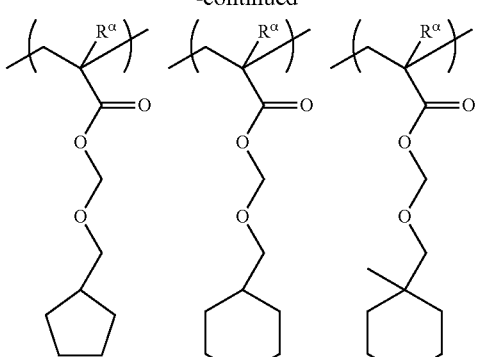
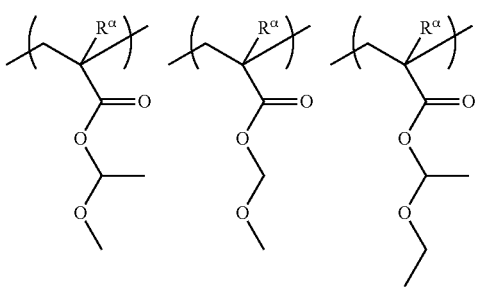
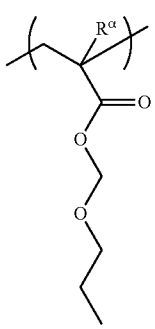
[Chemical formula 46]
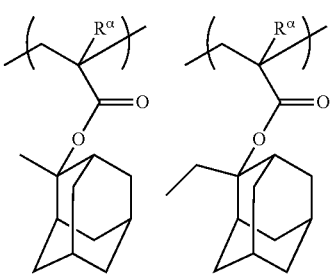
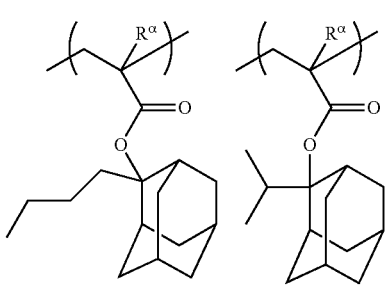

-continued
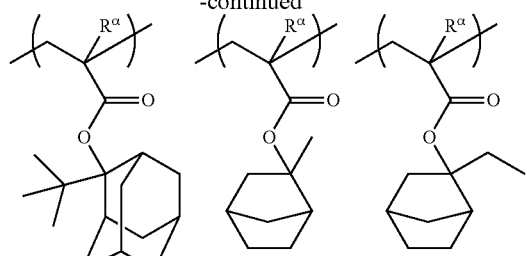
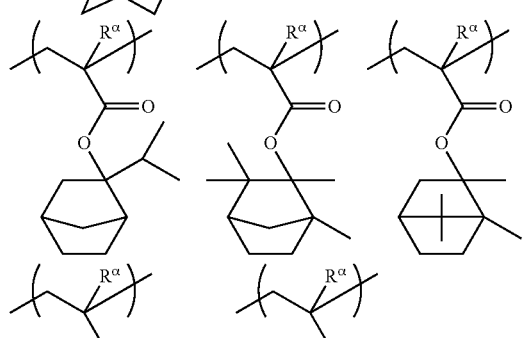
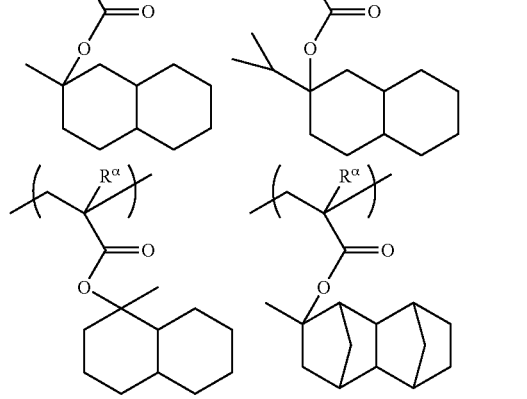
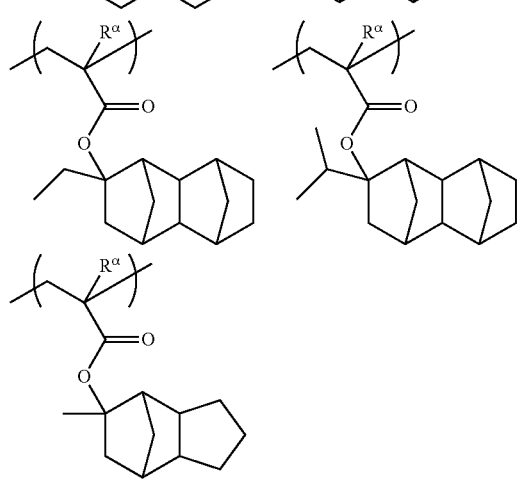
[Chemical formula 47]
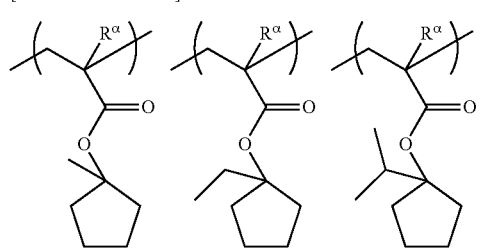
-continued
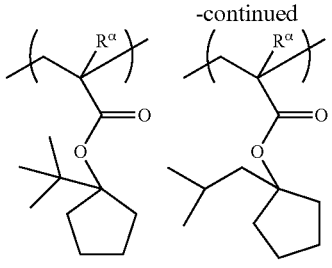
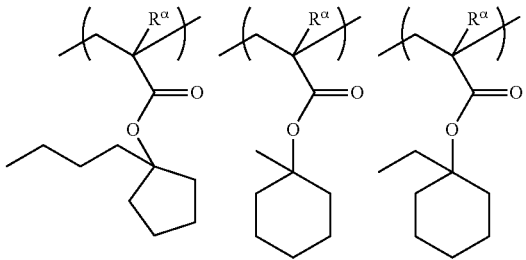
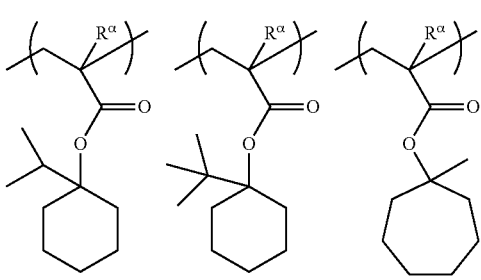
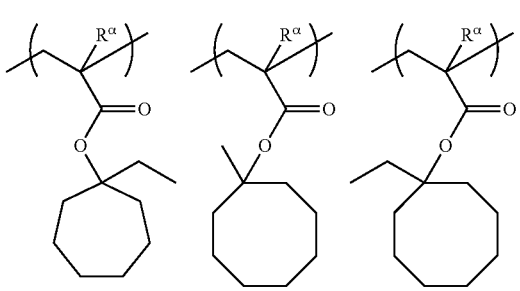
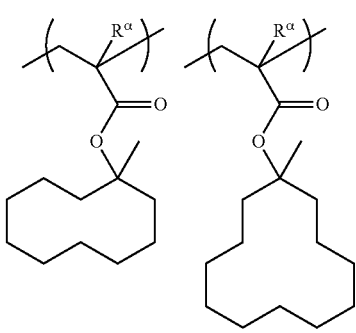

[Chemical formula 48]

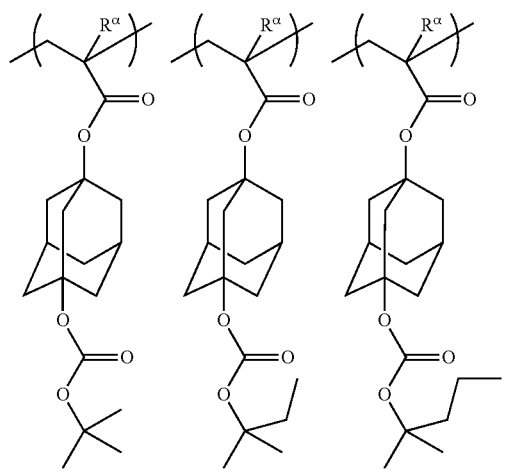
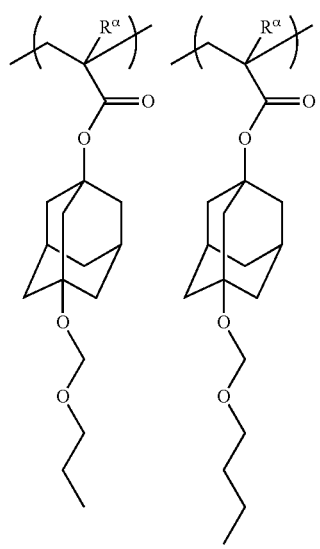
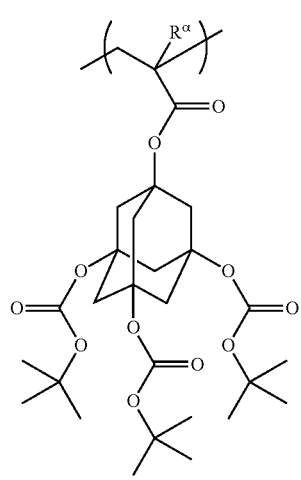
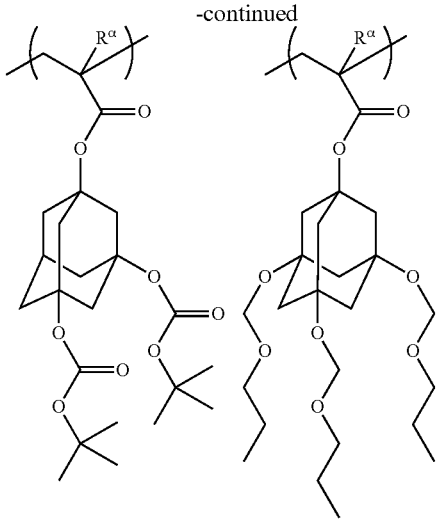
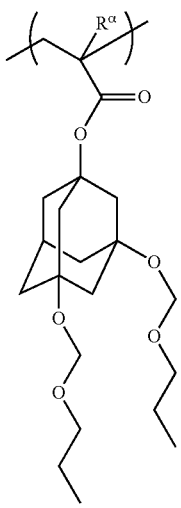

The type of the structural unit (a1) included in the component (A1) may be one or two or more.

The ratio of the structural unit (a1) in the component (A1) is preferably 20 mol % to 80 mol %, more preferably 20 mol % to 75 mol %, and still more preferably 25 mol % to 70 mol % with respect to all of the structural units configuring the component (A1). If the ratio is set to the lower limit or more, lithography properties such as sensitivity, resolution, and LWR are improved. Also, if the ratio is set to the upper limit or less, a good balance can be easily achieved with the other structural units.

Structural Unit (a12)

The structural unit (a12) is a structural unit which includes an acid decomposable group whose polarity increases under the action of an acid, and is a structural unit represented by the following general formula (a12-1).

[Chemical formula 49]

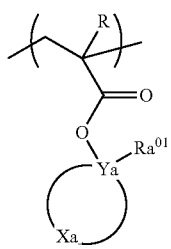

(a12-1)

In general formula (a12-1), R represents a hydrogen atom, an alkyl group having 1 to 5 carbon atoms, or a halogenated alkyl group having 1 to 5 carbon atoms. Ya represents a carbon atom. Xa is an atomic group necessary for forming an alicyclic hydrocarbon group along with Ya. $Ra^{01}$ represents an aromatic hydrocarbon group which may have a substituent.

R

In general formula (a12-1), the alkyl group having 1 to 5 carbon atoms for R is preferably a linear or branched alkyl group having 1 to 5 carbon atoms, and examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group in which a part or all of the hydrogen atoms of the alkyl group having 1 to 5 carbon atoms is substituted with a halogen atom. Examples of the halogen atom include a fluorine atom, a chlorine atom, a bromine atom, and an iodine atom, and a fluorine atom is particularly preferable.

As for R, a hydrogen atom, an alkyl group having 1 to 5 carbon atoms, or a fluorinated alkyl group having 1 to 5 carbon atoms is preferable, from a viewpoint of easy industrial availability, and a hydrogen atom or a methyl group is most preferable.

Xa

In general formula (a12-1), the carbon number of the alicyclic hydrocarbon group formed by Xa along with Ya is not particularly limited, and the carbon number is preferably 5 to 25, more preferably 5 to 20, and still more preferably 5 to 15.

In addition, this alicyclic hydrocarbon group may be monocyclic or polycyclic. Examples of the structure of the aliphatic moiety include the structure represented by any one of the following formulae (Xa-1) to (Xa-50).

[Chemical formula 50]

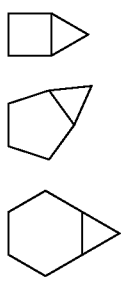

(Xa-1)

(Xa-2)

(Xa-3)

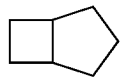

(Xa-4)

(Xa-5)

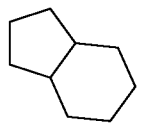

(Xa-6)

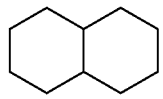

(Xa-7)

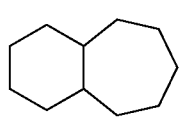

(Xa-8)

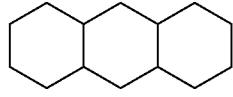

(Xa-9)

[Chemical formula 51]

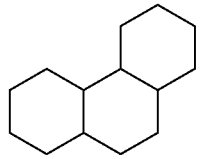

(Xa-10)

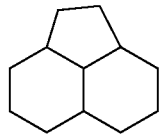

(Xa-11)

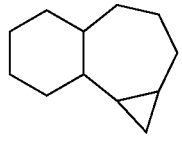

(Xa-12)

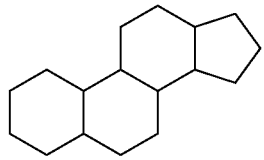

(Xa-13)

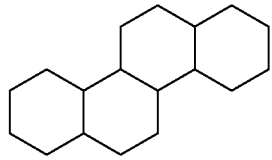

(Xa-14)

-continued
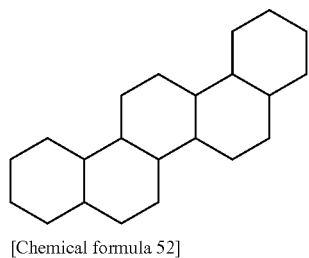
[Chemical formula 52]
(Xa-15) 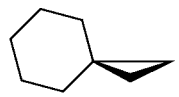
(Xa-16) 
(Xa-17) 
(Xa-18) 
(Xa-19) 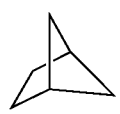
(Xa-20) 
(Xa-21) 
(Xa-22) 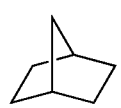
(Xa-23) 
(Xa-24) 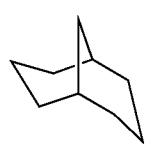
(Xa-25) 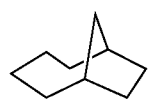
-continued
(Xa-26) 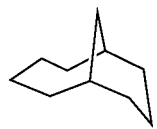
[Chemical formula 53]
(Xa-27) 
(Xa-28) 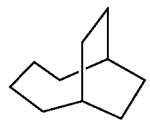
(Xa-29) 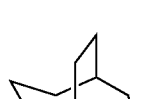
(Xa-30) 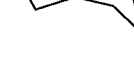
(Xa-31) 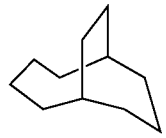
(Xa-32) 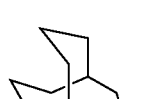
(Xa-33) 
(Xa-34) 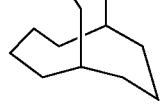
(Xa-35) 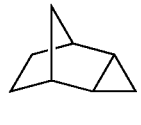
[Chemical formula 54]
(Xa-36) 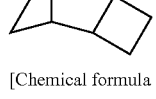
(Xa-37) 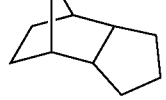

(Xa-38) 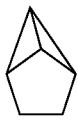

(Xa-39) 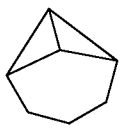

(Xa-40) 

(Xa-41) 

(Xa-42) 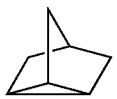

(Xa-43) 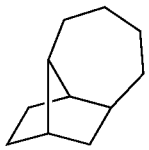

(Xa-44) 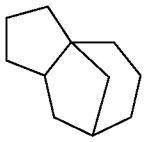

(Xa-45) 

(Xa-46) 

[Chemical formula 55]

(Xa-47) 

(Xa-48) 

(Xa-49) 

(Xa-50) 

The alicyclic hydrocarbon group formed by Xa along with Ya in general formula (a12-1) is particularly preferably a group having a monocyclo, a bicyclo, a tricyclo or a tetracyclo structure.

Examples of the alicyclic hydrocarbon group include a cycloalkyl group such as a cyclopentyl group, a cyclohexyl group, a cycloheptyl group, a cyclooctyl group, a cyclodecanyl group, and a cyclododecanyl group; an adamantyl group, a noradamantyl group, a decalin residue (a decanyl group), a tricyclodecanyl group, a tetracyclododecanyl group, a norbornyl group, and a cedrol group.

Among these, a cycloalkyl group such as a cyclopentyl group, a cyclohexyl group, a cycloheptyl group, a cyclooctyl group, a cyclodecanyl group, and a cyclododecanyl group; an adamantyl group, a decalin residue, or a norbornyl group is preferable. A cycloalkyl group having 5 to 15 carbon atoms is particularly preferable.

In addition, the alicyclic hydrocarbon group may be substituted or unsubstituted. Examples of the substituent include a methyl group, an ethyl group, a propyl group, a hydroxyl group, a carboxy group, a halogen atom (a fluorine atom, a bromine atom, or the like), an alkoxy group (a methoxy group, an ethoxy group, a propoxy group, a butoxy group, or the like), and an alkyloxycarbonyl group.

$Ra^{01}$

Examples of the aromatic hydrocarbon group which may have a substituent for $Ra^{01}$ include the group derived from the structure represented by any one of the following formulae ($Ra^{01}$-1) to ($Ra^{01}$-3).

In addition, in the case where $Ra^{01}$ is a group derived from the following ($Ra^{01}$-2) (that is, a naphthyl group), a bonding position bonded to Ya of general formula (a12-1) may be either the 1st position or 2nd position.

In addition, in the case where $Ra^{01}$ is a group derived from the following ($Ra^{01}$-3) (that is, an anthryl group), a bonding position bonded to Ya of general formula (a12-1) may be any one of the 1st position, the 2nd position and the 9th position.

In addition, the aryl group may have a substituent. Examples of the substituent include a methyl group, an ethyl group, a propyl group, a hydroxyl group, a carboxy group, a halogen atom (a fluorine atom, a chlorine atom, a bromine atom, or the like), an alkoxy group (a methoxy group, an ethoxy group, a propoxy group, a butoxy group, or the like), and an alkyloxycarbonyl group.

[Chemical formula 56]

($Ra^{01}$-1) 

($Ra^{01}$-2) 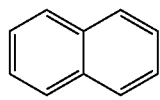

[Chemical formula 57]

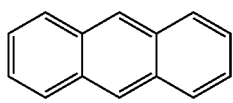

(Ra01-3)

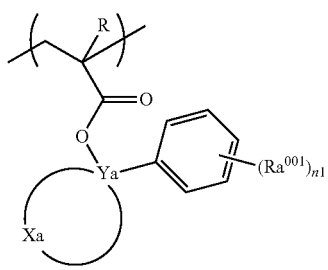

(a12-1-1)

In general formula (a12-1-1), R represents a hydrogen atom, an alkyl group having 1 to 5 carbon atoms, or a halogenated alkyl group having 1 to 5 carbon atoms, $Ra^{001}$ represents an alkyl group having 1 to 4 carbon atoms, Ya represents a carbon atom, Xa is an atomic group necessary for forming an alicyclic hydrocarbon group along with Ya, and n1 represents an integer of 0 to 3.

Examples of the alkyl group having 1 to 4 carbon atoms for $Ra^{001}$ of general formula (a12-1-1) include a methyl group, an ethyl group, an n-propyl group, an i-propyl group, an n-butyl group, a 2-methylpropyl group, a 1-methylpropyl group, and a t-butyl group.

In addition, n1 of general formula (a12-1-1) represents an integer of 0 to 3, and more preferably 0 or 1.

As to the "alicyclic hydrocarbon group formed by Xa along with Ya" of general formula (a12-1-1), the description for the "alicyclic hydrocarbon group formed by Xa along with Ya" of general formula (a12-1) can be applied thereto as it is.

Hereinafter, examples of the structural unit (a12) will be shown. In the following formulae, R represents a hydrogen atom, an alkyl group having 1 to 5 carbon atoms, or a halogenated alkyl group having 1 to 5 carbon atoms.

[Chemical formula 58]

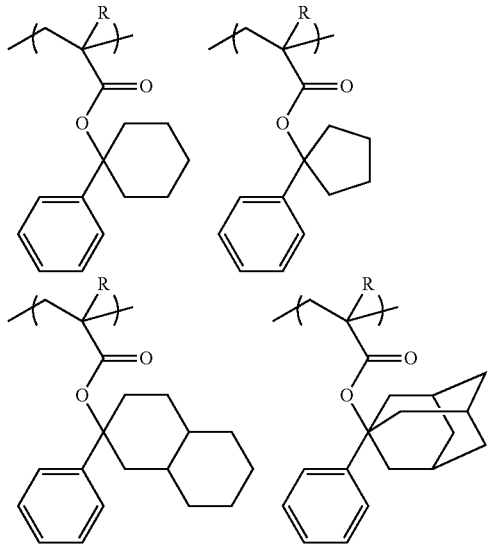

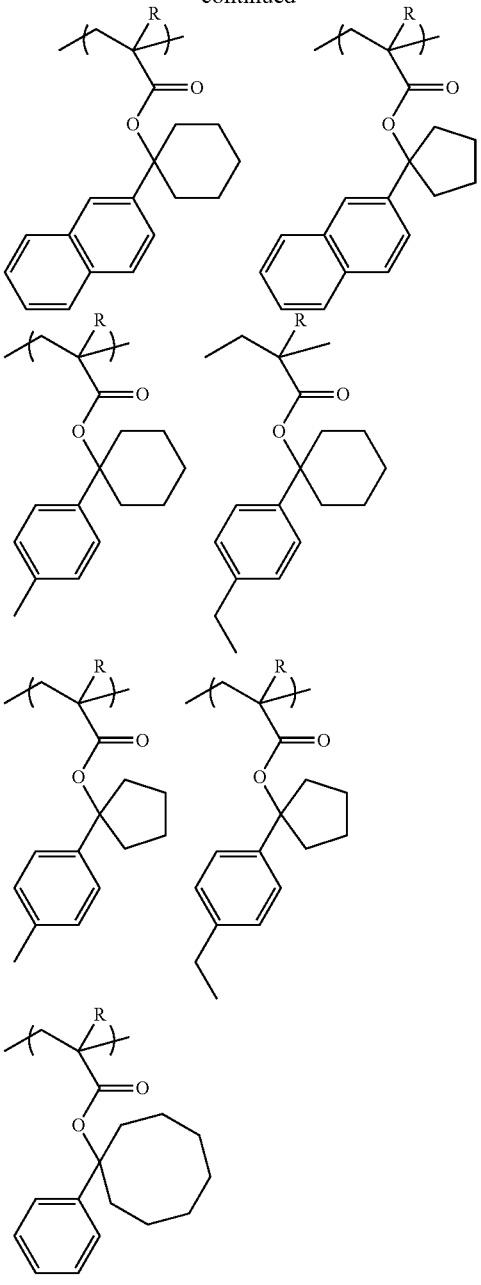

The type of the structural unit (a12) included in the component (A1) may be one or two or more.

The ratio of the structural unit (a12) of the component (A1) is preferably 50 mol % to 80 mol %, more preferably 10 mol % to 75 mol %, and still more preferably 10 mol % to 70 mol % with respect to all of structural units configuring the component (A1). If the ratio is set to the lower limit or more, lithography properties such as sensitivity, resolution, and LWR are improved, and if the ratio is set to the upper limit or less, a good balance can be easily achieved with the other structural units.

Structural Unit (a2)

The structural unit (a2) is a structural unit having a —$SO_2$-containing cyclic group, a lactone-containing cyclic group, a carbonate-containing cyclic group, or a heterocyclic group other than these.

The —SO$_2$-containing cyclic group, the lactone-containing cyclic group, the carbonate-containing cyclic group, or the heterocyclic group other than these of the structural unit (a2) is effective for increasing adhesiveness of the resist film to the substrate, in the case where the component (A1) is used for forming a resist film.

In addition, in the case where the aforementioned structural unit (a1) includes the —SO$_2$-containing cyclic group, the lactone-containing cyclic group, the carbonate-containing cyclic group, or the heterocyclic group other than these in its structure, the structural unit falls under the definition of the structural unit (a2) as well; however, such a structural unit is regarded as a structural unit (a1), and does not fall under the definition of the structural unit (a2).

The structural unit (a2) is preferably a structural unit represented by the following general formula (a2-1).

[Chemical formula 59]

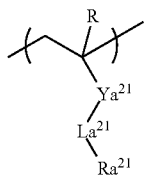

(a2-1)

In general formula (a2-1), R represents a hydrogen atom, an alkyl group having 1 to 5 carbon atoms, or a halogenated alkyl group having 1 to 5 carbon atoms, $Ya^{21}$ represents a single bond or a divalent linking group, $La^{21}$ represents —O—, —COO—, —CON(R')—, —OCO—, —CONHCO—, or —CONHCS—, and R' represents a hydrogen atom or a methyl group. However, in the case where $La^{21}$ represents —O—, $Ya^{21}$ cannot be —CO—. $Ra^{21}$ represents a —SO$_2$-containing cyclic group, a lactone-containing cyclic group, a carbonate-containing cyclic group or a heterocyclic group other than these.

The divalent linking group for $Ya^{21}$ is not particularly limited, and preferred examples thereof include a divalent hydrocarbon group which may have a substituent, and a divalent linking group which may have a hetero atom.

Divalent Hydrocarbon Group which May have a Substituent

The hydrocarbon group as a divalent linking group may be either an aliphatic hydrocarbon group or an aromatic hydrocarbon group.

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof. Specifically, groups exemplified above for $Va^1$ in the aforementioned formula (a1-1) can be mentioned.

The linear or branched aliphatic hydrocarbon group may or may not have a substituent. Examples of the substituent include a fluorine atom, a fluorinated alkyl group having 1 to 5 carbon atoms, and a carbonyl group.

As examples of the aliphatic hydrocarbon group containing a ring in the structure thereof, a cyclic aliphatic hydrocarbon group containing a hetero atom in the ring structure thereof and may have a substituent (a group in which two hydrogen atoms are removed from an aliphatic hydrocarbon ring), a group in which the cyclic aliphatic hydrocarbon group is bonded to the terminal of the aforementioned linear or branched aliphatic hydrocarbon group, and a group in which the cyclic aliphatic hydrocarbon group is interposed within the aforementioned linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

Examples of the cyclic aliphatic hydrocarbon group include the same group as exemplified above for $Va^1$ in the aforementioned formula (a1-1).

The cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group having 1 to 5 carbon atoms, and a methyl group, an ethyl group, a propyl group, an n-butyl group or a tert-butyl group is particularly preferable.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent include a fluorine atom, a chlorine atom, a bromine atom and an iodine atom, and a fluorine atom is preferable.

Examples of the halogenated alkyl group for the substituent include a group in which part or all of the hydrogen atoms present in the aforementioned alkyl group is substituted with the aforementioned halogen atoms.

The cyclic aliphatic hydrocarbon group may be a group in which part of the carbon atoms constituting the ring structure of the cyclic aliphatic hydrocarbon group may be substituted with a substituent containing a hetero atom.

As the substituent containing a hetero atom, —O—, —C(=O)—O—, —S—, —S(=O)$_2$— or —S(=O)$_2$—O— is preferable.

Examples of the aromatic hydrocarbon group as a divalent hydrocarbon group include the same group as exemplified above for $Va^1$ in the aforementioned formula (a1-1).

With respect to the aromatic hydrocarbon group, the hydrogen atom in the aromatic hydrocarbon group may be substituted with a substituent. For example, the hydrogen atom bonded to the aromatic ring in the aromatic hydrocarbon group may be substituted with a substituent. Examples of the substituent include an alkyl group, an alkoxy group, a halogen atom, a halogenated alkyl group, and a hydroxyl group.

The alkyl group as the substituent is preferably an alkyl group having 1 to 5 carbon atoms, particularly preferably a methyl group, an ethyl group, a propyl group, an n-butyl group or a tert-butyl group.

As the alkoxy group, the halogen atom and the halogenated alkyl group for the substituent, the same groups as the aforementioned substituents for substituting a hydrogen atom in the cyclic aliphatic hydrocarbon group can be exemplified.

Divalent Linking Group Containing a Hetero Atom

With respect to a divalent linking group containing a hetero atom, a hetero atom is an atom other than carbon and hydrogen, and examples thereof include an oxygen atom, a nitrogen atom, a sulfur atom and a halogen atom.

In the case where Ya$^{21}$ represents a divalent linking group containing a hetero atom, preferable examples of the linking group include —O—, —C(=O)—O—, —C(=O)—, —O—C(=O)—O—, —C(=O)—NH—, —NH—, —NH—C(=NH)— (where H may be substituted with a substituent such as an alkyl group or an acyl group), —S—, —S(=O)$_2$—, —S(=O)$_2$—O—, and a group represented by general formula —Y$^{21}$—O—Y$^{22}$—, —Y$^{21}$—O—, —Y$^{21}$—C(=O)—O—, —C(=O)—O—Y$^{21}$, —[Y$^{21}$—C(=O)—O]$_{m'}$—Y$^{22}$— or —Y$^{21}$—O—C(=O)—Y$^{22}$— (in the formulae, Y$^{21}$ and Y$^{22}$ each independently represent a divalent hydrocarbon group which may have a substituent, and O represents an oxygen atom; and m' represents an integer of 0 to 3).

In the case where the divalent linking group containing a hetero atom represents —C(=O)—NH—, —NH—, or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In the formulae —Y$^{21}$—O—Y$^{22}$—, —Y$^{21}$—O—, —Y$^{21}$—C(=O)—O—, —C(=O)—O—Y$^{21}$, —[Y$^{21}$—C(=O)—O]$_{m'}$—Y$^{22}$— and —Y$^{21}$—O—C(=O)—Y$^{22}$—, Y$^{21}$ and Y$^{22}$ each independently represent a divalent hydrocarbon group which may have a substituent. Examples of the divalent hydrocarbon group include the same groups as those described above as the "divalent hydrocarbon group which may have a substituent" in the description of the aforementioned divalent linking group.

As Y$^{21}$, a linear aliphatic hydrocarbon group is preferable, a linear alkylene group is more preferable, a linear alkylene group having 1 to 5 carbon atoms is still more preferable, and a methylene group or an ethylene group is particularly preferable.

As Y$^{22}$, a linear or branched aliphatic hydrocarbon group is preferable, and a methylene group, an ethylene group or an alkylmethylene group is more preferable. The alkyl group in the alkylmethylene group is preferably a linear alkyl group having 1 to 5 carbon atoms, more preferably a linear alkyl group having 1 to 3 carbon atoms, and most preferably a methyl group.

In the group represented by the formula [Y$^{21}$—C(=O)—O]$_{m'}$—Y$^{22}$—, m' represents an integer of 0 to 3, preferably an integer of 0 to 2, more preferably 0 or 1, and most preferably 1. Namely, it is particularly preferable that the group represented by the formula —[Y$^{21}$—C(=O)—O]$_{m'}$—Y$^{22}$— is a group represented by the formula —Y$^{21}$—C(=O)—O—Y$^{22}$—. Among these, a group represented by the formula —(CH$_2$)$_{a'}$—C(=O)—O—(CH$_2$)$_{b'}$— is preferable. In the formula, a' represents an integer of 1 to 10, preferably an integer of 1 to 8, more preferably an integer of 1 to 5, still more preferably 1 or 2, and most preferably 1. b' represents an integer of 1 to 10, preferably an integer of 1 to 8, more preferably an integer of 1 to 5, still more preferably 1 or 2, and most preferably 1.

In the present invention, Ya$^{21}$ preferably represents an ester bond [—C(=O)—O—], an ether bond (—O—), a linear or branched alkylene group, a combination of these, or a single bond.

In general formula (a2-1), Ra$^{21}$ represents a —SO$_2$-containing cyclic group, a lactone-containing cyclic group, a carbonate-containing cyclic group, or a heterocyclic group other than these.

The term "—SO$_2$-containing cyclic group" refers to a cyclic group including a ring containing a —SO$_2$— in its ring structure and, specifically, a cyclic group in which a sulfur atom (S) in —SO$_2$— forms a part of the ring structure of the cyclic group. The ring containing —SO$_2$— in its ring structure is counted as the first ring. The —SO$_2$-containing cyclic group in which the only ring structure is the ring containing a —SO$_2$— in its ring structure is referred to as a monocyclic group, and groups containing other ring structures are described as polycyclic groups regardless of the structure of the other rings. The —SO$_2$-containing cyclic group may be either a monocyclic group or a polycyclic group.

The —SO$_2$-containing cyclic group is particularly preferably a cyclic group including —O—SO$_2$— in its ring structure, that is, a cyclic group including a sultone ring in which —O—S— in —O—SO$_2$— forms a part of the ring structure. Examples of the —SO$_2$-containing cyclic group include the group represented by any one of general formulae (a5-r-1) to (a5-r-4) shown below.

[Chemical formula 60]

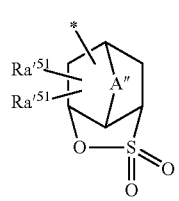
(a5-r-1)

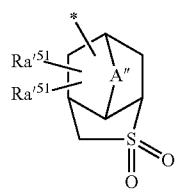
(a5-r-2)

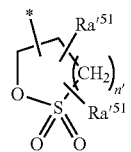
(a5-r-3)

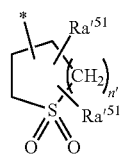
(a5-r-4)

In the formulae, each Ra'$^{51}$ independently represents a hydrogen atom, an alkyl group, an alkoxy group, a halogen atom, a halogenated alkyl group, a hydroxyl group, —COOR", —OC(=O) R", a hydroxyalkyl group, or a cyano group; R" represents a hydrogen atom or an alkyl group; A" represents an oxygen atom, a sulfur atom, or an alkylene group having 1 to 5 carbon atoms which may have an oxygen atom or a sulfur atom; and n' represents an integer of 0 to 2.

In general formulae (a5-r-1) to (a5-r-4), A" is the same as A" in general formulae (a2-r-1) to (a2-r-7) shown below. An alkyl group, an alkoxy group, a halogen atom, a halogenated alkyl group, —COOR", —OC(=O)R", and a hydroxyalkyl group for Ra'$^{51}$ are the same as those of Ra'$^{21}$ in general formulae (a2-r-1) to (a2-r-7) shown below.

Examples of the group represented by any one of the following general formulae (a5-r-1) to (a5-r-4) are shown. "Ac" in the formulae represents an acetyl group.

[Chemical formula 61]
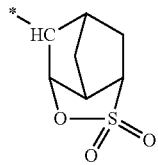 (r-sl-1-1)
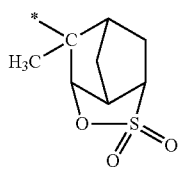 (r-sl-1-2)
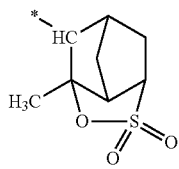 (r-sl-1-3)
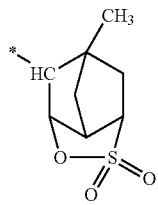 (r-sl-1-4)
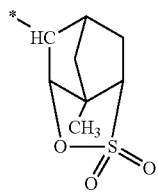 (r-sl-1-5)
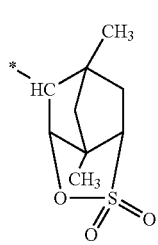 (r-sl-1-6)
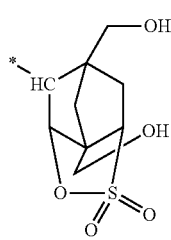 (r-sl-1-7)
-continued
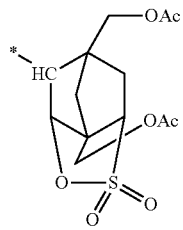 (r-sl-1-8)
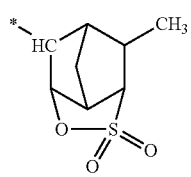 (r-sl-1-9)
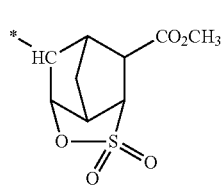 (r-sl-1-10)
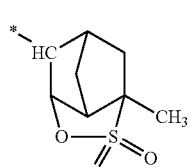 (r-sl-1-11)
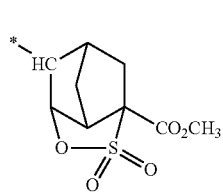 (r-sl-1-12)
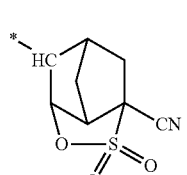 (r-sl-1-13)
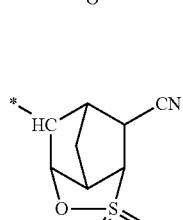 (r-sl-1-14)
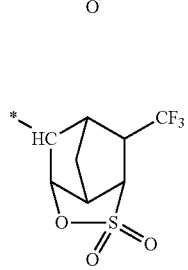 (r-sl-1-15)

(r-sl-1-16)
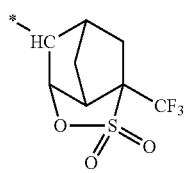
(r-sl-1-17)
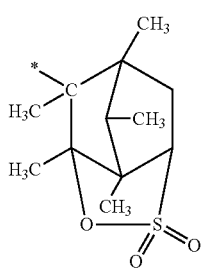
(r-sl-1-18)
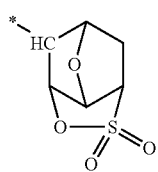
(r-sl-1-19)
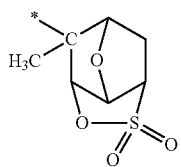
(r-sl-1-20)
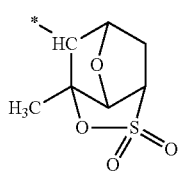
(r-sl-1-21)
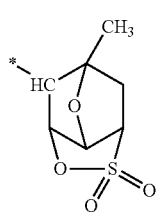
[Chemical formula 62]
(r-sl-1-22)
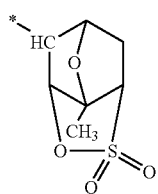
(r-sl-1-23)
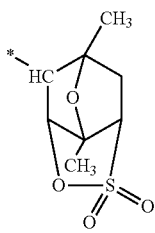
(r-sl-1-24)
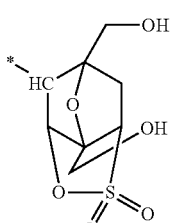
(r-sl-1-25)
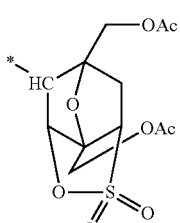
(r-sl-1-26)
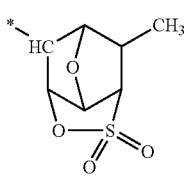
(r-sl-1-27)
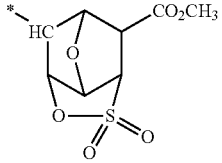
(r-sl-1-28)
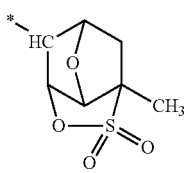
(r-sl-1-29)
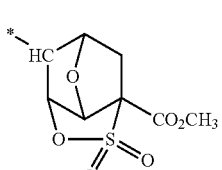
(r-sl-1-30)
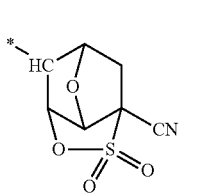

-continued

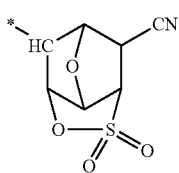
(r-sl-1-31)

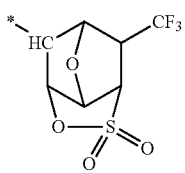
(r-sl-1-32)

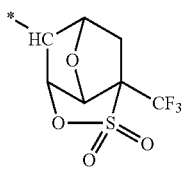
(r-sl-1-33)

[Chemical formula 63]

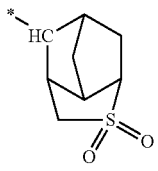
(r-sl-2-1)

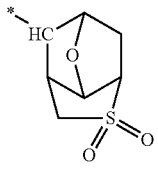
(r-sl-2-2)

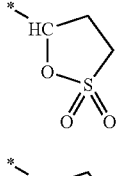
(r-sl-3-1)

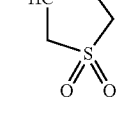
(r-sl-4-1)

In the embodiment, in the case where the structural unit (a2) includes the —SO$_2$-containing cyclic group, among the above, the group represented by general formula (a5-r-1) is preferable, at least one type selected from the group consisting of the groups represented by any one of Chemical formulae (r-sl-1-1), (r-sl-1-18), (r-sl-3-1), and (r-sl-4-1) is preferably used, and the group represented by Chemical formula (r-sl-1-1) is most preferable.

The term "lactone-containing cyclic group" refers to a cyclic group including a ring containing a —O—C(=O)— structure (lactone ring). The lactone ring refers to a single ring containing a —O—C(O)— structure, and this ring is counted as the first ring. A lactone-containing cyclic group in which the only ring structure is the lactone ring is referred to as a monocyclic group, and groups containing other ring structures are referred to as polycyclic groups regardless of the structure of the other rings. The lactone-containing cyclic group may be either a monocyclic group or a polycyclic group.

As the lactone-containing cyclic group, there is no particular limitation, and an arbitrary group may be used. Examples include groups represented by general formulae (a2-r-1) to (a2-r-7) shown below. Hereinbelow, "*" represents a valence bond.

[Chemical formula 64]

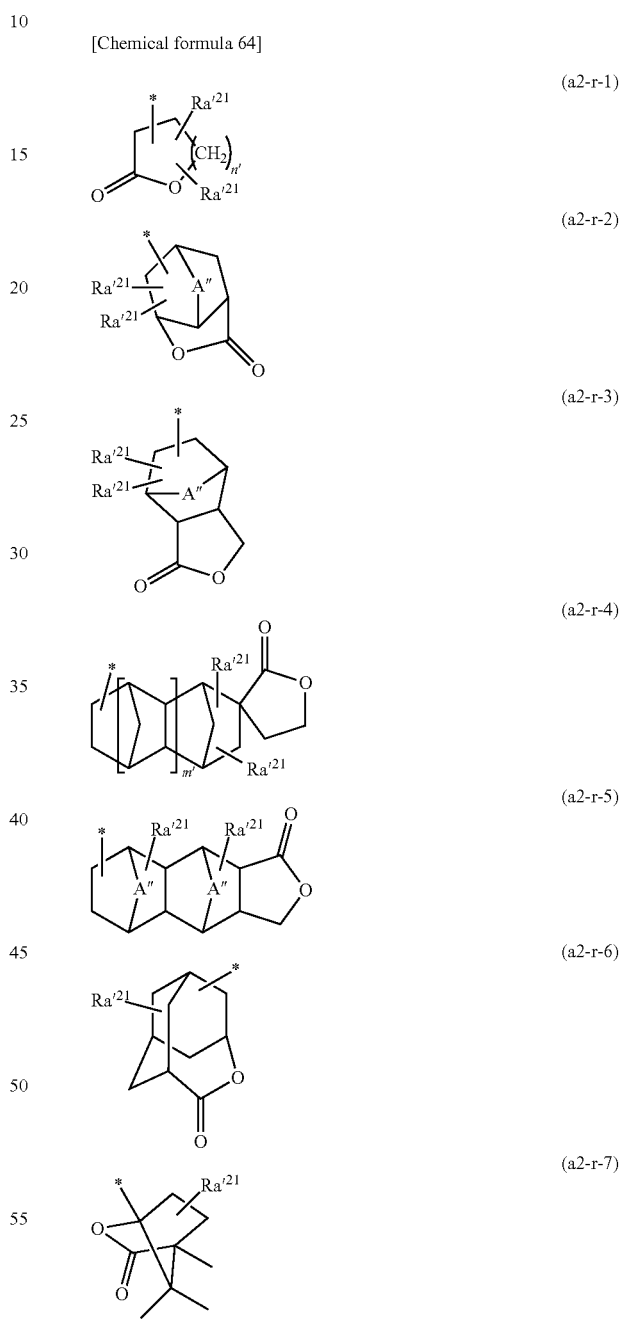

In the formulae, each Ra$'^{21}$ independently represents a hydrogen atom, an alkyl group, an alkoxy group, a halogen atom, a halogenated alkyl group, a hydroxyl group, —COOR″, —OC(=O) R″, a hydroxyalkyl group or a cyano group; R″ represents a hydrogen atom or an alkyl group; A″ represents an oxygen atom, a sulfur atom or an alkylene group having 1 to 5 carbon atoms which may contain an oxygen atom or a sulfur atom; n' represents an integer of 0 to 2; and m' represents 0 or 1.

In general formulae (a2-r-1) to (a2-r-7) above, A" represents an oxygen atom, a sulfur atom, or an alkylene group having 1 to 5 carbon atoms which may contain an oxygen atom (—O—) or a sulfur atom (—S—). As the alkylene group having 1 to 5 carbon atoms for A", a linear or branched alkylene group is preferable, and examples thereof include a methylene group, an ethylene group, an n-propylene group and an isopropylene group. In the case where the alkylene group includes an oxygen atom or a sulfur atom, examples thereof include a group in which —O— or —S— is interposed between the terminal of the alkylene group and the carbon atoms of the alkylene group. Examples of such a group include —O—CH$_2$—, —CH$_2$—O—CH$_2$—, —S—CH$_2$— and —CH$_2$—S—CH$_2$—. As A", an alkylene group having 1 to 5 carbon atoms or —O— is preferable, an alkylene group having 1 to 5 carbon atoms is more preferable, and a methylene group is most preferable. Each Ra'$^{21}$ independently represents an alkyl group, an alkoxy group, a halogen atom, a halogenated alkyl group, —COOR", —OC(=O)R", a hydroxyalkyl group, or a cyano group.

As the alkyl group for Ra'$^{21}$, an alkyl group having 1 to 5 carbon atoms is preferable.

As the alkoxy group for Ra'$^{21}$, an alkoxy group having 1 to 6 carbon atoms is preferable.

The alkoxy group is preferably linear or branched. Examples thereof include a group in which the alkyl group exemplified as the alkyl group for Ra'$^{21}$ and an oxygen atom (—O—) are linked to each other.

Examples of the halogen atom for Ra'$^{21}$ include a fluorine atom, a chlorine atom, a bromine atom, and an iodine atom, and a fluorine atom is preferable.

Examples of the halogenated alkyl group for Ra'$^{21}$ include a group in which a part or all of the hydrogen atoms of the alkyl group for Ra'$^{21}$ is substituted with the halogen atom. As the halogenated alkyl group, a fluorinated alkyl group is preferable and a perfluoroalkyl group is particularly preferable.

R" represents a hydrogen atom or an alkyl group, as the alkyl group for R", an alkyl group having 1 to 5 carbon atoms is preferable.

Examples of the group represented by any one of the following general formulae (a2-r-1) to (a2-r-7) will be shown.

[Chemical formula 65]

(r-lc-1-1)

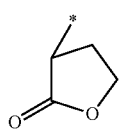

(r-lc-1-2)

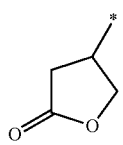

(r-lc-1-3)

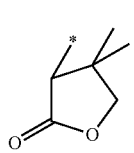

(r-lc-1-4)

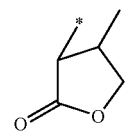

(r-lc-1-5)

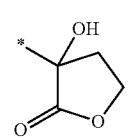

(r-lc-1-6)

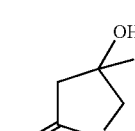

(r-lc-1-7)

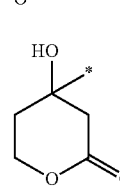

(r-lc-2-1)

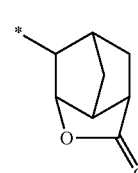

(r-lc-2-2)

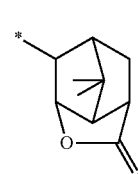

(r-lc-2-3)

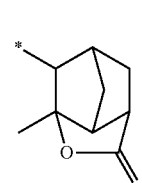

(r-lc-2-4)

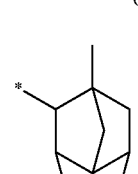

(r-lc-2-5)

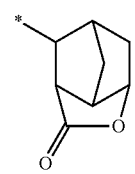

-continued
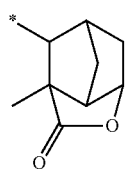 (r-lc-2-6)
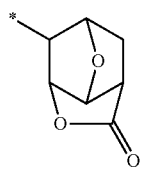 (r-lc-2-7)
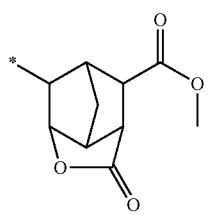 (r-lc-2-8)
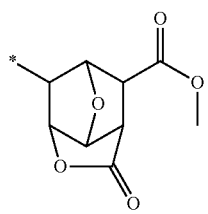 (r-lc-2-9)
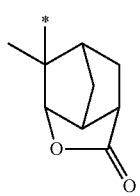 (r-lc-2-10)
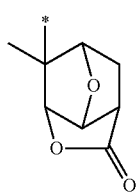 (r-lc-2-11)
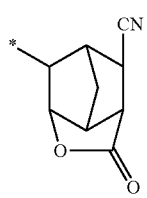 (r-lc-2-12)
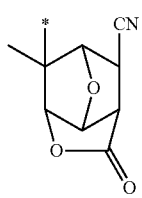 (r-lc-2-13)
-continued
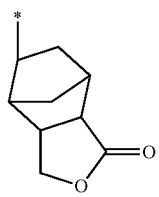 (r-lc-3-1)
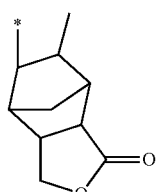 (r-lc-3-2)
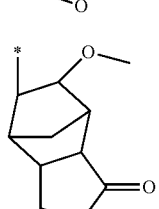 (r-lc-3-3)
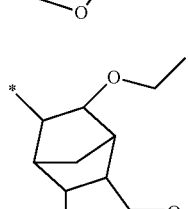 (r-lc-3-4)
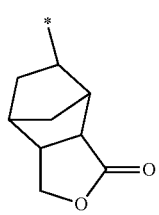 (r-lc-3-5)
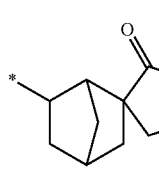 (r-lc-4-1)
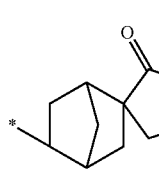 (r-lc-4-2)
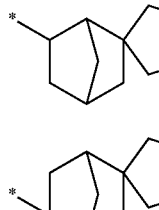 (r-lc-4-3)
 (r-lc-4-4)

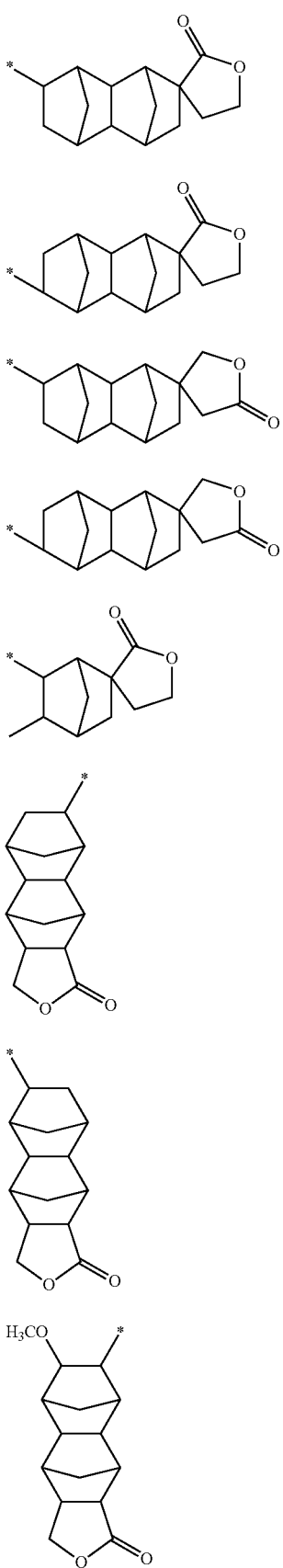

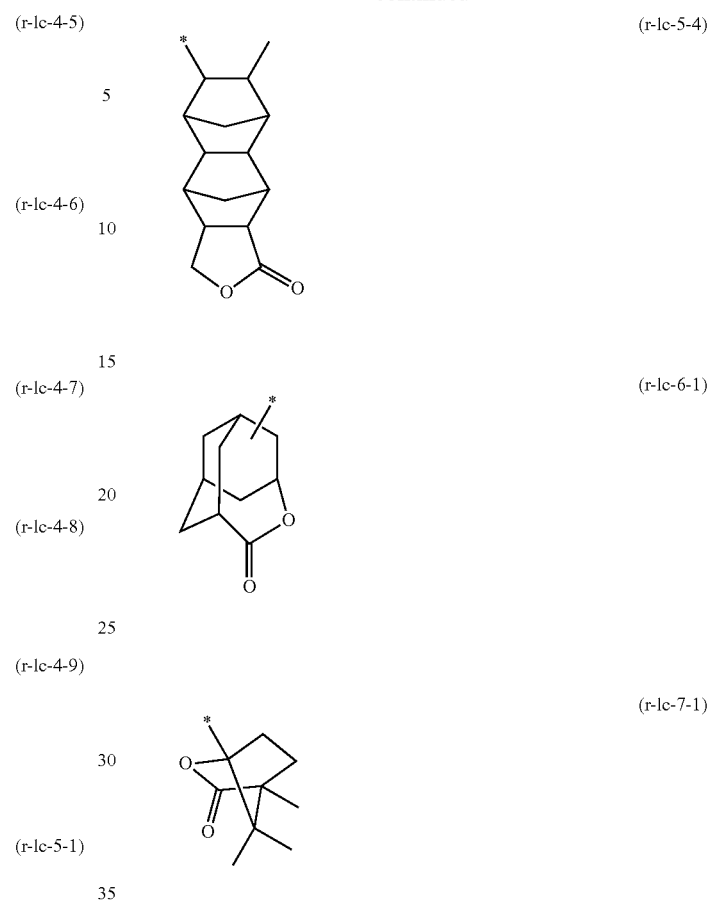

In the embodiment, as the structural unit (a2), the groups represented by general formula (a2-r-1) or (a2-r-2) are preferable, and the groups represented by chemical formula (r-lc-1-1) or (r-lc-2-7) are more preferable.

The term "carbonate-containing cyclic group" refers to a cyclic group including a ring containing a —O—C(=O)—O— (carbonate ring) in its ring structure. The carbonate ring is counted as the first ring. A carbonate-containing cyclic group in which the carbonate ring is the only ring structure is referred to as a monocyclic group, and groups containing other ring structures are described as polycyclic groups regardless of the structure of the other rings. The carbonate-containing cyclic group may be either a monocyclic group or a polycyclic group.

The carbonate ring-containing cyclic group is not particularly limited, and an arbitrary group can be used. Examples thereof include the group represented by any one of the following general formulae (ax3-r-1) to (ax3-r-3).

[Chemical formula 66]

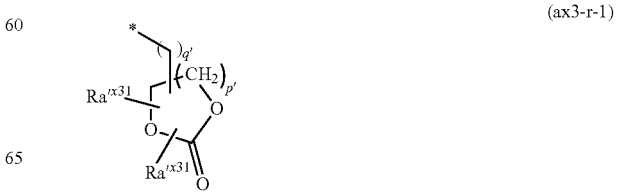

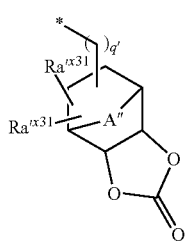
(ax3-r-2)

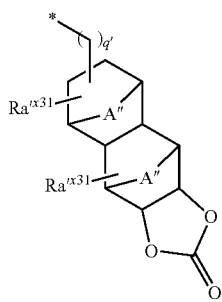
(ax3-r-3)

In the formulae, each $Ra'^{x31}$ independently represents a hydrogen atom, an alkyl group, an alkoxy group, a halogen atom, a halogenated alkyl group, a hydroxyl group, —COOR″, —OC(=O) R″, a hydroxyalkyl group, or a cyano group; R″ represents a hydrogen atom or an alkyl group; A″ represents an oxygen atom, a sulfur atom, or an alkylene group having 1 to 5 carbon atoms which may have an oxygen atom or a sulfur atom; and q′ represents 0 or 1. p′ represents an integer of 0 to 3.

A″ of general formulae (ax3-r-2) and (ax3-r-3) is the same as the A″ of general formula (a2-r-2), (a2-r-3) or (a2-r-5).

As the alkyl group, alkoxy group, halogen atom, halogenated alkyl group, —COOR″, —OC(=O)R″, or hydroxyalkyl group for $Ra'^{31}$, the same groups exemplified above in the description for $Ra'^{21}$ of general formulae (a2-r-1) to (a2-r-7) can be mentioned respectively.

Examples of the group represented by any one of the following general formulae (ax3-r-1) to (ax3-r-3) will be shown.

[Chemical formula 67]

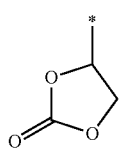
(r-cr-1-1)

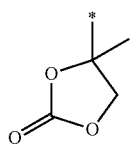
(r-cr-1-2)

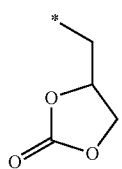
(r-cr-1-3)

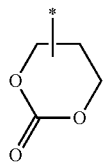
(r-cr-1-4)

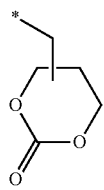
(r-cr-1-5)

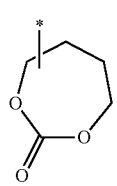
(r-cr-1-6)

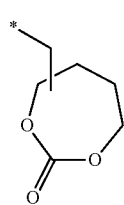
(r-cr-1-6)

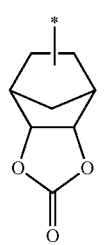
(r-cr-2-1)

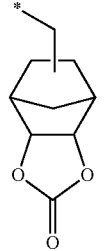
(r-cr-2-2)

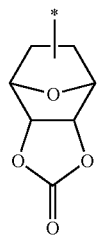
(r-cr-2-3)

(r-cr-2-4)

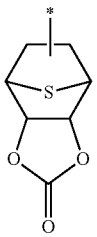

(r-cr-3-1)

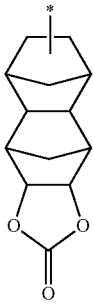

(r-cr-3-2)

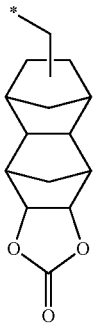

(r-cr-3-3)

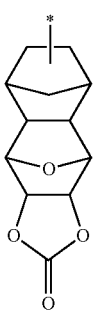

(r-cr-3-4)

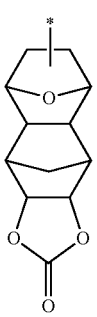

(r-cr-3-5)

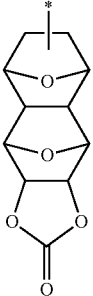

The "heterocyclic group" other than the above refers to a cyclic group including one or more atoms (excluding a carbon atom) in addition to the carbon atom, and examples thereof include each heterocyclic group represented by Chemical formulae (r-hr-1) to (r-hr-16) below and a nitrogen-containing heterocyclic group. As the nitrogen-containing heterocyclic group, a cycloalkyl group having 3 to 8 carbon atoms which may be substituted with one or two oxo groups can be exemplified. Preferred examples of the nitrogen-containing cycloalkyl group include 2,5-dioxopyrrolidin and a group in which one or more hydrogen atoms are removed from 2,6-dioxopiperidine.

As the structural unit (a2) contained in the component (A1), one type of structural unit may be used, or 2 or more types may be used.

When the component (A1) contains the structural unit (a2), the amount of the structural unit (a2) based on the total of all the structural units constituting the component (A1) is preferably 1 mol % to 80 mol %, more preferably 5 mol % to 70 mol %, still more preferably 10 mol % to 65 mol %, and most preferably 10 mol % to 60 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance with the other structural units can be achieved, and thereby, various lithography properties and pattern shape can be improved.

Structural Unit (a3)

The structural unit (a3) is a structural unit containing a polar group-containing aliphatic hydrocarbon group (provided that the structural units that fall under the definition of structural units (a1) and (a2) are excluded).

When the component (A1) includes the structural unit (a3), it is presumed that the hydrophilicity of the component (A) is enhanced, thereby contributing to improvement in resolution.

Examples of the polar group include a hydroxyl group, a cyano group, a carboxyl group, or a hydroxyalkyl group in which a part of the hydrogen atom of the alkyl group is substituted with a fluorine atom, while a hydroxyl group is particularly preferable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups may be monocyclic or polycyclic, and can be selected appropriately from various groups known for the resins of resist compositions designed for use with ArF excimer lasers. The cyclic group is preferably a polycyclic group, more preferably a polycyclic group having 7 to 30 carbon atoms.

Of the various possibilities, structural units derived from an acrylic ester that include an aliphatic polycyclic group that contains a hydroxyl group, a cyano group, a carboxyl group or a hydroxyalkyl group in which a part of the hydrogen atom of the alkyl group is substituted with a fluorine atom are particularly preferable. Examples of the polycyclic group include groups in which two or more hydrogen atoms are removed from bicycloalkane, tricycloalkane, tetracycloalkane or the like. Examples thereof include groups in which two or more hydrogen atoms are removed from a polycycloalkane such as adamantane, norbornane, isobornane, tricyclodecane or tetracyclododecane. Of these polycyclic groups, groups in which two or more hydrogen atoms are removed from adamantane, norbornane or tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylic ester in which the hydrogen atom bonded to the carbon atom on the α-position may be substituted with a substituent and which contains a polar group-containing aliphatic hydrocarbon group.

When the hydrocarbon group in the polar group-containing aliphatic hydrocarbon group is a linear or branched hydrocarbon group having 1 to 10 carbon atoms, the structural unit (a3) is preferably a structural unit derived from a hydroxyethyl ester of acrylic acid. On the other hand, when the hydrocarbon group is a polycyclic group, structural units represented by formulae (a3-1), (a3-2) and (a3-3) shown below are preferable.

[Chemical formula 68]

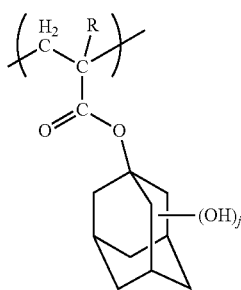

(a3-1)

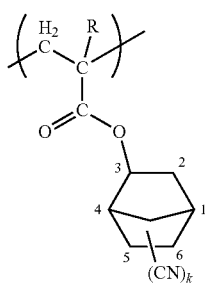

(a3-2)

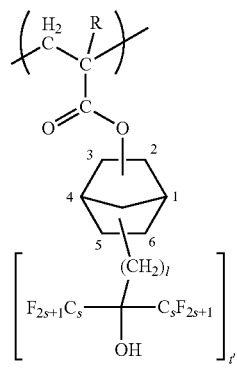

(a3-3)

In general formulae (a3-1) to (a3-3), R represents a hydrogen atom, an alkyl group having 1 to 5 carbon atoms, or a halogenated alkyl group having 1 to 5 carbon atoms, j represents an integer of 1 to 3, k represents an integer of 1 to 3, t' represents an integer of 1 to 3, l represents an integer of 1 to 5, and s represents an integer of 1 to 3.

In general formulae (a3-1) to (a3-3), the description in relation to R is the same as the above.

In general formula (a3-1), j is preferably 1 or 2, and more preferably 1. In the case where j is 2, the hydroxyl group is preferably bonded to the 3rd position and 5th position of the adamantyl group. In the case where j is 1, the hydroxyl group is preferably bonded to the 3rd position of the adamantyl group.

j is preferably 1, and the hydroxyl group is particularly preferably bonded to 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A1), one type of structural unit may be used, or 2 or more types may be used.

The amount of the structural unit (a3) in the component (A1) based on the combined total of all of the structural units constituting the resin component (A1) is preferably 5 mol % to 50 mol %, more preferably 5 mol % to 40 mol %, and still more preferably 5 mol % to 25 mol %.

When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

Structural Unit (a4)

The structural unit (a4) is a structural unit containing an acid non-dissociable cyclic group. When the component (A1) includes the structural unit (a4), dry etching resistance of the resist pattern to be formed is improved. Further, the hydrophobicity of the component (A1) is further improved. Increase in the hydrophobicity contributes to improvement in terms of resolution, shape of the resist pattern and the like, particularly in an organic solvent developing process.

An "acid non-dissociable cyclic group" in the structural unit (a4) refers to a cyclic group which is not dissociated by the action of an acid generated from the component (B) described later upon exposure, and remains in the structural unit.

As the structural unit (a4), a structural unit derived from an acrylic ester containing a non-acid-dissociable aliphatic cyclic group is preferable. Examples of this cyclic group include the same groups as those described above in relation to the aforementioned structural unit (a1), and any of the multitude of conventional groups used for the resin component of resist compositions for ArF excimer laser or KrF excimer laser (and particularly for ArF excimer lasers) can be used.

In consideration of industrial availability and the like, at least one polycyclic group selected from amongst a tricyclodecyl group, an adamantyl group, a tetracyclododecyl group, an isobornyl group, and a norbornyl group is particularly preferable. These polycyclic groups may have a linear or branched alkyl group having 1 to 5 carbon atoms as a substituent.

Examples of the structural unit (a4) include structural units represented by general formulae (a4-1) to (a4-7) shown below.

[Chemical formula 69]

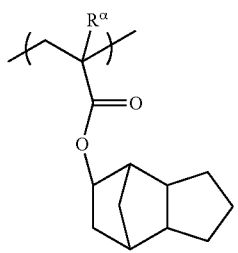

(a4-1)

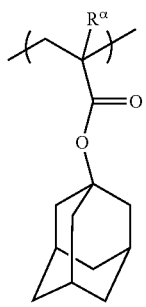

(a4-2)

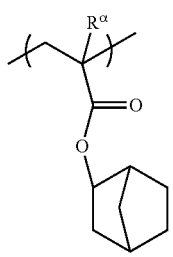

(a4-3)

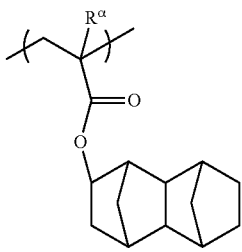

(a4-4)

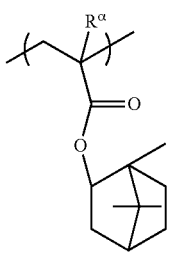

(a4-5)

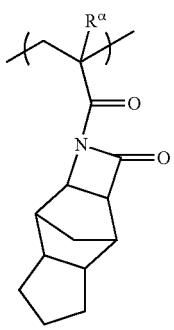

(a4-6)

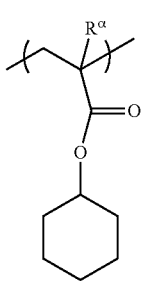

(a4-7)

In formulae (a4-1) to (a4-7), $R^\alpha$ represents a hydrogen atom, a methyl group, or a trifluoromethyl group.

The type of the structural unit (a4) included in the component (A1) may be one or two or more.

When the structural unit (a4) is included in the component (A1), the ratio of the structural unit (a4) is preferably 1 mol % to 30 mol % and more preferably 10 mol % to 20 mol % with respect to all of the structural units configuring the component (A1).

The component (A1) is preferably a copolymer having (a1) and (a10), a copolymer having (a1) and (a12), a copolymer having (a1) and (a9), a copolymer having (a10) and (a12), or a copolymer having (a1), (a2), and (a10).

The component (A1) can be obtained by polymerizing a monomer deriving each structural unit by means of the well-known radical polymerization or the like using a radical polymerization initiator such as azobisisobutyronitrile (AIBN) and azobisisobutyric acid dimethyl.

In addition, a —C(CF$_3$)$_2$—OH group may be introduced to the terminal of the component (A1) at the time of the aforementioned polymerization, for example, by using a chain-transfer agent such as HS—$CH_2$—$CH_2$—$CH_2$—C$(CF_3)_2$—OH. In this way, a copolymer having a hydroxyalkyl group introduced thereto, in which a part of the hydrogen atom of the alkyl group is substituted with a fluorine atom can effectively decrease a development defect or LER (line edge roughness: nonuniform irregularities on a line side wall).

In the embodiment, the weight average molecular weight (Mw) of the component (A1) (in terms of polystyrene by means of Gel Permeation Chromatography) is not particularly limited, and the weight average molecular weight is preferably 1,000 to 50,000, more preferably 1,500 to 30,000, and most preferably 2,000 to 20,000. If the weight average molecular weight is equal to or less than the upper limit of this range, the component has solubility in a resist solvent enough to be used as a resist, and if the weight average molecular weight is equal to or more than the lower limit of this range, dry etching resistance or a resist pattern cross-sectional shape is satisfactory.

The component (A1) may be used alone or two or more types thereof may be used in combination.

The ratio of the component (A1) of the base material component (A) is preferably 25 mass % or more, more preferably 50 mass %, and still more preferably 75 mass % with respect to the total mass of the base material component (A), and may be 100 mass %. If the ratio is 25 mass % or more, lithography properties are further improved.

In the embodiment, the component (A) may be used alone or two or more types thereof may be used in combination.

In the embodiment, the content of the component (A) may be adjusted depending on the thickness of the resist film to be formed.

Component (B1)

An acid generator component (B1) which generates an acid upon exposure included in the positive-type resist composition of the present invention will be described.

The component (B1) is an acid generator component which generates an acid upon exposure, and includes a compound (m) represented by general formula (m0). In the first embodiment, the compound (m) is preferably a compound represented by the following general formula (m0-1).

[Chemical formula 70]

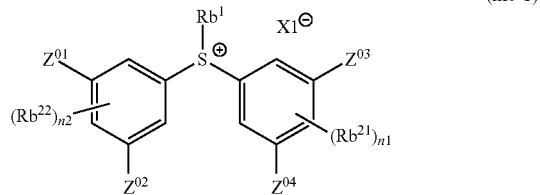

(m0-1)

In general formula (m0-1), $Z^{01}$ to $Z^{04}$ each independently represent a substituent having electron withdrawing properties, $Rb^{21}$ and $Rb^{22}$ each independently represent an alkyl group which may have a substituent, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^1$ represents an aryl group which may have a substituent, an alkyl group which may have a substituent, or an alkenyl group which may have a substituent, n1 and n2 each independently represent an integer of 0 to 3, and $X1^-$ represents an organic anion which can generate an acid that can increase solubility of the base material component (A) in an alkali developing solution.

In general formula (m0-1), the description in relation to $Z^{01}$ to $Z^{04}$, $Rb^{21}$, $Rb^{22}$, $Rb^1$, and n1 and n2 is the same as the description of general formula (m0).

In general formula (m0-1), $X1^-$ represents an organic anion which can generate an acid that can increase solubility of the base material component (A) in an alkali developing solution.

$X1^-$ may be an organic anion which can generate an acid having the strength capable of increasing solubility of the base material component (A) in an alkali developing solution.

Meanwhile, the positive-type resist composition of the first embodiment includes a component (D1) described below. The component (D1) is a component acting as a quencher which traps an acid generated from the component (B1) and the details thereof will be described below. Therefore, the anion moiety $X1^-$ of the compound (m0-1) configuring the component (B1) is the anion moiety which can generate an acid which is strong with respect to the component (D1).

For example, the acid strength is described using an acid dissociation constant (pKa) as an index.

In the embodiment, the "acid dissociation constant (pKa)" is generally used as an index indicating an acid strength of a target substance. In addition, pKa in the present specification refers to a value at a temperature condition of 25° C. In addition, the pKa value can be obtained by measurement according to the well-known method. In addition, it is possible to use a calculated value obtained by using the well-known software such as "ACD/Labs" (trade name, manufactured by Advanced Chemistry Development) or the like.

In general formula (m0-1), the lower limit of the acid dissociation constant (pKa) of the acid generated from $X1^-$ is not particularly limited, and the lower limit is substantially about −15. The upper limit of the acid dissociation constant (pKa) of the acid generated from $X1^-$ is preferably lower than the acid dissociation constant (pKa) of the acid generated from the component (D1), for example, the value of about 1.5 to 2.0. Even in the case where the acid dissociation constant (pKa) of the acid generated from $X1^-$ is about 1.5 to 2.0, it is possible to increase solubility of the base material component (A) in an alkali developing solution.

More specifically, in general formula (m0-1), the anion represented by any one of the following general formulae (m-an-1) to (m-an-3) is preferable as $X1^-$.

[Chemical formula 71]

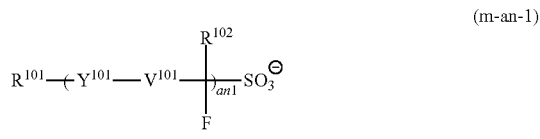

(m-an-1)

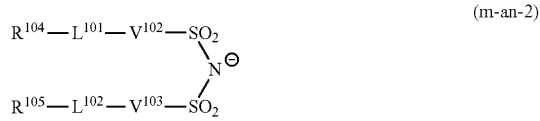

(m-an-2)

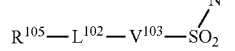

(m-an-3)

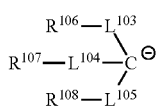

In general formulae (m-an-1) to (m-an-3), $R^{101}$ and $R^{104}$ to $R^{108}$ each independently represent a cyclic group which may have a substituent, a chain-like alkyl group which may have a substituent, or a chain-like alkenyl group which may have a substituent.

$R^{104}$ and $R^{105}$ may be bonded to each other to form a ring.

Any two of $R^{106}$ to $R^{107}$ may be bonded to each other to form a ring.

$R^{102}$ represents a fluorine atom or a fluorinated alkyl group having 1 to 5 carbon atoms.

$Y^{101}$ represents a single bond or a divalent linking group including an oxygen atom.

$V^{101}$ to $V^{103}$ each independently represent a single bond, an alkylene group, or a fluorinated alkylene group. $L^{101}$ and $L^{102}$ each independently represent a single bond or an oxygen atom. $L^{103}$ to $L^{105}$ each independently represent a single bond, —CO—, or —SO$_2$—. an1 represents 0 or 1.

General Formula (m-an-1)

In general formula (m-an-1), $R^{101}$ represents a cyclic group which may have a substituent, a chain-like alkyl group which may have a substituent, or a chain-like alkenyl group which may have a substituent.

Cyclic Group which May have a Substituent for $R^{101}$

The cyclic group is preferably a cyclic hydrocarbon group and the cyclic hydrocarbon group may be an aromatic hydrocarbon group or an aliphatic hydrocarbon group.

Examples of the aromatic hydrocarbon group for $R^{101}$ include an aryl group in which one hydrogen atom is removed from an aromatic compound including two or more aromatic rings or an aromatic hydrocarbon ring exemplified in the divalent aromatic hydrocarbon group for $Va^1$ of general formula (a1-1) and, a phenyl group or a naphthyl group is preferable.

Examples of the cyclic aliphatic hydrocarbon group for $R^{101}$ include a group in which one hydrogen atom is removed from monocycloalkane or polycycloalkane exemplified in the divalent aliphatic hydrocarbon group for $Va^1$ of general formula (a1-1), and an adamantyl group or a norbornyl group is preferable.

In addition, the cyclic hydrocarbon group for $R^{101}$ may include a hetero atom such as a heterocycle, and examples thereof include the lactone-containing cyclic group represented by any one of general formulae (a2-r-1) to (a2-r-7) and the —SO$_2$-containing cyclic group represented by any one of general formula (a5-r-1) to (a5-r-4), in addition to heterocyclic group exemplified by any one of the following chemical formulae (r-hr-1) to (r-hr-16).

[Chemical formula 72]

(r-hr-1)

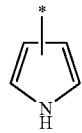

(r-hr-2)

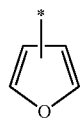

(r-hr-3)

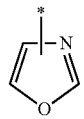

(r-hr-4)

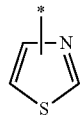

(r-hr-5)

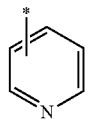

(r-hr-6)

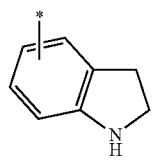

(r-hr-7)

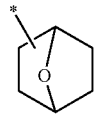

(r-hr-8)

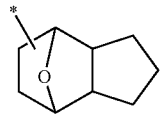

(r-hr-9)

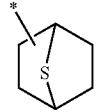

(r-hr-10)

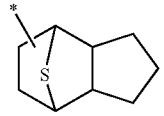

(r-hr-11)

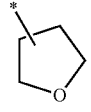

(r-hr-12)

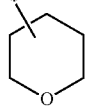

(r-hr-13)

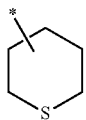
(r-hr-14)

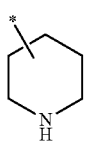
(r-hr-15)

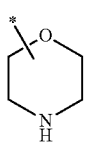
(r-hr-16)

Examples of the substituent of the cyclic hydrocarbon group for $R^{101}$ include an alkyl group, an alkoxy group, a halogen atom, a halogenated alkyl group, a hydroxyl group, a carbonyl group, and a nitro group.

As the alkyl group of the substituent, an alkyl group having 1 to 5 carbon atoms is preferable, and a methyl group, an ethyl group, a propyl group, an n-butyl group, or a tert-butyl group is most preferable.

As an alkoxy group of the substituent, an alkoxy group having 1 to 5 carbon atoms is preferable, a methoxy group, an ethoxy group, an n-propoxy group, an iso-propoxy group, an n-butoxy group, or a tert-butoxy group is more preferable, and a methoxy group or an ethoxy group is most preferable.

Examples of the halogen atom of the substituent include a fluorine atom, a chlorine atom, a bromine atom, and an iodine atom, and a fluorine atom is preferable.

Examples of the halogenated alkyl group of the substituent include a group in which a part or all of the hydrogen atoms of an alkyl group having 1 to 5 carbon atoms, such as a methyl group, an ethyl group, a propyl group, an n-butyl group, and a tert-butyl group, is substituted with the halogen atom.

Chain-Like Alkyl Group which May have a Substituent for $R^{101}$

The chain-like alkyl group for $R^{101}$ may be linear or branched.

The linear alkyl group preferably has 1 to 20 carbon atoms, more preferably 1 to 15, and most preferably 1 to 10. Examples thereof include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group, and a docosyl group.

The branched alkyl group preferably has 3 to 20 carbon atoms, more preferably 3 to 15, and most preferably 3 to 10. Examples thereof include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

Chain-Like Alkenyl Group which May have a Substituent for $R^{101}$

The chain-like alkenyl group for $R^{101}$ may be linear or branched and preferably has 2 to 10 carbon atoms, more preferably 2 to 5, still more preferably 2 to 4, and particularly preferably 3. Examples of the linear alkenyl group include a vinyl group, a propenyl group (an allyl group), and a butynyl group. Examples of the branched alkenyl group include a 1-methylpropenyl group, and a 2-methylpropenyl group.

Among the above, a propenyl group is preferable as the chain-like alkenyl group.

Examples of the substituent of the chain-like alkyl group or alkenyl group for $R^{101}$ include an alkoxy group, a halogen atom, a halogenated alkyl group, a hydroxyl group, a carbonyl group, a nitro group, an amino group, and a cyclic group for the above $R^{101}$.

Among these, $R^{101}$ is preferably a cyclic group which may have a substituent and more preferably a cyclic hydrocarbon group which may have a substituent. More specifically, a phenyl group, a naphthyl group, a group in which one or more hydrogen atoms are removed from polycycloalkane, the lactone-containing cyclic group represented by any one of general formulae (a2-r-1) to (a2-r-7), or the $-SO_2$-containing cyclic group represented by any one of general formulae (a5-r-1) to (a5-r-4) is preferable.

In general formula (m-an-1), $Y^{101}$ represents a single bond or a divalent linking group including an oxygen atom.

In the case where $Y^{101}$ represents a divalent linking group including an oxygen atom, $Y^{101}$ may include an atom other than the oxygen atom. Examples of the atom other than the oxygen atom include a carbon atom, a hydrogen atom, a sulfur atom, and a nitrogen atom.

Examples of the divalent linking group including an oxygen atom include a non-hydrocarbon based oxygen atom-containing linking group such as an oxygen atom (an ether bond: $-O-$), an ester bond ($-C(=O)-O-$), an oxycarbonyl group ($-O-C(=O)-$), an amide bond ($-C(=O)-NH-$), a carbonyl group ($-C(=O)-$), a carbonate bond ($-O-C(=O)-O-$); and a combination of the non-hydrocarbon based oxygen atom-containing linking group and an alkylene group. Further, a sulfonyl group ($-SO_2-$) may be linked to the combination. Examples of the combination include the linking group represented by any one of the following general formulae (y-al-1) to (y-al-7).

[Chemical formula 73]

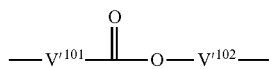
(y-al-1)

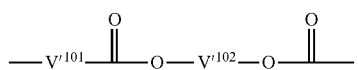
(y-al-2)

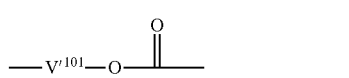
(y-al-3)

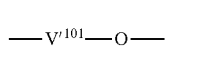
(y-al-4)

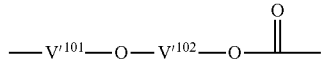
(y-al-5)

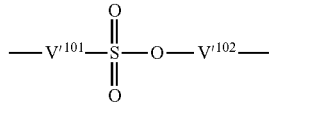
(y-al-6)

-continued

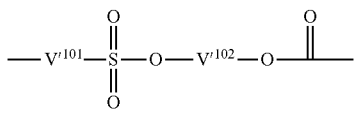

(y-al-7)

In general formulae (y-al-1) to (y-al-7), $V'^{101}$ represents a single bond or an alkylene group having 1 to 5 carbon atoms, and $V'^{102}$ represents a divalent saturated hydrocarbon group having 1 to 30 carbon atoms.

The divalent saturated hydrocarbon group for $V'^{102}$ is preferably an alkylene group having 1 to 30 carbon atoms.

The alkylene group for $V'^{101}$ and $V'^{102}$ may be a linear alkylene group or a branched alkylene group, and is preferably a linear alkylene group.

Examples of the alkylene group for $V'^{101}$ and $V'^{102}$ include a methylene group [—$CH_2$—]; an alkylmethylene group such as —$CH(CH_3)$—, —$CH(CH_2CH_3)$—, —$C(CH_3)_2$—, —$C(CH_3)(CH_2CH_3)$—, —$C(CH_3)$ ($CH_2CH_2CH_3$)—, and —$C(CH_2CH_3)_2$—; an ethylene group [—$CH_2CH_2$—]; an alkylethylene group such as —$CH(CH_3)$ $CH_2$—, —$CH(CH_3)CH(CH_3)$—, —$C(CH_3)_2CH_2$—, and —$CH(CH_2CH_3)CH_2$—; a trimethylene group (n-propylene group) [—$CH_2CH_2CH_2$—]; an alkyltrimethylene group such as —$CH(CH_3)CH_2CH_2$— and —$CH_2CH(CH_3)CH_2$—; a tetramethylene group [—$CH_2CH_2CH_2CH_2$—]; an alkyltetramethylene group such as —$CH(CH_3)CH_2CH_2CH_2$— and —$CH_2CH(CH_3)CH_2CH_2$—; and a pentamethylene group [—$CH_2CH_2CH_2CH_2CH_2$—].

In addition, a part of the methylene group of the alkylene group for $V'^{101}$ or $V'^{102}$ may be substituted with a divalent aliphatic group having 5 to 10 carbon atoms. As the aliphatic group, a divalent group in which a hydrogen atom is further removed from the cyclic aliphatic hydrocarbon group for $Ra^{t3}$ in formula (a1-r-1) is preferable, and a cyclohexylene group, a 1,5-adamantylene group, or a 2,6-adamantylene group is more preferable.

As $Y^{101}$, a divalent linking group having an ester bond or an ether bond is preferable, and the linking group represented by any one of general formulae (y-al-1) to (y-al-5) is preferable.

In general formula (m-an-1), $V^{101}$ represents a single bond, an alkylene group, or a fluorinated alkylene group. The alkylene group and the fluorinated alkylene group for $V^{101}$ have preferably 1 to 4 carbon atoms. Examples of the fluorinated alkylene group for $V^{101}$ include a group in which a part or all of the hydrogen atoms of the alkylene group for $V^{101}$ is substituted with a fluorine atom. Among these, $V^{101}$ is preferably a single bond, or a fluorinated alkylene group having 1 to 4 carbon atoms.

In general formula (m-an-1), $R^{102}$ represents a fluorine atom or a fluorinated alkyl group having 1 to 5 carbon atoms. $R^{102}$ is preferably a fluorine atom or a perfluoroalkyl group having 1 to 5 carbon atoms, and more preferably a fluorine atom.

As the anion moiety represented by general formula (m-an-1) include, in the case where $Y^{101}$ represents a single bond, a fluorinated alkyl sulfonate anion such as a trifluoromethane sulfonate anion and a perfluorobutane sulfonate anion is exemplified; and, in the case where $Y^{101}$ represents a divalent linking group including an oxygen atom, the anion represented by any one of the following general formulae (an-1) to (an-3) is exemplified.

[Chemical formula 74]

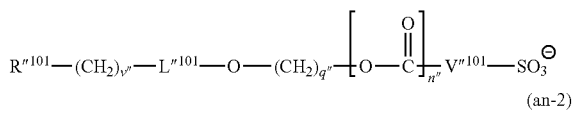

(an-1)

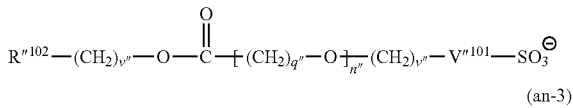

(an-2)

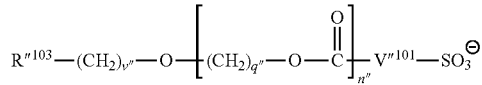

(an-3)

In the formulae, $R''^{101}$ represents an alicyclic group which may have a substituent, the group represented by any one of chemical formulae (r-hr-1) to (r-hr-6), or a chain-like alkyl group which may have a substituent; $R''^{102}$ represents an alicyclic group which may have a substituent, the lactone-containing cyclic group represented by any one of general formulae (a2-r-1) to (a2-r-7), or the —$SO_2$-containing cyclic group represented by any one of general formulae (a5-r-1) to (a5-r-4); $R''^{103}$ represents an aromatic cyclic group which may have a substituent, an alicyclic group which may have a substituent, or a chain-like alkenyl group which may have a substituent; $V''^{101}$ represents a fluorinated alkylene group; $L''^{101}$ represents —$C(=O)$— or —$SO_2$—; each v" independently represents an integer of 0 to 3, each q" independently represents an integer of 1 to 20, and n" represents an integer of 0 or 1.

As the alicyclic group which may have a substituent for $R''^{101}$, $R''^{102}$, and $R''^{103}$, the group exemplified as the cyclic aliphatic hydrocarbon group for $R^{101}$ is preferable. Examples of the substituent include the same substituent as the substituent which may substitute the cyclic aliphatic hydrocarbon group for $R^{101}$.

As the aromatic cyclic group which may have a substituent for $R''^{103}$, the group exemplified as the aromatic hydrocarbon group of the cyclic hydrocarbon group for $R^{101}$ is preferable. Examples of the substituent include the same substituent as the substituent which may substitute the aromatic hydrocarbon group for $R^{101}$.

As the chain-like alkyl group which may have a substituent for $R''^{101}$, the group exemplified as the chain-like alkyl group for $R^{101}$ is preferable. As the chain-like alkenyl group which may have a substituent for $R''^{103}$, the group exemplified as the chain-like alkenyl group for $R^{101}$ is preferable. $V''^{101}$ is preferably a fluorinated alkylene group having 1 to 3 carbon atoms, and particularly preferably —$CF_2$—, —$CF_2CF_2$—, —$CHFCF_2$—, —$CF(CF_3)CF_2$—, or —$CH(CF_3)CF_2$—.

In general formula (m-an-1), an1 represents 0 or 1.

General Formula (m-an-2)

In general formula (m-an-2), $R^{104}$ and $R^{105}$ each independently represent a cyclic group which may have a substituent, a chain-like alkyl group which may have a substituent, or a chain-like alkenyl group which may have a substituent, and respective examples thereof include the same groups as those exemplified for $R^{101}$ of general formula (m-an-1) However, $R^{104}$ and $R^{105}$ may be bonded to each other to form a ring.

As $R^{104}$ and $R^{105}$, a chain-like alkyl group which may have a substituent is preferable, and a linear or branched alkyl group, or a linear or branched fluorinated alkyl group is more preferable.

The chain-like alkyl group preferably has 1 to 10 carbon atoms, more preferably 1 to 7, and still more preferably 1 to 3. The carbon number of the chain-like alkyl group for $R^{104}$ and $R^{105}$ is preferably smaller among the aforementioned range of the carbon number, since solubility in a resist solvent is satisfactory. Also, with respect to the chain-like alkyl group for $R^{104}$ and $R^{105}$, it is preferred that the number of hydrogen atoms substituted with a fluorine atom is greater, because the acid strength becomes greater and transparency is improved with respect to high energy light equal to or lower than 200 nm or electron beams. The ratio of the fluorine atom in the chain-like alkyl group, that is, a fluorination rate, is preferably 70% to 100%, more preferably 90% to 100%, and most preferable is a perfluoroalkyl group in which all of hydrogen atoms are substituted with a fluorine atom.

In general formula (m-an-2), $V^{102}$ and $V^{103}$ each independently represent a single bond, an alkylene group, or a fluorinated alkylene group, and respective examples thereof include the same groups as those exemplified for $V^{101}$ of general formula (m-an-1).

In general formula (m-an-2), $L^{101}$ and $L^{102}$ each independently represent a single bond or an oxygen atom.

General Formula (m-an-3)

In general formula (m-an-3), $R^{106}$ to $R^{108}$ each independently represent a cyclic group which may have a substituent, a chain-like alkyl group which may have a substituent, or a chain-like alkenyl group which may have a substituent, and respective examples thereof include the same groups as those exemplified for $R^{101}$ of general formula (m-an-1).

$L^{103}$ to $L^{105}$ each independently represent a single bond, —CO—, or —SO$_2$—.

The component (B1) may use one type of the aforementioned acid generator or two or more types thereof in combination.

In the embodiment, in the case where the resist composition includes the component (B1), the content of the component (B1) is preferably 0.5 parts by mass to 60 parts by mass, more preferably 1 part by mass to 50 parts by mass, still more preferably 1 part by mass to 40 parts by mass with respect to 100 parts by mass of the component (A). If the content of the component (B1) is within the aforementioned range, pattern forming is sufficiently performed. Also, sensitivity can be further increased at the time of forming a resist pattern.

Photo-Reactive Quencher (D1)

The component (D1) is a component acting as a quencher (acid diffusion control agent) which traps acid generated from the component (B1) and the like upon exposure.

The component (D1) of the present invention is a photo-reactive quencher (D1) which is decomposed upon exposure and then loses the ability of controlling of acid diffusion.

Component (D1)

The component (D1) is not particularly limited as long as the component is decomposed upon exposure and then loses the ability of controlling of acid diffusion, and at least one compound selected from the group consisting of a compound represented by the following general formula (d1-1) (hereinafter, referred to as a "component (d1-1)"), a compound represented by the following general formula (d1-2) (hereinafter, referred to as a "component (d1-2)"), and a compound represented by the following general formula (d1-3) (hereinafter, referred to as a "component (d1-3)") is preferable.

The components (d1-1) to (d1-3) do not act as a quencher in the exposed portion since they are decomposed in the exposed portion to lose the ability of controlling of acid diffusion (basicity), but act as a quencher in the unexposed portion.

[Chemical formula 75]

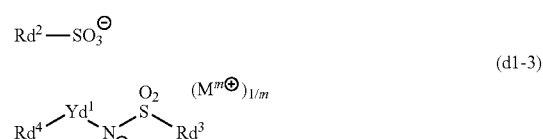

In the formulae, $Rd^1$ to $Rd^4$ represent a cyclic group which may have a substituent, a chain-like alkyl group which may have a substituent or a chain-like alkenyl group which may have a substituent, with the proviso that the carbon atom adjacent to the sulfur atom (shown in formula (d1-2)) in $Rd^2$ has no fluorine atom bonded thereto; $Yd^1$ represents a single bond or a divalent linking group; and each $M^{m+}$ independently represents an organic cation having a valence of m.

Component (d1-1)

Anion Moiety

In formula (d1-1), $Rd^1$ represents a cyclic group which may have a substituent, a chain-like alkyl group which may have a substituent or a chain-like alkenyl group which may have a substituent, and the same groups as those defined above for $R^{101}$ can be exemplified.

Among these, as the group for $Rd^1$, an aromatic hydrocarbon group which may have a substituent, an aliphatic cyclic group which may have a substituent and a chain-like alkyl group which may have a substituent are preferable. Examples of the substituent for these groups include a hydroxyl group, an oxo group, an alkyl group, an aryl group, a fluorine atom, a fluorinated alkyl group, a lactone-containing cyclic group represented by any one of the aforementioned formulae (a2-r-1) to (a2-r-7), an ether bond, an ester bond, and a combination thereof. In the case where an ether bond or an ester bond is included as the substituent, the substituent may be bonded via an alkylene group, and a linking group represented by any one of formulae (y-al-1) to (y-al-5) shown below is preferable.

The aromatic hydrocarbon group is preferably an aryl group such as a phenyl group or a naphthyl group.

Examples of the aliphatic cyclic group include a group in which one or more hydrogen atoms are removed from a polycycloalkane such as adamantane, norbornane, isobornane, tricyclodecane or tetracyclododecane.

As the chain-like hydrocarbon group, a chain-like alkyl group is preferable. The chain-like alkyl group preferably has 1 to 10 carbon atoms, and examples thereof include a linear alkyl group such as a methyl group, an ethyl group, a propyl group, a butyl group, a pentyl group, a hexyl group, a heptyl group, an octyl group, a nonyl group or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

In the case where the chain-like alkyl group is a fluorinated alkyl group having a fluorine atom or a fluorinated alkyl group as a substituent, the fluorinated alkyl group preferably has 1 to 11 carbon atoms, more preferably 1 to 8 carbon atoms, and still more preferably 1 to 4 carbon atoms. The fluorinated alkyl group may contain an atom other than a fluorine atom. Examples of the atom other than a fluorine atom include an oxygen atom, a carbon atom, a hydrogen atom, a sulfur atom and a nitrogen atom.

As $Rd^1$, a fluorinated alkyl group in which part or all of the hydrogen atoms constituting a linear alkyl group are substituted with fluorine atom(s) is preferable, and a fluorinated alkyl group in which all of the hydrogen atoms constituting a linear alkyl group are substituted with fluorine atoms (i.e., a linear perfluoroalkyl group) is more preferable.

Preferable examples of the anion moieties for the component (d1-1) are shown below.

[Chemical formula 76]

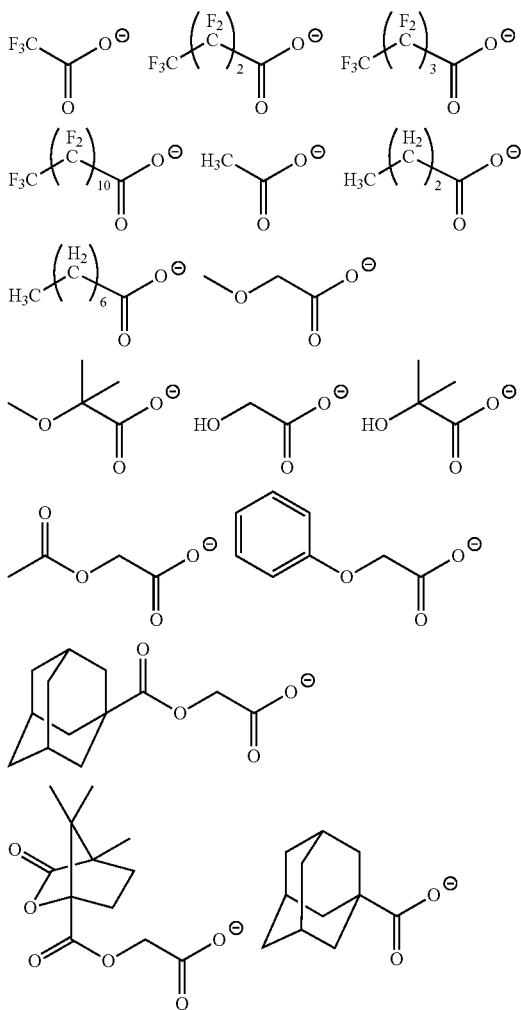

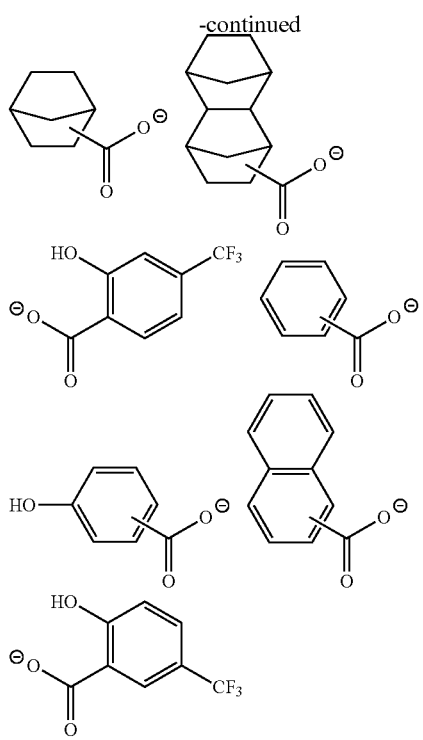

Cation Moiety

In formula (d1-1), $M^{m+}$ represents an organic cation having a valence of m (excluding the cation moiety of the compound (D0), as defined for $M^{m+}$ described later).

The organic cation for $M^{m+}$ is not particularly limited, and examples thereof include the same cation moieties as those represented by formulae (ca-1) to (ca-4) shown below, and cation moieties represented by formulae (ca-1-1) to (ca-1-63) shown below are preferable.

As the component (d1-1), one type of compound may be used, or two or more types of compounds may be used in combination.

Component (d1-2)

Anion Moiety

In formula (d1-2), $Rd^2$ represents a cyclic group which may have a substituent, a chain-like alkyl group which may have a substituent or a chain-like alkenyl group which may have a substituent, and the same groups as those defined above for $R^{110}$ can be exemplified, provided that the carbon atom adjacent to the sulfur atom in $Rd^2$ has no fluorine atom bonded thereto (i.e., the carbon atom adjacent to the sulfur atom (shown in formula (d1-2)) in $Rd^2$ is not substituted with a fluorine atom). As a result, the anion of the component (d1-2) becomes an appropriately weak acid anion, thereby improving the quenching ability of the component (D).

As $Rd^2$, an aliphatic cyclic group which may have a substituent is preferable, and a group in which one or more hydrogen atoms are removed from adamantane, norbornane, isobornane, tricyclodecane, tetracyclododecane or camphor (which may have a substituent) is more preferable.

The hydrocarbon group for $Rd^2$ may have a substituent. As the substituent, the same groups as those which the hydrocarbon group (e.g., aromatic hydrocarbon group, aliphatic hydrocarbon group) for $Rd^1$ in the formula (d1-1) may have as a substituent, which are described above, can be mentioned.

Preferable examples of the anion moieties for the component (d1-2) are shown below.

[Chemical formula 77]

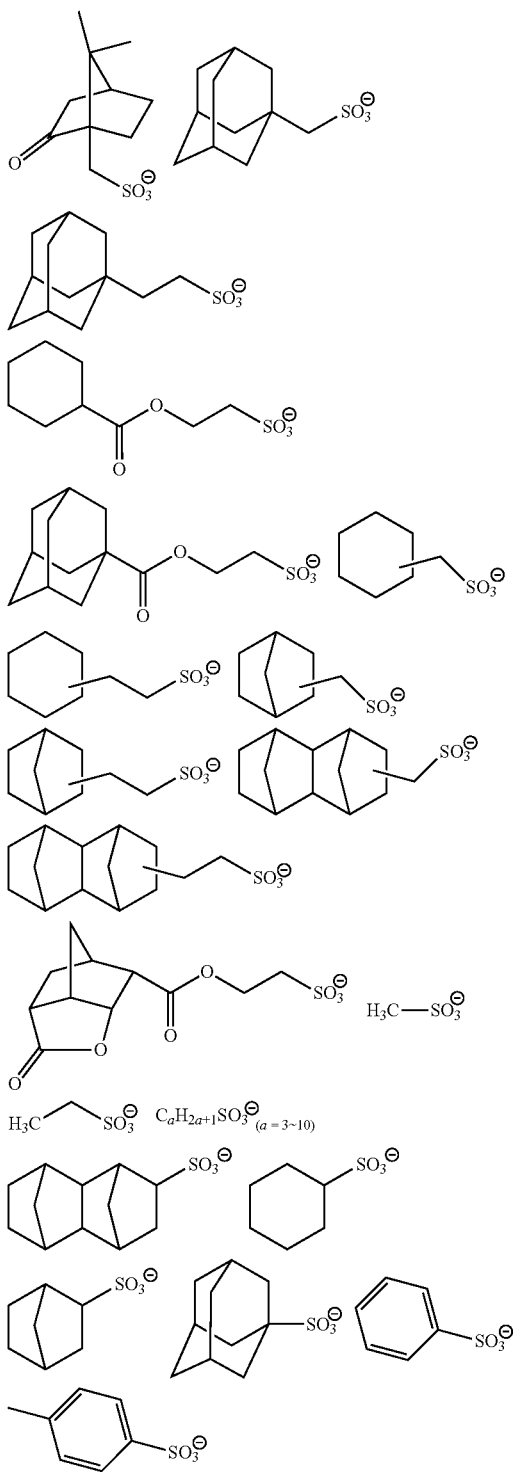

Cation Moiety

In formula (d1-2), $M^{m+}$ is an organic cation having a valence of m, and is the same as defined for $M^{m+}$ in the aforementioned formula (d1-1).

As the component (d1-2), one type of compound may be used, or two or more types of compounds may be used in combination.

Component (d1-3)
Anion Moiety

In formula (d1-3), $Rd^3$ represents a cyclic group which may have a substituent, a chain-like alkyl group which may have a substituent or a chain-like alkenyl group which may have a substituent, and the same groups as those defined above for $R^{101}$ can be exemplified, with a cyclic group containing a fluorine atom, a chain-like alkyl group or a chain-like alkenyl group being preferable. Among these, a fluorinated alkyl group is preferable, and the same fluorinated alkyl groups as those described above for $Rd^1$ are more preferable.

In formula (d1-3), $Rd^4$ represents a cyclic group which may have a substituent, a chain-like alkyl group which may have a substituent or a chain-like alkenyl group which may have a substituent, and the same groups as those defined above for $R^{101}$ can be exemplified.

Among these, an alkyl group which may have a substituent, an alkoxy group which may have a substituent, an alkenyl group which may have a substituent or a cyclic group which may have a substituent is preferable.

The alkyl group for $Rd^4$ is preferably a linear or branched alkyl group having 1 to 5 carbon atoms, and examples thereof include a methyl group, an ethyl group, a propyl group, an isopropyl group, an n-butyl group, an isobutyl group, a tert-butyl group, a pentyl group, an isopentyl group, and a neopentyl group. Part of the hydrogen atoms in the alkyl group for $Rd^4$ may be substituted with a hydroxyl group, a cyano group or the like.

The alkoxy group for $Rd^4$ is preferably an alkoxy group having 1 to 5 carbon atoms, and examples thereof include a methoxy group, an ethoxy group, an n-propoxy group, an iso-propoxy group, an n-butoxy group and a tert-butoxy group. Among these, a methoxy group and an ethoxy group are preferable.

As the alkenyl group for $Rd^4$, the same groups as those described above for $R^{101}$ can be mentioned, and a vinyl group, a propenyl group (an allyl group), a 1-methylpropenyl group and a 2-methylpropenyl group are preferable. These groups may further have an alkyl group having 1 to 5 carbon atoms or a halogenated alkyl group having 1 to 5 carbon atoms as a substituent.

As the cyclic group for $Rd^4$, the same groups as those described above for $R^{101}$ can be mentioned. Among these, as the cyclic group, an alicyclic group (e.g., a group in which one or more hydrogen atoms are removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $Rd^4$ is an alicyclic group, the resist composition can be satisfactorily dissolved in an organic solvent, thereby improving the lithography properties. Alternatively, when $Rd^4$ is an aromatic group, the resist composition exhibits excellent photoabsorption efficiency in a lithography process using EUV or the like as the exposure source, thereby resulting in the improvement of the sensitivity and the lithography properties.

In formula (d1-3), $Yd^1$ represents a single bond or a divalent linking group.

The divalent linking group for $Yd^1$ is not particularly limited, and examples thereof include a divalent hydrocarbon group (aliphatic hydrocarbon group, or aromatic hydrocarbon group) which may have a substituent and a divalent linking group containing a hetero atom. As such groups, the same divalent linking groups as those described above for Ya$^{21}$ in the formula (a2-1) can be mentioned.

As Yd$^1$, a carbonyl group, an ester bond, an amide bond, an alkylene group or a combination of these is preferable. As the alkylene group, a linear or branched alkylene group is more preferable, and a methylene group or an ethylene group is still more preferable.

Preferable examples of the anion moieties for the component (d1-3) are shown below.

[Chemical formula 78]

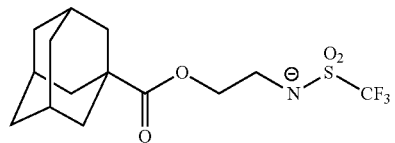
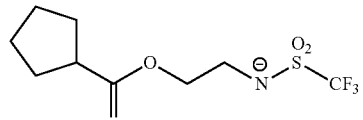
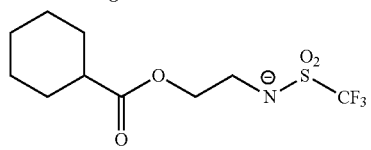
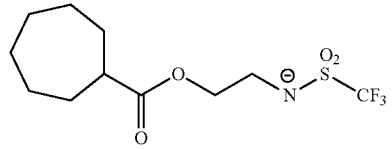
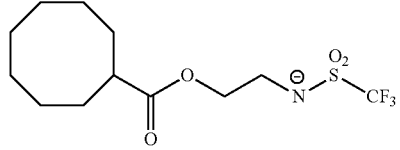
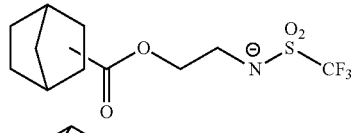
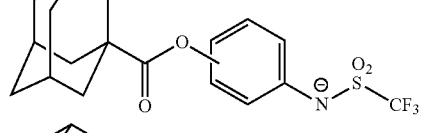
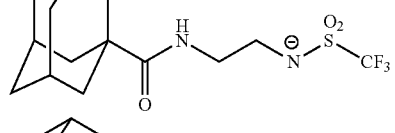
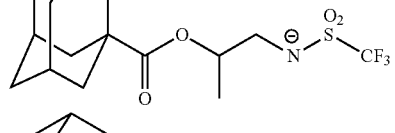
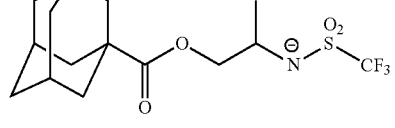

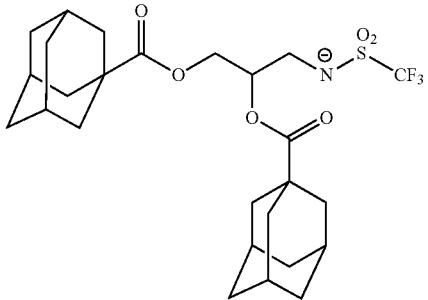
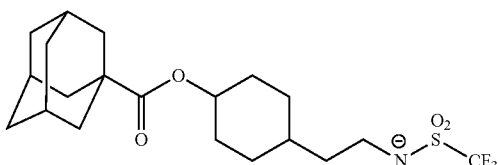
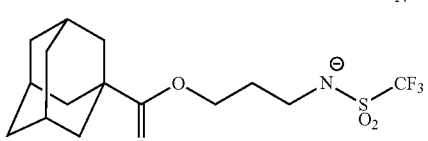
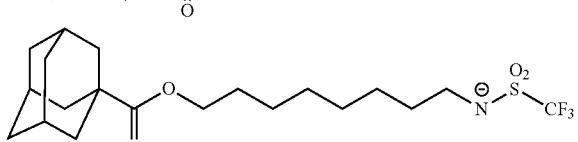
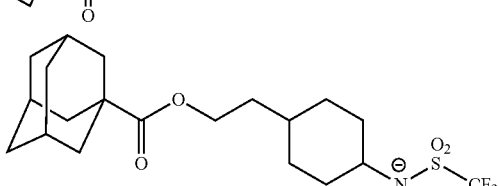
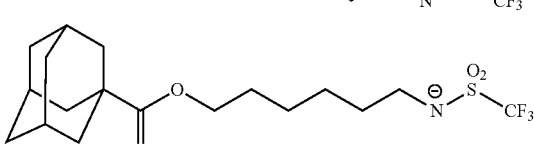

[Chemical formula 79]

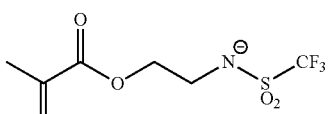
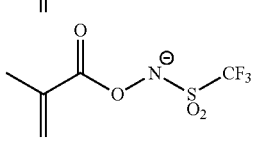
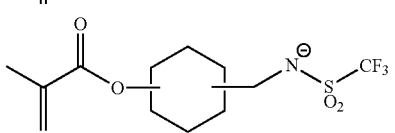
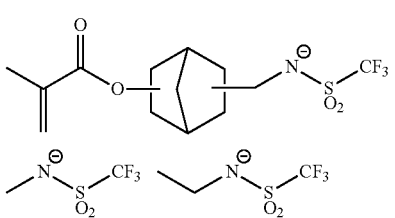

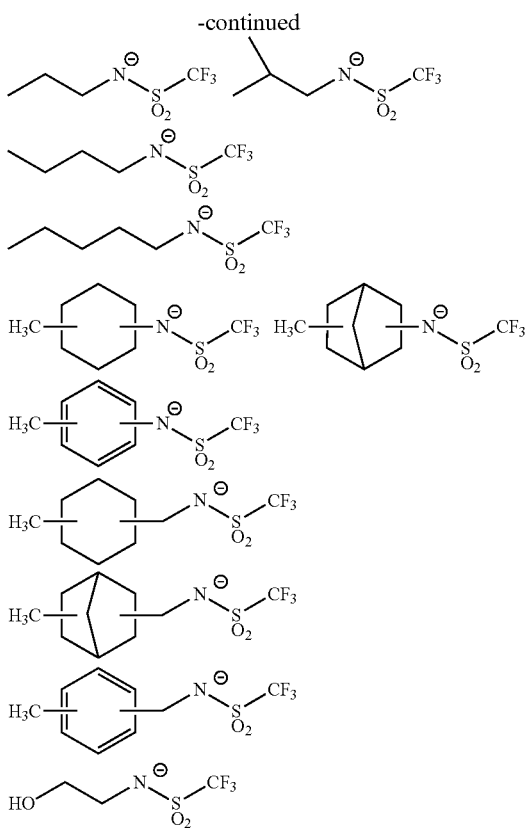

Cation Moiety

In formula (d1-3), $M^{m+}$ is an organic cation having a valence of m, and is the same as defined for $M^{m+}$ in the aforementioned formula (d1-1).

As the component (d1-3), one type of compound may be used, or two or more types of compounds may be used in combination.

As the component (D1), one type of the aforementioned components (d1-1) to (d1-3), or at least two types of the aforementioned components (d1-1) to (d1-3) can be used in combination.

The amount of the component (D1) relative to 100 parts by mass of the component (A) is preferably in a range from 0.5 parts by mass to 10 parts by mass, more preferably from 0.5 parts by mass to 8 parts by mass, and still more preferably from 1 part by mass to 8 parts by mass.

When the amount of the component (D1) is at least as large as the lower limit of the above-mentioned range, excellent lithography properties and excellent resist pattern shape can be obtained. On the other hand, when the amount of the component (D1) is no more than the upper limit of the above-mentioned range, sensitivity can be maintained at a satisfactory level, and through-put becomes excellent.

The production methods of the components (d1-1) to (d1-3) are not particularly limited, and the components (d1-1) to (d1-3) can be produced by conventional methods.

The amount of the component (D1) relative to 100 parts by mass of the component (A) is preferably in a range from 0.5 parts by mass to 15.0 parts by mass, more preferably from 0.5 parts by mass to 10.0 parts by mass, and still more preferably from 1.0 part by mass to 8.0 parts by mass. When the amount of at least as large as the lower limit of the above-mentioned range, excellent lithography properties and excellent resist pattern shape can be obtained. On the other hand, when the amount of the component (D) is no more than the upper limit of the above-mentioned range, sensitivity can be maintained at a satisfactory level, and through-put becomes excellent.

Component (D1-2)

The component (D1) may contain a nitrogen-containing organic compound (hereafter, referred to as component (D1-2)) which does not fall under the definition of component (D1).

The component (D1-2) is not particularly limited, as long as it functions as an acid diffusion control agent, and does not fall under the definition of the component (D1). As the component (D1-2), any of the conventionally known compounds may be selected for use. Among these, an aliphatic amine, particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include an amine in which at least one hydrogen atom of ammonia ($NH_3$) is substituted with an alkyl group or hydroxyalkyl group having no more than 12 carbon atoms (i.e., alkylamines or alkylalcoholamines), and a cyclic amine.

Examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines having 5 to 10 carbon atoms are preferable, and tri-n-pentylamine and tri-n-octylamine are particularly preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Examples of the aliphatic monocyclic amine include piperidine, and piperazine.

The aliphatic polycyclic amine preferably has 6 to 10 carbon atoms, and examples thereof include 1, 5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferable.

Further, as the component (D2), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonylpyrrolidine.

As the component (D1-2), one type of compound may be used alone, or two or more types may be used in combination.

The component (D1-2) is typically used in an amount in a range from 0.01 parts by mass to 5.0 parts by mass, relative to 100 parts by mass of the component (A). When the amount of the component (D) is in the above-mentioned range, the shape of the resist pattern and the stability with a lapse of time after resist coating and before exposure are improved.

As the component (D), one type of compound may be used, or two or more types of compounds may be used in combination.

When the resist composition of the present invention contains the component (D), the amount of the component (D) relative to 100 parts by mass of the component (A) is preferably in a range from 0.1 parts by mass to 15 parts by mass, more preferably from 0.3 parts by mass to 12 parts by mass, and still more preferably from 0.5 parts by mass to 12 parts by mass. When the amount of the component (D) is at least as large as the lower limit of the above-mentioned range, various lithography properties (such as LWR) of the resist composition are improved. Further, a resist pattern having an excellent shape can be obtained. On the other hand, when the amount of the component (D) is no more than the upper limit of the above-mentioned range, sensitivity can be maintained at a satisfactory level, and throughput becomes excellent.

Specific Compound (E)

In the embodiment, the resist composition can include at least one compound (E) (hereinafter, a component (E)), as an optional component, selected from the group consisting of organic carboxylic acid, phosphorus oxo acid, and a derivative thereof, for the purpose of preventing deterioration in sensitivity or improving the shape of the resist pattern and the stability with a lapse of time after resist coating and before exposure.

Preferred examples of the organic carboxylic acid include acetic acid, malonic acid, citric acid, malic acid, succinic acid, benzoic acid, and salicylic acid.

Examples of the phosphorus oxo acid include phosphoric acid, phosphonic acid, and phosphinic acid, and among these, phosphonic acid is preferable.

Examples of the phosphorus oxo acid derivative include an ester in which a hydrogen atom of the oxo acid is substituted with a hydrocarbon group, and examples of the hydrocarbon group include an alkyl group having 1 to 5 carbon atoms and an aryl group having 6 to 15 carbon atoms.

Examples of the phosphoric acid derivative include phosphoric acid esters such as di-n-butyl phosphate and diphenyl phosphate.

Examples of the phosphonic acid derivative include phosphonic acid esters such as dimethyl phosphonate, di-n-butyl phosphonate, phenylphosphonic acid, diphenyl phosphonate, and dibenzyl phosphonate.

Examples of the phosphinic acid derivative include phosphinic acid esters and phenylphosphinic acid.

As the component (E), one type may be used alone, or two or more types may be used in combination.

The component (E) is typically used in an amount within a range from 0.01 parts by mass to 5.0 parts by mass, with respect to 100 parts by mass of the component (A).

Component (F)

In the embodiment, the resist composition may include a fluorine additive (hereinafter, referred to as a "component (F)") in order to impart water repellency to the resist film.

As the component (F), for example, a fluorine-containing polymeric compound described in Japanese Unexamined Patent Application, Publication No. 2010-002870, Japanese Unexamined Patent Application, Publication No. 2010-032994, Japanese Unexamined Patent Application, Publication No. 2010-277043, Japanese Unexamined Patent Application, Publication No. 2011-13569, and Japanese Unexamined Patent Application, Publication No. 2011-128226 can be used.

Examples of the component (F) include polymers having a structural unit (f1) represented by general formula (f1-1) shown below. As the polymer, a polymer (homopolymer) consisting of a structural unit (f1) represented by formula (f1-1) shown below; a copolymer of a structural unit (f1) represented by formula (f1-1) shown below and the aforementioned structural unit (a1); and a copolymer of a structural unit (f1) represented by formula (f1-1) shown below, a structural unit derived from acrylic acid or methacrylic acid and the aforementioned structural unit (a1) are preferable. As the structural unit (a1) to be copolymerized with a structural unit (f1) represented by formula (f1-1) shown below, a structural unit derived from 1-ethyl-1-cyclooctyl (meth)acrylate or a structural unit represented by the aforementioned formula (a1-2-01) is preferable.

[Chemical formula 80]

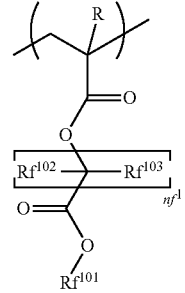

(f1-1)

In general formula (f1-1), R represents a hydrogen atom, an alkyl group having 1 to 5 carbon atoms, or a halogenated alkyl group having 1 to 5 carbon atoms. $Rf^{102}$ and $Rf^{103}$ each independently represent a hydrogen atom, a halogen atom, an alkyl group having 1 to 5 carbon atoms, or a halogenated alkyl group having 1 to 5 carbon atoms, and $Rf^{102}$ and $Rf^{103}$ may be the same as or different from each other. $nf^1$ represents an integer of 1 to 5, and $Rf^{101}$ represents an organic group including a fluorine atom.

In formula (f1-1), R is the same as defined above. As R, a hydrogen atom or a methyl group is preferable.

In formula (f1-1), examples of the halogen atom for $Rf^{102}$ and $Rf^{103}$ include a fluorine atom, a chlorine atom, a bromine atom and an iodine atom, and a fluorine atom is particularly preferable. Examples of the alkyl group having 1 to 5 carbon atoms for $Rf^{102}$ and $Rf^{103}$ include the same alkyl group having 1 to 5 carbon atoms as those described above for R, and a methyl group or an ethyl group is preferable. Examples of the halogenated alkyl group having 1 to 5 carbon atoms represented by $Rf^{102}$ or $Rf^{103}$ include groups in which part or all of the hydrogen atoms of the aforementioned alkyl groups of 1 to 5 carbon atoms are substituted with halogen atoms. Examples of the halogen atom include a fluorine atom, a chlorine atom, a bromine atom and an iodine atom, and a fluorine atom is particularly preferable. Among these, as $Rf^{102}$ and $Rf^{103}$, a hydrogen atom, a fluorine atom or an alkyl group having 1 to 5 carbon atoms is preferable, and a hydrogen atom, a fluorine atom, a methyl group or an ethyl group is more preferable.

In formula (f1-1), $nf^1$ represents an integer of 1 to 5, preferably an integer of 1 to 3, and more preferably 1 or 2.

In formula (f1-1), $Rf^{101}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and most preferably 1 to 10 carbon atoms.

It is preferable that the hydrocarbon group having a fluorine atom has 25% or more of the hydrogen atoms in the hydrocarbon group fluorinated, more preferably 50% or more, and most preferably 60% or more, as the hydrophobicity of the resist film during immersion exposure is enhanced.

Among these, as $Rf^{101}$, a fluorinated hydrocarbon group having 1 to 5 carbon atoms is preferable, and a methyl group, —$CH_2$—$CF_3$, —$CH_2$—$CF_2$—$CF_3$, —$CH(CF_3)_2$, —$CH_2$—$CH_2$—$CF_3$, and —$CH_2$—$CH_2$—$CF_2$—$CF_2$—$CF_2$—$CF_3$ are most preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern become satisfactory.

Further, the dispersity (Mw/Mn) of the component (F) is preferably 1.0 to 5.0, more preferably 1.0 to 3.0, and most preferably 1.2 to 2.5.

As the component (F), one type may be used alone, or two or more types may be used in combination.

The component (F) is typically used in an amount within a range from 0.5 parts by mass to 10 parts by mass, relative to 100 parts by mass of the component (A).

If desired, other miscible additives can also be added to the resist composition of the present invention. Examples of such miscible additives include additive resins for improving the performance of the resist film, dissolution inhibitors, plasticizers, stabilizers, colorants, halation prevention agents, and dyes.

Component (S)

The resist composition according to the present embodiment can be prepared by dissolving the materials for the resist composition in an organic solvent (hereafter, frequently referred to as a "component (S)").

The component (S) may be any organic solvent which can dissolve the respective components to give a uniform solution, and one or more kinds of any organic solvent can be appropriately selected from those conventionally known as solvents for a chemically amplified resist.

Examples thereof include lactones such as γ-butyrolactone; ketones such as acetone, methyl ethyl ketone (MEK), cyclohexanone, methyl-n-pentyl ketone (2-heptanone) and methyl isopentyl ketone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

These solvents can be used individually, or in combination as a mixed solvent.

Among these, PGMEA, PGME, γ-butyrolactone and EL are preferable.

Further, among the mixed solvents, a mixed solvent obtained by mixing PGMEA with a polar solvent is preferable. The mixing ratio (mass ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL or cyclohexanone is mixed as the polar solvent, the PGMEA:EL or cyclohexanone mass ratio is preferably from 1:9 to 9:1, and more preferably from 2:8 to 8:2. Alternatively, when PGME is mixed as the polar solvent, the PGMEA:PGME mass ratio is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate according to a coating thickness. In general, the organic solvent is used in an amount such that the solid content concentration of the resist composition becomes within the range from 1 mass % to 20 mass %, and preferably from 2 mass % to 15 mass %.

Second Embodiment

A second embodiment of the present invention will be described.

A positive-type resist composition according to the second embodiment which generates an acid upon exposure and whose solubility in an alkali developing solution increases under the action of an acid includes a base material component (A) whose solubility in an alkali developing solution increases under the action of an acid (hereinafter, referred to as a "component (A)"), an acid generator component (B2) which generates an acid upon exposure (hereinafter, referred to as a "component (B2)"), and a photo-reactive quencher (D2) (hereinafter, referred to as a "component (D2)"), in which the photo-reactive quencher (D2) includes a compound (m) represented by general formula (m0).

The positive-type resist composition of the second embodiment includes the photo-reactive quencher (D2) and the component (D2) includes a compound (m) represented by general formula (m0).

In the second embodiment, the compound (m0) functions as a photo-reactive quencher. The photo-reactive quencher (D2) acts as a quencher (acid diffusion control agent) which traps an acid generated from the component (B2).

Component (A)

The description for the component (A) according to the second embodiment is the same as the description for the component (A) according to the first embodiment.

Component (B2)

The component (B2) according to the second embodiment will be described. The component (B2) is not particularly limited, and any known compound as an acid generator for a chemically amplified-type resist can be used.

Examples of the acid generator include an onium salt-based acid generator such as an iodonium salt and a sulfonium salt, an oxime sulfonate-based acid generator, a diazomethane-based acid generator such as bisalkyl or bisaryl sulfonyl diazomethanes and poly(bissulfonyl)diazomethanes, a nitrobenzyl sulfonate-based acid generator, an iminosulfonate-based acid generator, and a disulfone-based acid generator. Among these, an onium salt-based acid generator is preferably used.

As the onium salt-based acid generator, for example, a compound represented by general formula (b-1) shown below (hereinafter, referred to as a "component (b-1)"), a compound represented by general formula (b-2) (hereinafter, referred to as a "component (b-2)"), or a compound represented by general formula (b-3) (hereinafter, referred to as a "component (b-3)") can be used.

[Chemical formula 81]

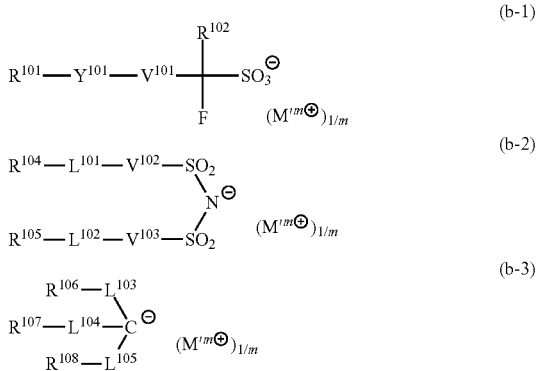

In general formulae (b-1) to (b-3), $R^{101}$ and $R^{104}$ to $R^{108}$ each independently represent a cyclic group which may have a substituent, a chain-like alkyl group which may have a substituent, or a chain-like alkenyl group which may have a substituent. $R^{104}$ and $R^{105}$ may be bonded to each other to form a ring. Two of either $R^{106}$ or $R^{107}$ may be bonded to each other to form a ring. $R^{102}$ represents a fluorine atom or a fluorinated alkyl group having 1 to 5 carbon atoms. $Y^{101}$ represents a single bond or a divalent linking group including an oxygen atom. $V^{101}$ to $V^{103}$ each independently represent a single bond, an alkylene group, or a fluorinated alkylene group. $L^{101}$ and $L^{102}$ each independently represent a single bond or an oxygen atom. $L^{103}$ to $L^{105}$ each independently represent a single bond, —CO—, or —SO$_2$—. $M'^{m+}$ represents an organic cation having a valence of m.

Anion Moiety

Anion Moiety of Component (b-1)

In general formula (b-1), the description for $R^{101}$, $Y^{101}$, $V^{101}$, and $R^{102}$ is the same as the description for the anion moiety represented by general formula (m-an-1).

Anion Moiety of Component (b-2)

In general formula (b-2), the description for $R^{104}$ and $R^{105}$, $L^{101}$ and $L^{102}$, and $V^{102}$ and $V^{103}$ is the same as the description for the anion moiety represented by general formula (m-an-2)

Anion Moiety of Component (b-3)

In general formula (b-3), the description for $R^{106}$ to $R^{108}$, and $L^{103}$ to $L^{105}$ is the same as the description for the anion moiety represented by general formula (m-an-3).

Cation Moiety

In general formulae (b-1), (b-2), and (b-3), $M'^{m+}$ represents an organic cation having a valence of m, among these, a sulfonium cation or iodonium cation is preferable, and the cation represented by any one of general formulae (ca-1) to (ca-4) shown below is particularly preferable.

[Chemical formula 82]

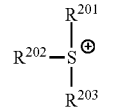 (ca-1)

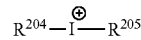 (ca-2)

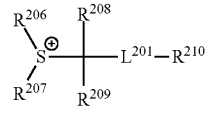 (ca-3)

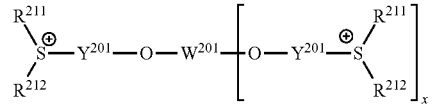 (ca-4)

In general formulae (ca-1) to (ca-4), $R^{201}$ to $R^{207}$ and $R^{211}$ and $R^{212}$ each independently represent an aryl group which may have a substituent, an alkyl group, or an alkenyl group; and $R^{201}$ to $R^{203}$, $R^{206}$ and $R^{207}$, and $R^{211}$ and $R^{212}$ may be bonded to each other to form a ring with a sulfur atom in the formula. $R^{208}$ and $R^{209}$ each independently represent a hydrogen atom or an alkyl group having 1 to 5 carbon atoms; $R^{210}$ represents an aryl group which may have a substituent, an alkyl group, an alkenyl group, or a —SO$_2$-containing cyclic group; $L^{201}$ represents —C(=O)— or —C(=O)—O—; each $Y^{201}$ independently represents an arylene group, an alkylene group, or an alkenylene group; x represents 1 or 2; and $W^{201}$ represents a linking group having a valence of (x+1)

Examples of the aryl group for $R^{201}$ to $R^{207}$ and $R^{211}$ and $R^{212}$ include an unsubstituted aryl group having 6 to 20 carbon atoms, and a phenyl group or a naphthyl group is preferable.

The alkyl group for $R^{201}$ to $R^{207}$ and $R^{211}$ and $R^{212}$ may be a chain-like or cyclic alkyl group, and preferably has 1 to 30 carbon atoms.

The alkenyl group for $R^{201}$ to $R^{207}$ and $R^{211}$ and $R^{212}$ preferably has 2 to 10 carbon atoms.

Examples of the substituent which $R^{201}$ to $R^{207}$ and $R^{210}$ to $R^{212}$ may include an alkyl group, a halogen atom, a halogenated alkyl group, a carbonyl group, a cyano group, an amino group, an aryl group, an arylthio group, and the group represented by any one of the following general formulae (ca-r-1) to (ca-r-7) shown below.

Examples of the aryl group in the arylthio group as the substituent include the same groups as those exemplified for $R^{101}$, and specifically, a phenylthio group or a biphenylthio group can be exemplified.

[Chemical formula 83]

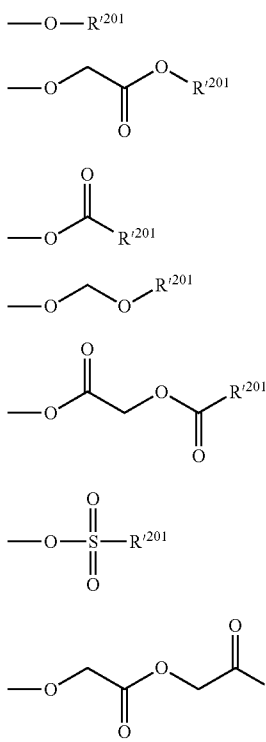

In general formulae (ca-r-1) to (ca-r-7), each $R'^{201}$ independently represents a hydrogen atom, a cyclic group which may have a substituent, a chain-like alkyl group, or a chain-like alkenyl group.

Examples of the cyclic group which may have a substituent, a chain-like alkyl group which may have a substituent, or a chain-like alkenyl group which may have a substituent for $R'^{201}$ include the same groups as those exemplified for $R^{101}$ in general formula (b-1), and additionally, examples of the cyclic group which may have a substituent or the chain-like alkyl group which may have a substituent include the same group as the acid dissociable group represented by general formula (a1-r-2).

In the case where $R^{201}$ to $R^{203}$, $R^{206}$ to $R^{207}$, and $R^{211}$ to $R^{212}$ are bonded to each other to form a ring with a sulfur atom in the formula, they may be bonded to each other via a hetero atom such as a sulfur atom, an oxygen atom, and a nitrogen atom, or a functional group such as a carbonyl group, —SO—, —SO$_2$—, —SO$_3$—, —COO—, —CONH— and —N(R$_N$)— (R$_N$ represents an alkyl group having 1 to 5 carbon atoms). As the ring to be formed, one ring including a sulfur atom of the formula in its ring structure is preferably a 3- to 10-membered ring and particularly preferably 5- to 7-membered ring, including a sulfur atom. Examples of the ring to be formed include a thiophene ring, a thiazole ring, a benzothiophene ring, a thianthrene ring, a benzothiophene ring, a dibenzothiophene ring, a 9H-thioxanthene ring, a thioxanthone ring, a thianthrene ring, a phenoxanthine ring, a tetrahydrothiophenium ring, and a tetrahydrothiopyranium ring.

$R^{208}$ to $R^{209}$ each independently represent a hydrogen atom or an alkyl group having 1 to 5 carbon atoms, and a hydrogen atom or an alkyl group having 1 to 3 carbon atoms is preferable, and $R^{208}$ to $R^{209}$ may be bonded to each other to form a ring in the case where $R^{208}$ to $R^{209}$ represent an alkyl group.

$R^{210}$ represents an aryl group which may have a substituent, an alkyl group which may have a substituent, an alkenyl group which may have a substituent, or a —SO$_2$-containing cyclic group which may have a substituent.

Examples of the aryl group for $R^{210}$ include an unsubstituted aryl group having 6 to 20 carbon atoms, and a phenyl group or a naphthyl group is preferable.

The alkyl group for $R^{210}$ may be a chain-like or cyclic alkyl group, and preferably has 1 to 30 carbon atoms.

The alkenyl group for $R^{210}$ preferably has 2 to 10 carbon atoms.

Examples of the —SO$_2$-containing cyclic group which may have a substituent for $R^{210}$ include the same "—SO$_2$-containing cyclic group" as that exemplified for Ra$^{21}$ in general formula (a2-1), and a group represented by general formula (a5-r-1) is preferable.

Each $Y^{201}$ independently represents an arylene group, an alkylene group or an alkenylene group.

Examples of the arylene group for $Y^{201}$ include a group in which one hydrogen atom is removed from the aryl group exemplified as the aromatic hydrocarbon group for $R^{101}$ in general formula (b-1).

Examples of the alkylene group and alkenylene group for $Y^{201}$ include the same group as the aliphatic hydrocarbon group exemplified as the divalent hydrocarbon group for Va$^1$ in general formula (a1-1).

In general formula (ca-4), x represents 1 or 2.

$W^{201}$ represents a linking group having a valence of (x+1), that is divalent or trivalent.

As the divalent linking group for $W^{201}$, a divalent hydrocarbon group which may have a substituent is preferable, and the same hydrocarbon group for Ya$^{21}$ in general formula (a2-1) can be exemplified. The divalent linking group for $W^{201}$ may be linear, branched, or cyclic, and is preferably cyclic. Among these, a group in which two carbonyl groups are bonded to the both terminals of an arylene group is preferable. Examples of the arylene group include a phenylene group and a naphtylene group, and a phenylene group is particularly preferable.

Examples of the trivalent linking group for $W^{201}$ include a group in which one hydrogen atom is removed from the divalent linking group for the $W^{201}$ and a group in which the divalent linking group is further bonded to the divalent linking group. As the trivalent linking group for $W^{201}$, a group in which two carbonyl groups are bonded to an arylene group is preferable.

Preferred examples of cation represented by general formula (ca-1) include the cation represented by any one of formulae (ca-1-1) to (ca-1-63) shown below.

[Chemical formula 84]

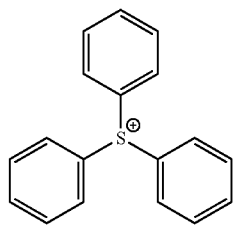

(ca-1-1)

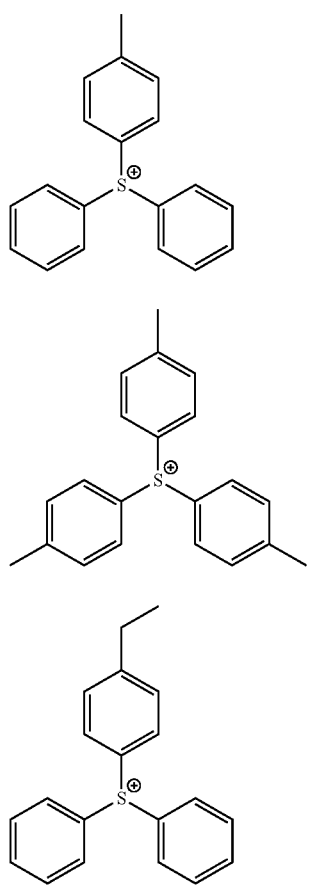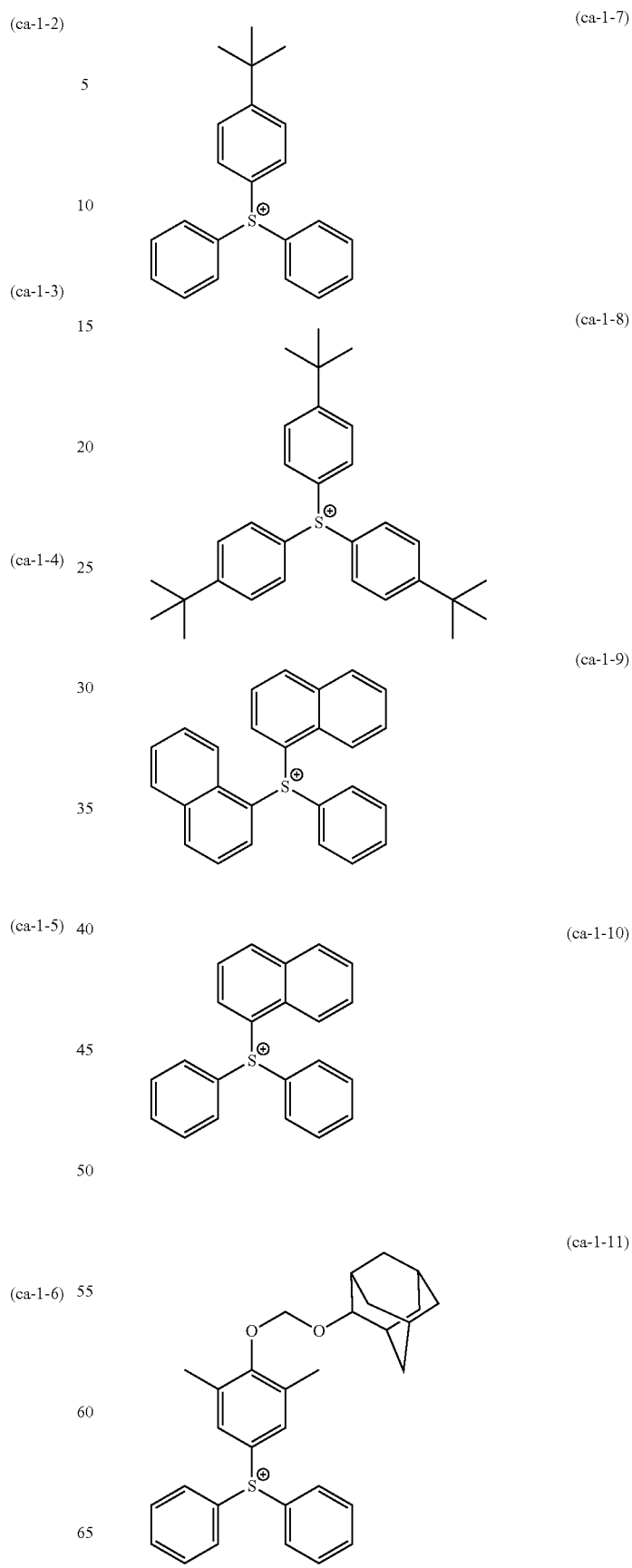

(ca-1-12) 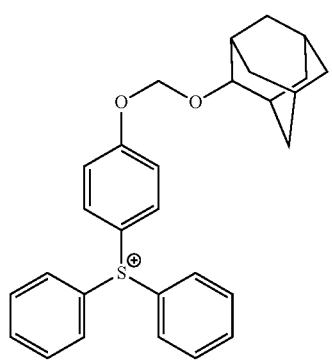
(ca-1-13) 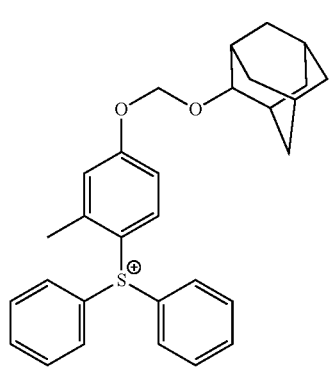
(ca-1-14) 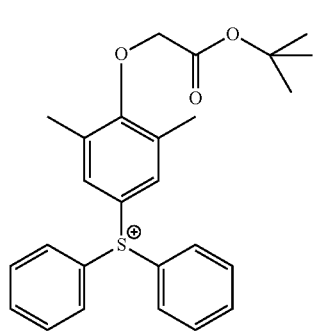
(ca-1-15) 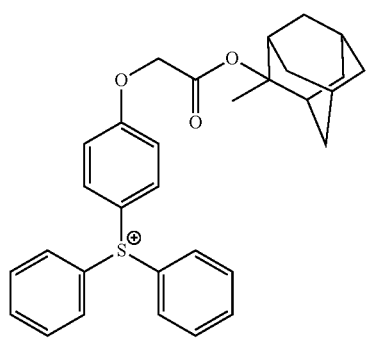
(ca-1-16) 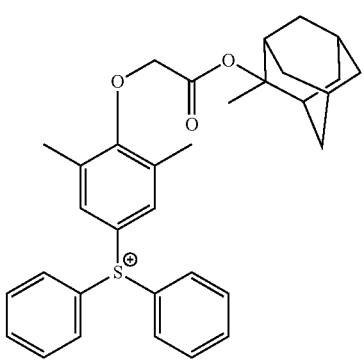
[Chemical formula 85]
(ca-1-17) 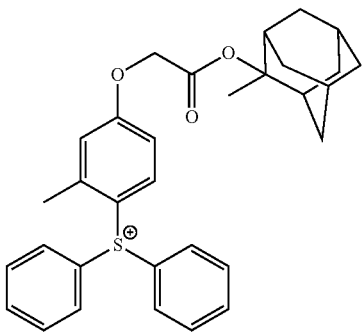
(ca-1-18) 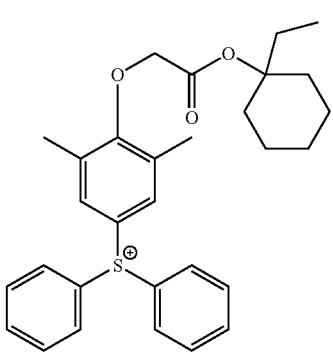
(ca-1-19) 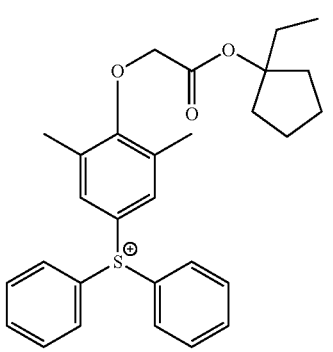

(ca-1-20)
(ca-1-21)
(ca-1-22)
(ca-1-23)
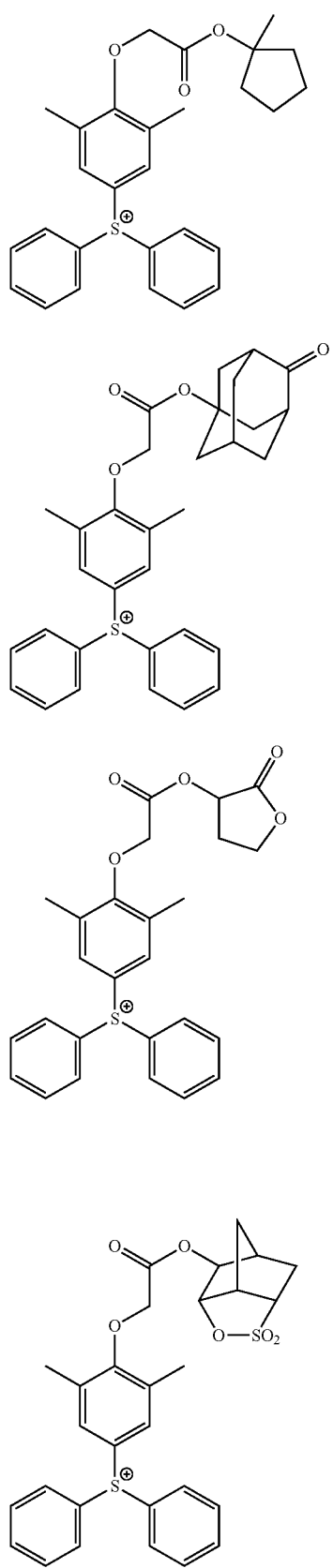
(ca-1-24)
(ca-1-25)
(ca-1-26)
(ca-1-27)
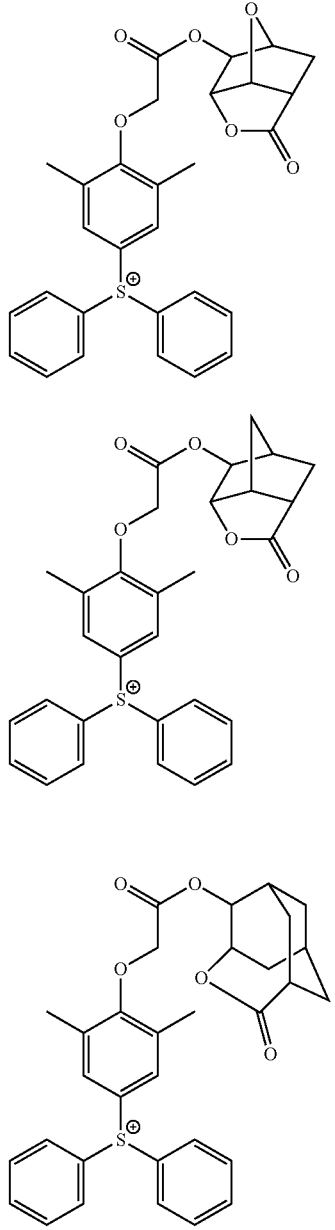
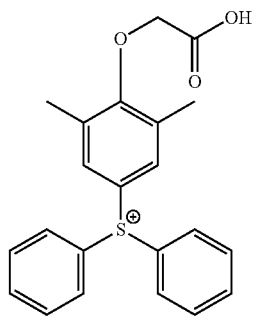

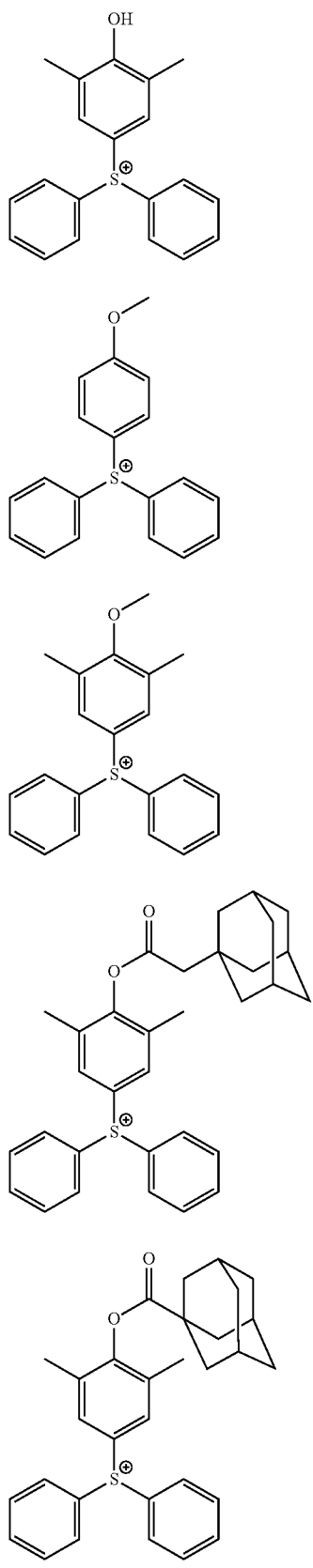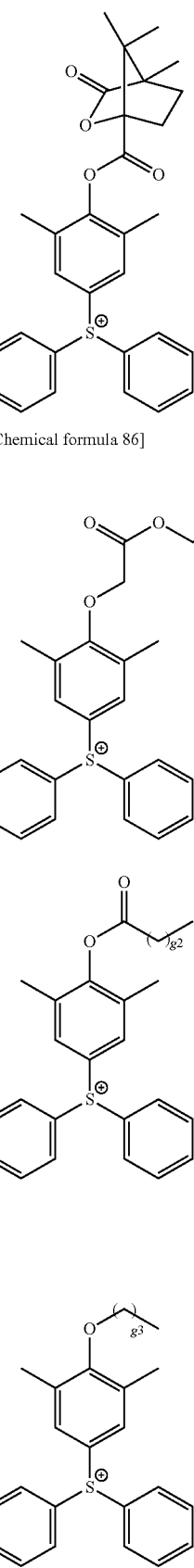
[Chemical formula 86]

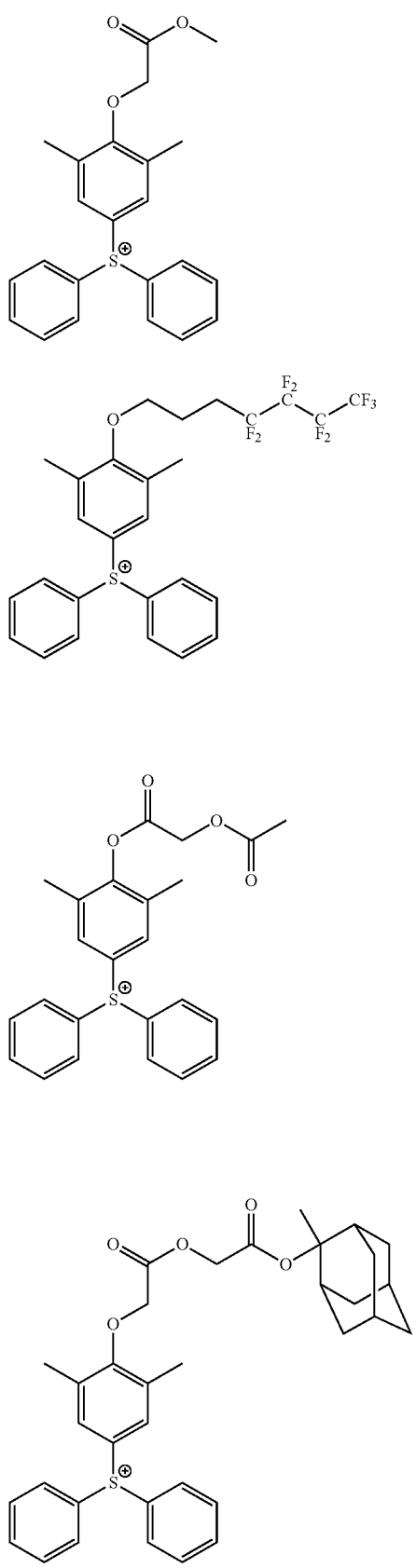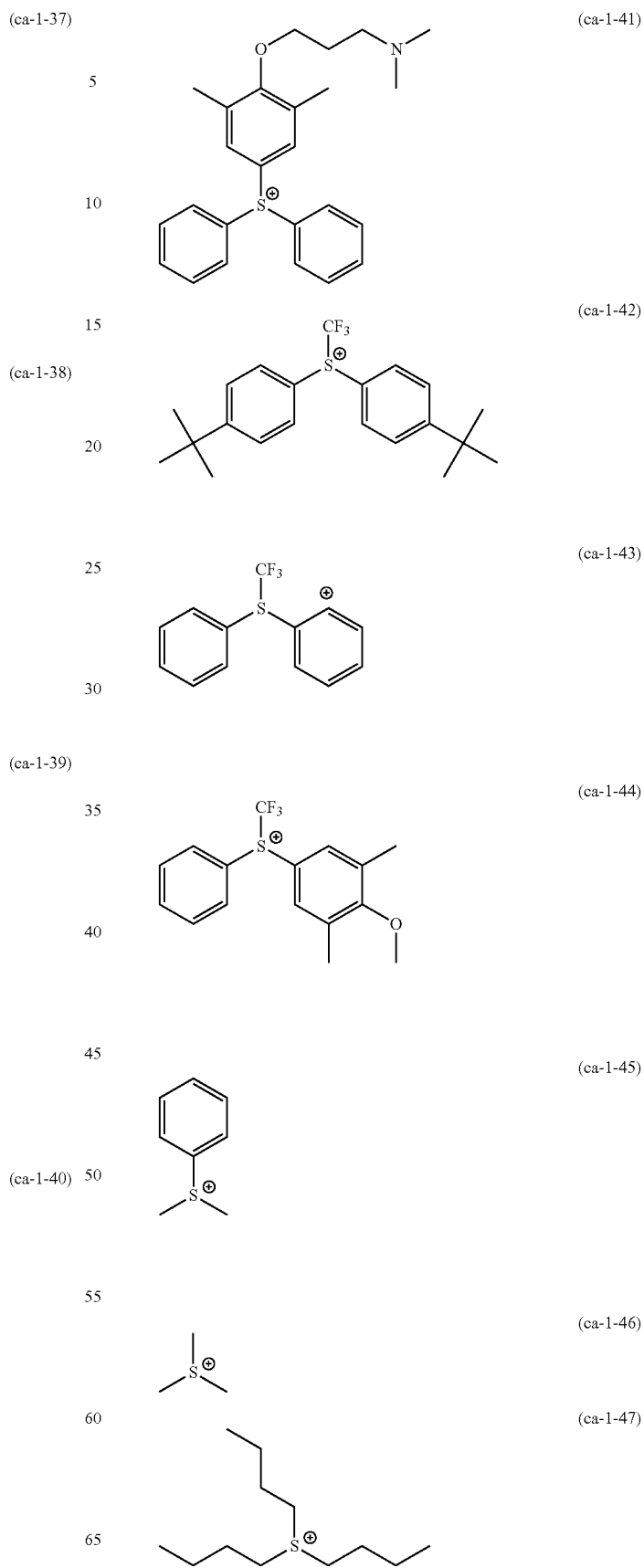

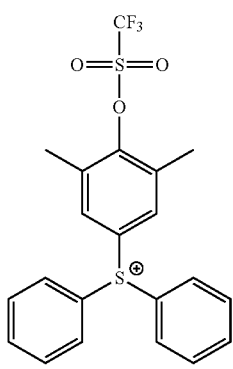
(ca-1-48)
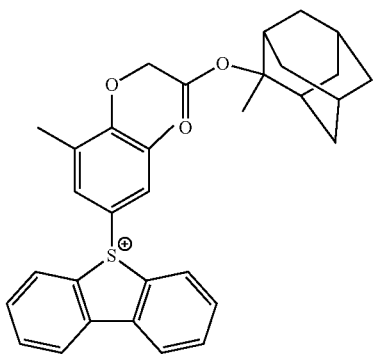
(ca-1-52)
(ca-1-53)
(ca-1-54)
(ca-1-55)
In formulae (ca-1-34) to (ca-1-36), g1, g2, and g3 represent a repeating number; g1 represents an integer of 1 to 5; g2 represents an integer of 0 to 20; and g3 represents an integer of 0 to 20.
[Chemical formula 87]
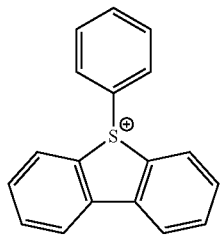
(ca-1-49)
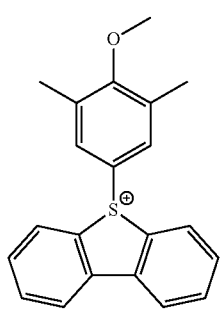
(ca-1-50)
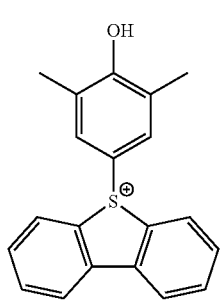
(ca-1-51)
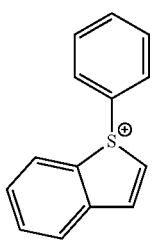
(ca-1-56)

(ca-1-57) 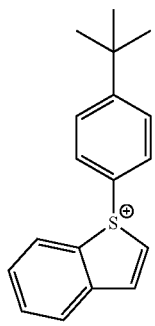

(ca-1-58) 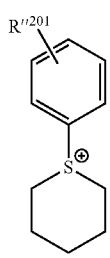

(ca-1-59) 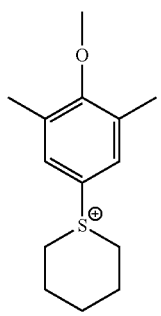

(ca-1-60) 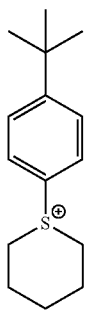

(ca-1-61) 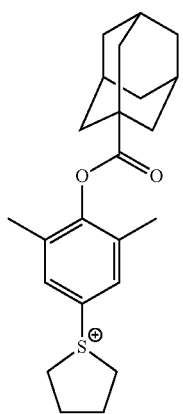

(ca-1-62) 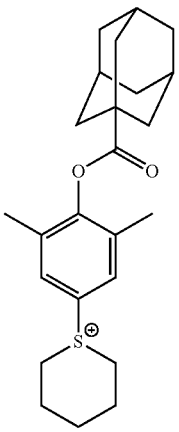

(ca-1-63) 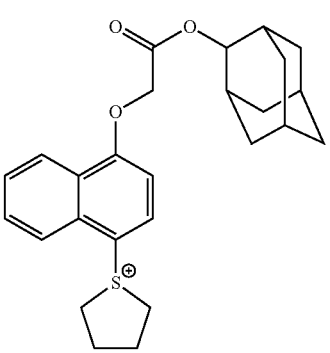

In formula (ca-1-58), $R''^{201}$ represents a hydrogen atom or a substituent; and examples of the substituent include the same substituents as those which $R^{201}$ to $R^{207}$ and $R^{210}$ to $R^{212}$ may have.

Preferred examples of the cation represented by general formula (ca-3) include the cation represented by any one of the following general formulae (ca-3-1) to (ca-3-6).

[Chemical formula 88]

(ca-3-1) 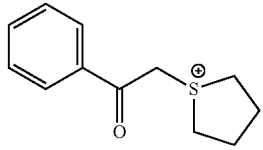

(ca-3-2) 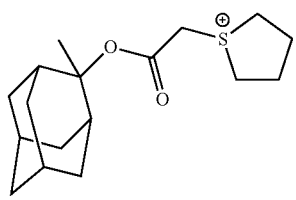

(ca-3-3) 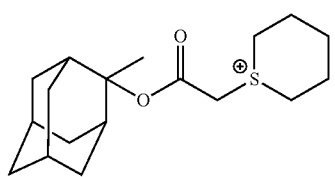

-continued (ca-3-4)
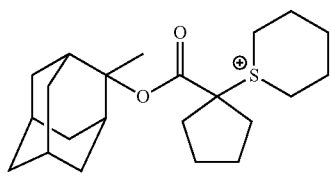

(ca-3-5)
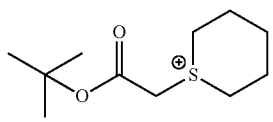

(ca-3-6)
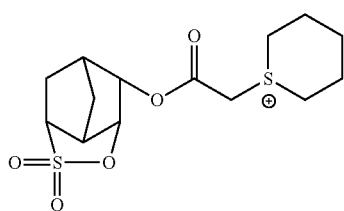

Preferred examples of the cation represented by general formula (ca-4) include the cation represented by any one of the following chemical formulae (ca-4-1) to (ca-4-2).

[Chemical formula 89]

(ca-4-1)
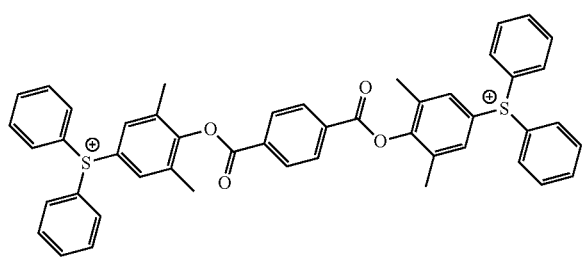

(ca-4-2)
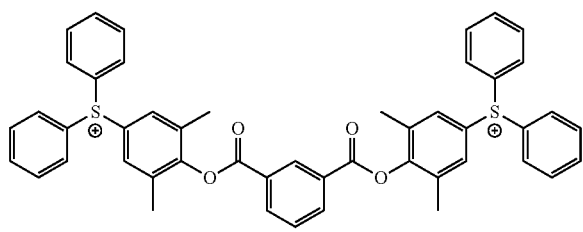

As the component (B2), one type of the aforementioned acid generator may be used alone, or two or more types thereof may be used in combination.

In the embodiment, in the case where the resist composition contains a component (B2), the content of the component (B2) is preferably 0.5 parts by mass to 60 parts by mass, more preferably 1 part by mass to 50 parts by mass, and still more preferably 1 part by mass to 40 parts by mass with respect to 100 parts by mass of the component (A). If the content of the component (B2) is set to the aforementioned range, pattern forming is sufficiently performed. Also, when respective components of the resist composition are dissolved in an organic solvent, a uniform solution is obtained, and storage stability becomes excellent, which is preferable.

Photo-Reactive Quencher (D2)

The component (D2) acts as a quencher (acid diffusion control agent) which traps an acid generated from the component (B2), and includes a compound (m) represented by general formula (m0). In the second embodiment, the compound (m) is preferably a compound represented by the following general formula (m0-2).

[Chemical formula 90]

(m0-2)
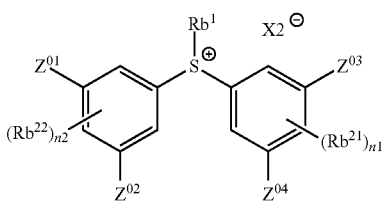

In general formula (m0-1), $Z^{01}$ to $Z^{04}$ each independently represent a substituent having electron withdrawing properties, $Rb^{21}$ and $Rb^{22}$ each independently represent an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^1$ represents an aryl group which may have a substituent, an alkyl group which may have a substituent, or an alkenyl group which may have a substituent, n1 and n2 each independently represent an integer of 0 to 3, and $X2^-$ represents an organic anion which can generate weak acid.

In general formula (m0-2), the description for $Z^{01}$ to $Z^{04}$, $Rb^{21}$, $Rb^{22}$, $Rb^1$, and n1 and n2 is the same as the description for general formula (m0).

In general formula (m0-2), $X2^-$ represents an organic anion which can generate weak acid.

The "weak acid" used herein refers to an acid having an acid strength weaker than the acid generated from the component (B2), and has the acid dissociation constant (pKa) of 0 or more and preferably 0.2 or more. The upper limit thereof is not particularly set, but the upper limit thereof is substantially about 10.

More specifically, as $X1^-$ of general formula (m0-1), the anion represented by an organic anion represented by any one of the following general formulae (d1-an-1) to (d1-an-3) is preferable.

[Chemical formula 91]

(d1-an-1)
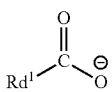

(d1-an-2)
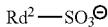

(d1-an-3)
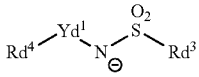

In the formulae, $Rd^1$ to $Rd^4$ represent a cyclic group which may have a substituent, a chain-like alkyl group which may have a substituent, or a chain-like alkenyl group which may have a substituent. However, two or more fluorine atoms are not bonded to a carbon atom adjacent to the S atom (shown in formula (d1-an-2)) in $Rd^2$. $Yd^1$ represents a single bond or a divalent linking group.

The description for $Rd^1$ to $Rd^4$ of general formulae (d1-an-1) to (d1-an-3) is the same as the description for $Rd^1$ to $Rd^4$ of general formulae (d1-1) to (d1-3).

As the component (D2), one type of the aforementioned components (d1-1) to (d1-3) may be used alone, or two or more types thereof may be used in combination.

The content of the component (D2) is preferably 0.5 parts by mass to 10 parts by mass, 0.5 parts by mass to 8 parts by mass, and 1 part by mass to 8 parts by mass with respect to 100 parts by mass of the component (A).

When the content of the component (D2) is equal to or less than the lower limit, particularly excellent lithography properties and a resist pattern shape can be obtained. On the other hand, when the content of the component (D2) is equal to or more than the upper limit, sensitivity can be maintained at a satisfactory level, and through-put becomes excellent. In addition, sensitivity at the time of forming a resist pattern can be further increased.

Components (E) to (F)

In the second embodiment, the components (E) to (F) are preferably included in the same manner as the first embodiment.

Positive-Type Resist Composition

The positive-type resist composition according to the second aspect of the present invention is a positive-type resist composition which generates an acid upon exposure and whose solubility in a developing solution increases under the action of an acid, and the positive-type resist composition includes a base material component (A) whose solubility in a developing solution increases under the action of an acid, in which the base material component (A) includes a resin component (A2), and the resin component (A2) has a structural unit (a6) derived from a compound represented by the following general formula (a6-1).

[Chemical formula 92]

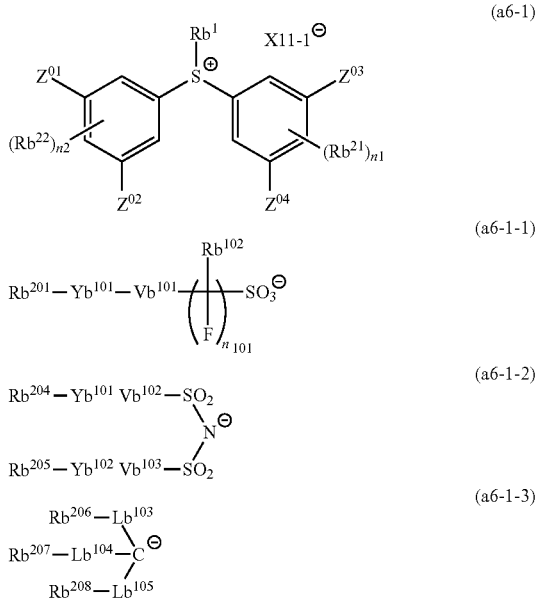

In formula (a6-1), $Z^{01}$ to $Z^{04}$ each independently represent a substituent having electron withdrawing properties, $Rb^{21}$ and $Rb^{22}$ each independently represent an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^1$ represents an aryl group which may have a substituent, an alkyl group which may have a substituent, or an alkenyl group which may have a substituent, and n1 and n2 each independently represent an integer of 0 to 3.

$X11\text{-}1^-$ represents an organic anion represented by any one of general formulae (a6-1-1) to (a6-1-3). In formulae (a6-1-1) to (a6-1-3), $Rb^{201}$ represents a chain-like alkenyl group which may have a substituent, and $Rb^{204}$ to $Rb^{205}$ each independently represent a cyclic group which may have a substituent, a chain-like alkyl group which may have a substituent, or a chain-like alkenyl group which may have a substituent, with the proviso that at least one of $Rb^{204}$ to $Rb^{205}$ represents a chain-like alkenyl group which may have a substituent. $Rb^{206}$ to $Rb^{208}$ each independently represent a cyclic group which may have a substituent, a chain-like alkyl group which may have a substituent, or a chain-like alkenyl group which may have a substituent, with the proviso that at least one of $Rb^{206}$ to $Rb^{208}$ represents a chain-like alkenyl group which may have a substituent. $Rb^{102}$ represents a fluorine atom or a fluorinated alkyl group having 1 to 5 carbon atoms. $Yb^{101}$ represents a single bond or a divalent linking group including an oxygen atom. $Vb^{101}$ to $Vb^{103}$ each independently represent a single bond, an alkylene group, a fluorinated alkylene group, an arylene group, or a fluorinated arylene group. $L^{101}$ to $L^{102}$ each independently represent a single bond or an oxygen atom. $Lb^{103}$ to $Lb^{105}$ each independently represent a single bond, —CO—, or —SO$_2$—. $n_{101}$ represents 0 or 1.

Resin Component (A2)

In the positive-type resist composition according to the second aspect of the present invention, the base material component (A) includes a resin component (A2) having a structural unit (a6) derived from a compound having an anion group which generates an acid upon exposure and a cation moiety of the compound represented by general formula (m0). The resin component (A2) (hereinafter, may be referred to as a "component (A2)") is a polymeric compound having a structural unit (a6) including the anion group which generates an acid upon exposure on a side chain and the cation moiety of the compound represented by general formula (m0).

Structural Unit (a6)

The structural unit (a6) is represented by general formula (a6-1).

Cation Moiety of the Compound Represented by General Formula (a6-1)

The description for $Z^{01}$ to $Z^{04}$, $Rb^{21}$, $Rb^{22}$, $Rb^1$, and n1 and n2 of general formula (a6-1) is the same as the description for general formula (m0).

Examples of $Rb^{201}$ of formula (a6-1-1) include the same group as the chain-like alkenyl group which may have a substituent for $R^{101}$ of formula (m-an-1).

Examples of $Rb^{204}$ to $Rb^{205}$ of formula (a6-1-2) include the same as those exemplified as the cyclic group which may have a substituent, a chain-like alkyl group which may have a substituent, or a chain-like alkenyl group which may have a substituent for $R^{104}$ to $R^{105}$ of formula (m-an-2). However, either Rb²⁰⁴ or Rb²⁰⁵ represents a chain-like alkenyl group which may have a substituent.

Examples of Rb²⁰⁶ to Rb²⁰⁸ of formula (a6-1-3) include the same as those exemplified as the cyclic group which may have a substituent, the chain-like alkyl group which may have a substituent, or the chain-like alkenyl group which may have a substituent for R¹⁰⁶ to R¹⁰⁸ of formula (m-an-3). However, at least one of Rb²⁰⁶ to Rb²⁰⁸ represents a chain-like alkenyl group which may have a substituent.

Rb¹⁰², Yb¹⁰¹, Vb¹⁰¹ to Vb¹⁰³, Lb¹⁰¹ to Lb¹⁰², and Lb¹⁰³ to Lb¹⁰⁵ are the same as the R¹⁰², Y¹⁰¹, V¹⁰¹ to V¹⁰³, L¹⁰¹ to L¹⁰², and L¹⁰³ to L¹⁰⁵ of formulae (m-an-1), (m-an-2), and (m-an-3), respectively.

In the case where either Rb²⁰¹ or Rb²⁰⁴ to Rb²⁰⁵ and at least one of Rb²⁰⁶ to Rb²⁰⁸ of formulae (a6-1-1) to (a6-1-3) represent a chain-like alkenyl group which does not have a substituent, (CH₃)C=CH— (a propenyl group) or H₂C=CH— (a vinyl group) is preferable. In the case where either Rb²⁰¹ or Rb²⁰⁴ to Rb²⁰⁵ and at least one of Rb²⁰⁶ to Rb²⁰⁸ of formulae (a6-1-1) to (a6-1-3) represent a chain-like alkenyl group which has a substituent, a divalent group is further preferably bonded to the vinyl group or the propenyl group. Preferred examples of the divalent group include an ester bond, an ether bond, an amide bond, a urethane bond, an alkylene group, a (poly)cycloalkylene group, a fluorinated alkylene group, an arylene group, —SO₂—O—, —SO₂—, or a combination thereof.

Hereinafter, preferred examples of the anion represented by formula (a6-1-1) will be shown. In the following respective formulae, R^α represents a hydrogen atom, a methyl group, or a trifluoromethyl group.

[Chemical formula 93]

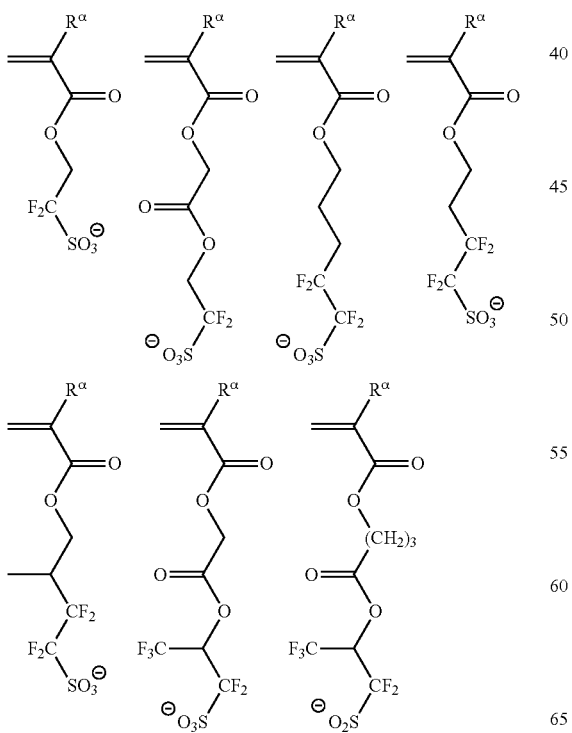

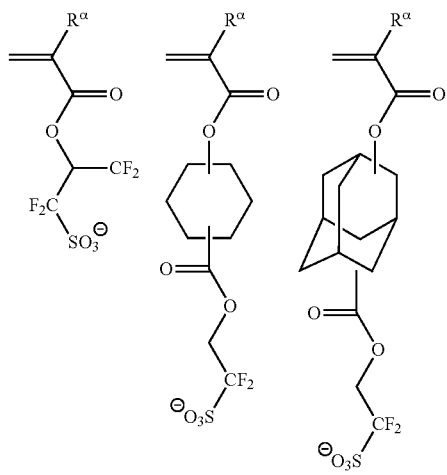

-continued

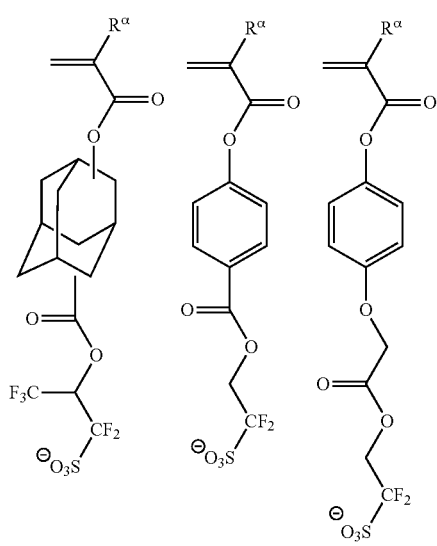

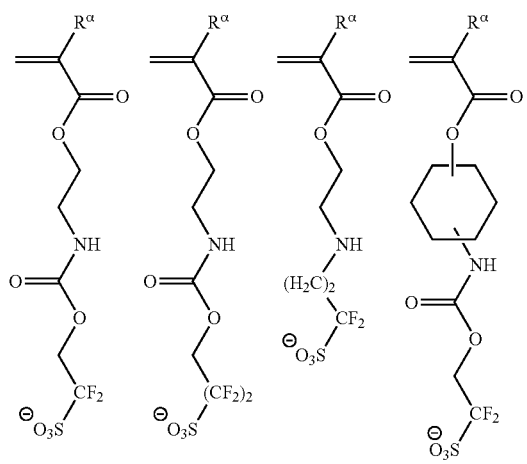

131
-continued
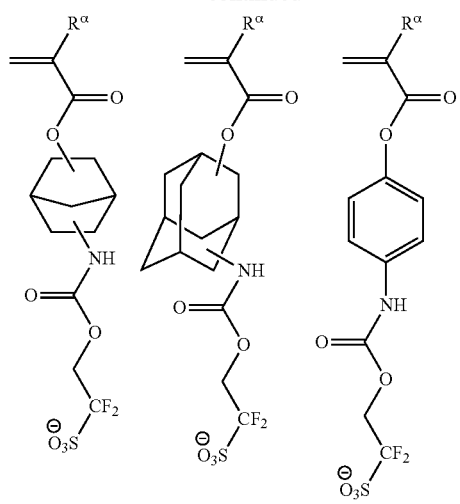
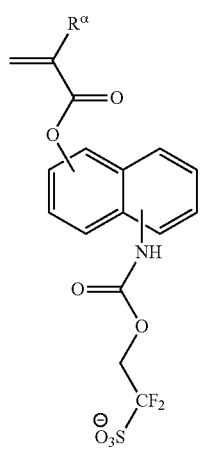
[Chemical formula 94]
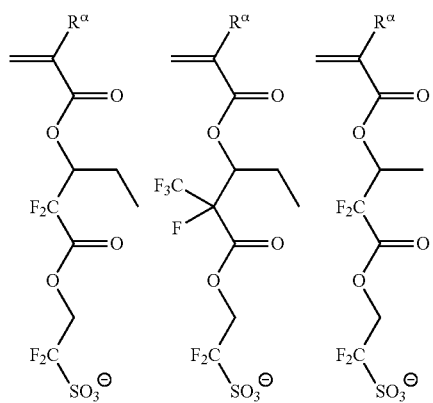
132
-continued
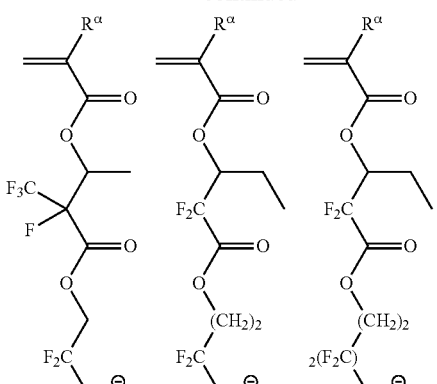
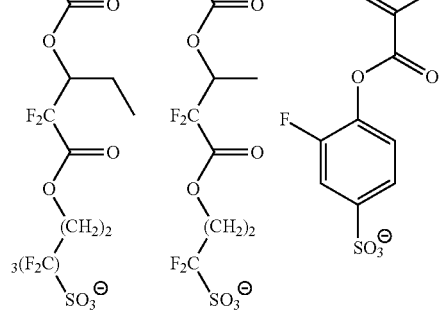
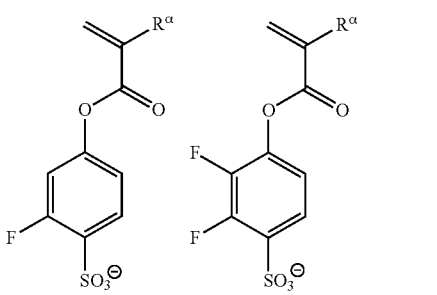
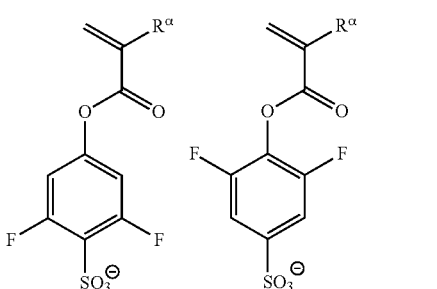
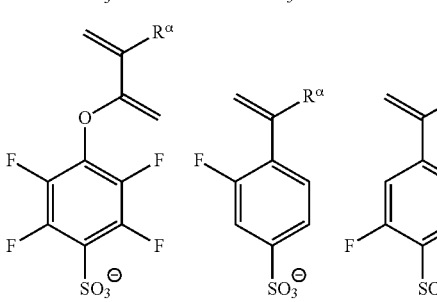

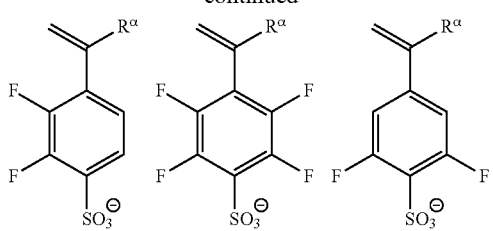

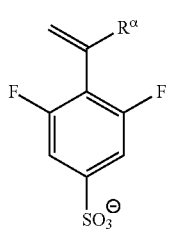

Hereinafter, preferred examples of the anion represented by formula (a6-1-2) will be shown. In the following formulae, $R^\alpha$ represents a hydrogen atom, a methyl group, or a trifluoromethyl group.

[Chemical formula 95]

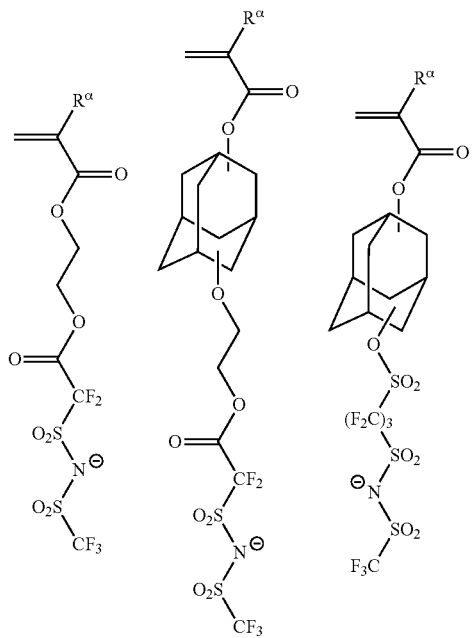

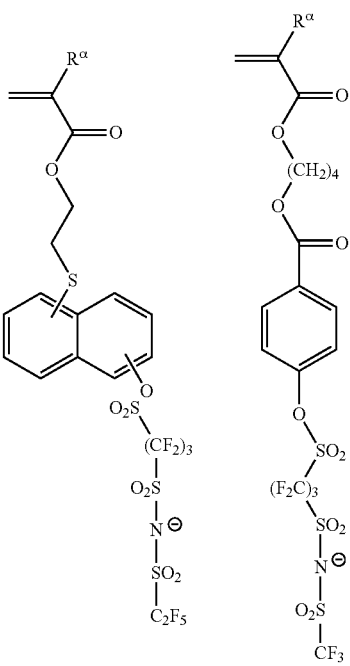

Hereinafter, preferred examples of the anion represented by formula (a6-1-3) will be shown. In the following formulae, $R^\alpha$ represents a hydrogen atom, a methyl group, or a trifluoromethyl group.

[Chemical formula 96]

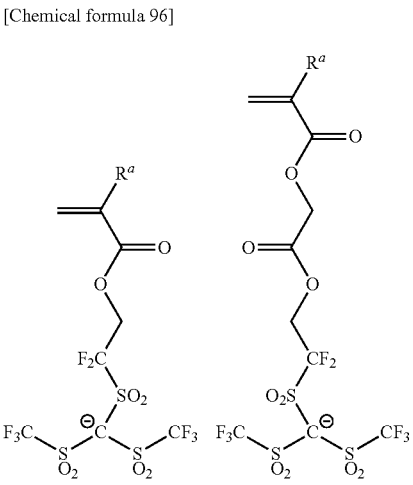

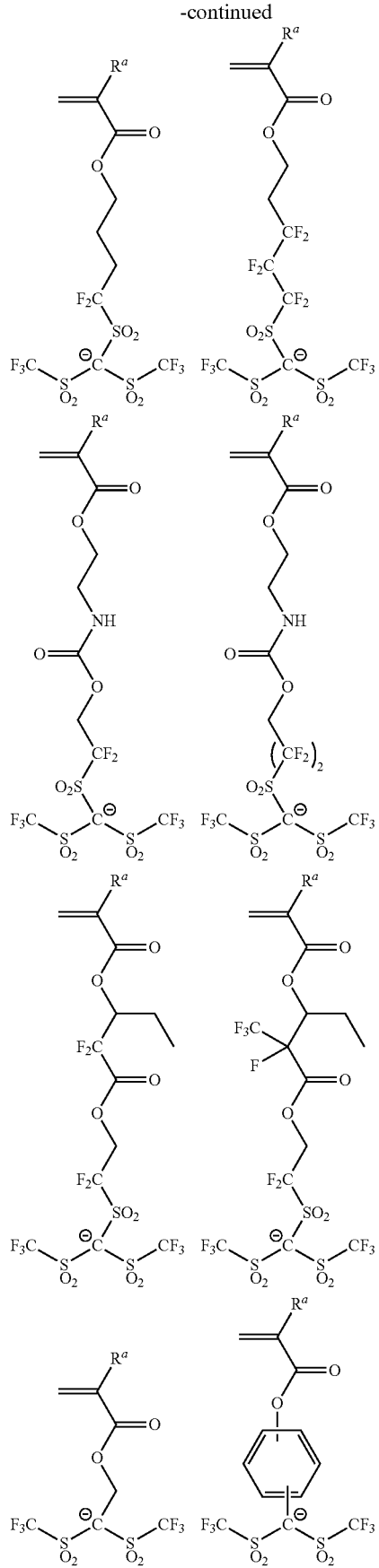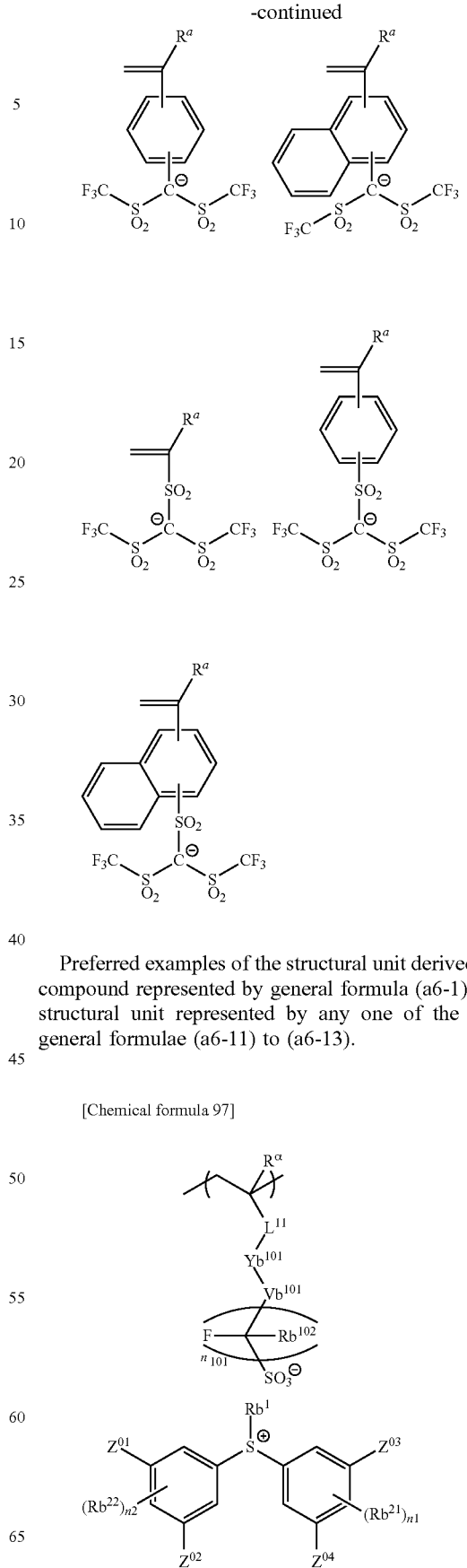
Preferred examples of the structural unit derived from the compound represented by general formula (a6-1) include a structural unit represented by any one of the following general formulae (a6-11) to (a6-13).
[Chemical formula 97]
(a6-11)
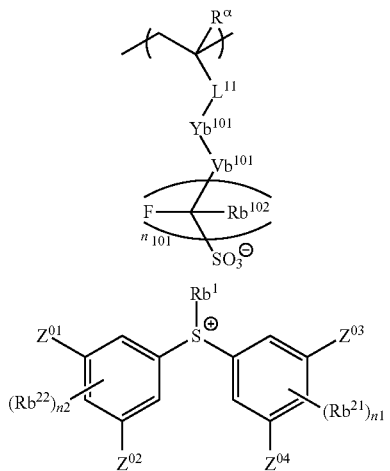

(a6-12)

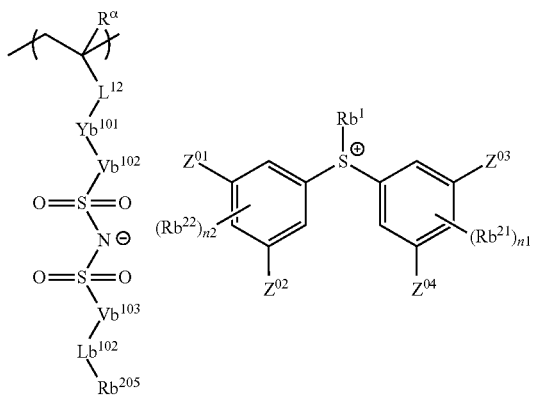

(a6-13)

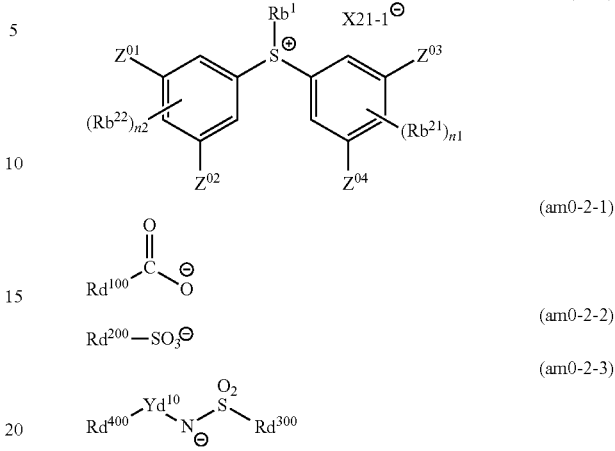

In the formulae, $R^\alpha$, $Z^{01}$ to $Z^{04}$, $Rb^{21}$, $Rb^{22}$, $Rb^1$, n1, n2, $Rb^{102}$, $Rb^{205}$, $Rb^{206}$, $Rb^{208}$, $Yb^{101}$, $Vb^{101}$ to $Vb^{103}$, $Lb^{101}$ to $Lb^{102}$, $Lb^{103}$ to $Lb^{105}$, and $n_{101}$ are the same as the above. $L^{11}$ to $L^{13}$ each independently represent a single bond or a divalent linking group.

Examples of the divalent linking group for $L^{11}$ to $L^{13}$ of respective formulae (a6-11) to (a6-13) include an ester bond, an alkylene group having 1 to 10 carbon atoms, a cycloalkylene group having 5 to 30 carbon atoms, a polycycloalkylene group having 5 to 30 carbon atoms, an arylene group having 6 to 10 carbon atoms, and a combination thereof.

In the component (A2), the structural unit derived from the compound represented by general formula (a6-1) may be one or two or more.

In the component (A2), the ratio of the structural unit derived from the compound represented by general formula (a6-1) is preferably 0.5 mol % to 30 mol %, more preferably 1 mol % to 20 mol %, and particularly preferably 1.5 mol % to 15 mol % with respect to all of the structural units configuring the component (A2).

If the ratio of the structural unit derived from the compound represented by general formula (a6-1) is set to the lower limit or more, it is easy to reduce roughness and obtain a satisfactory resist pattern shape. In addition, solvent solubility or sensitivity is improved. If the ratio is set to the upper limit or less, a good balance can be easily achieved with the other structural unit, and sensitivity at the time of forming a resist pattern can be increased.

Structural Unit (a6-2)

The resin component (A2) may have a structural unit (a6-2) derived from the compound represented by the following general formula (a6-2).

[Chemical formula 98]

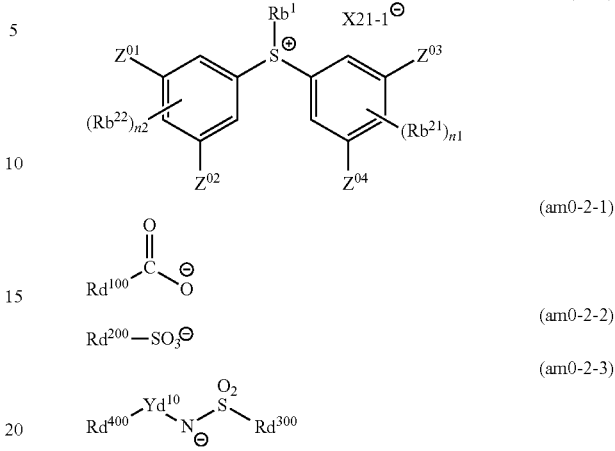

In formula (a6-2), $Z^{01}$ to $Z^{04}$ each independently represent a substituent having electron withdrawing properties, $Rb^{21}$ and $Rb^{22}$ each independently represent an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^1$ represents an aryl group which may have a substituent, an alkyl group which may have a substituent, or an alkenyl group which may have a substituent, and n1 and n2 each independently represent an integer of 0 to 3.

$X21\text{-}1^-$ represents an organic anion represented by any one of general formulae (am0-2-1) to (am0-2-3). In formula (am0-2-1), $Rd^{100}$ represents a chain-like alkenyl group which may have a substituent. In formula (am0-2-2), $Rd^{200}$ represents a chain-like alkenyl group which may have a substituent. However, a fluorine atom is not bonded to a carbon atom adjacent to the S atom in $Rd^{200}$. In formula (am0-2-3), $Rd^{300}$ to $Rd^{400}$ each independently represent a cyclic group which may have a substituent, a chain-like alkyl group which may have a substituent, or a chain-like alkenyl group which may have a substituent (however, at least one of $Rd^{300}$ to $Rd^{400}$ represents a chain-like alkenyl group which may have a substituent). $Yd^{10}$ represents a single bond or a divalent linking group.

Structural Unit Derived from the Compound Represented by General Formula (a6-2)

The description for $Z^{01}$ to $Z^{04}$, $Rb^{21}$, $Rb^{22}$, $Rb^1$, and n1 and n2 of general formula (a6-2) is the same as the description for $Z^{01}$ to $Z^{04}$, $Rb^{21}$, $Rb^{22}$, $Rb^1$, and n1 and n2 of formula (m1) shown above, respectively.

In formula (am0-2-1), examples of $Rd^{100}$ include the same group as the chain-like alkenyl group which may have a substituent for $Rd^1$ of formula (d1-1).

In formula (am0-2-2), examples of $Rd^{200}$ include the same group as the chain-like alkenyl group which may have a substituent for $Rd^2$ of formula (d1-2).

In formula (am0-2-3), examples of $Rd^{300}$ to $Rd^{400}$ include the same as those exemplified as the cyclic group which may have a substituent, the chain-like alkyl group which may have a substituent, or the chain-like alkenyl group which may have a substituent for $Rd^3$ to $Rd^4$ of formula (d1-3). However, at least one of $Rd^{300}$ to $Rd^{400}$ represents a chain-like alkenyl group which may have a substituent. $Yd^{10}$ of formula (am0-2-3) is the same as the single bond or the divalent linking group for $Yd^1$ of formula (d1-3).

In the case where at least one of $Rd^{100}$, $Rd^{200}$, and $Rd^{300}$ to $Rd^{400}$ of formulae (am0-2-1) to (am0-2-3) is a chain-like alkenyl group which does not have a substituent, $(CH_3)C=CH-$ (a propenyl group) or $H_2C=CH-$ (a vinyl group) is preferable. In the case where at least one of $Rd^{100}$, $Rd^{200}$, and $Rd^{300}$ to $Rd^{400}$ of formulae (am0-2-1) to (am0-2-3) is a chain-like alkenyl group which has a substituent, a divalent group is further preferably bonded to the vinyl group or the propenyl group. Preferred examples of the divalent group include an ester bond, an ether bond, an amide bond, a urethane bond, an alkylene group, a (poly)cycloalkylene group, an arylene group, or a combination thereof.

Hereinafter, preferred examples of the anion represented by formula (am0-2-1) will be shown. In the following respective formulae, $R^\alpha$ represents a hydrogen atom, a methyl group, or a trifluoromethyl group. m represents an integer of 0 to 3.

[Chemical formula 99]

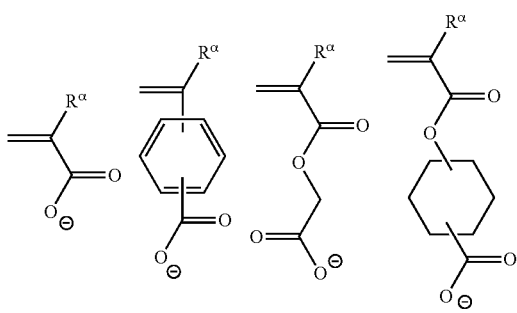

Hereinafter, preferred examples of the anion represented by formula (am0-2-2) will be shown. In the following respective formulae, $R^\alpha$ represents a hydrogen atom, a methyl group, or a trifluoromethyl group.

[Chemical formula 100]

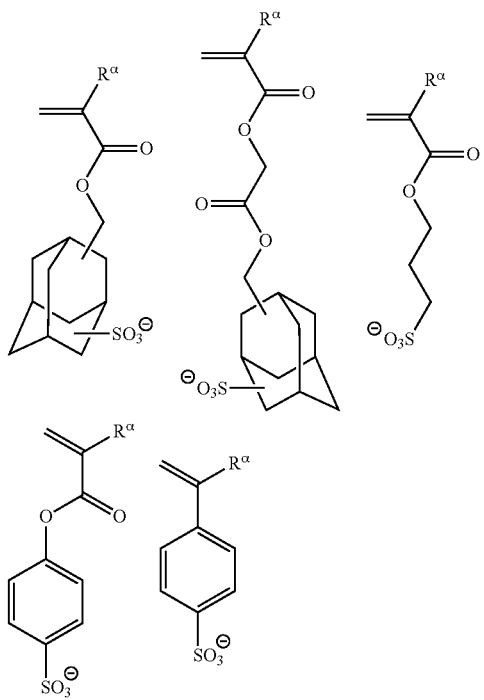

Hereinafter, preferred examples of the anion represented by formula (am0-2-3) will be shown. In the following respective formulae, $R^\alpha$ represents a hydrogen atom, a methyl group, or a trifluoromethyl group.

[Chemical formula 101]

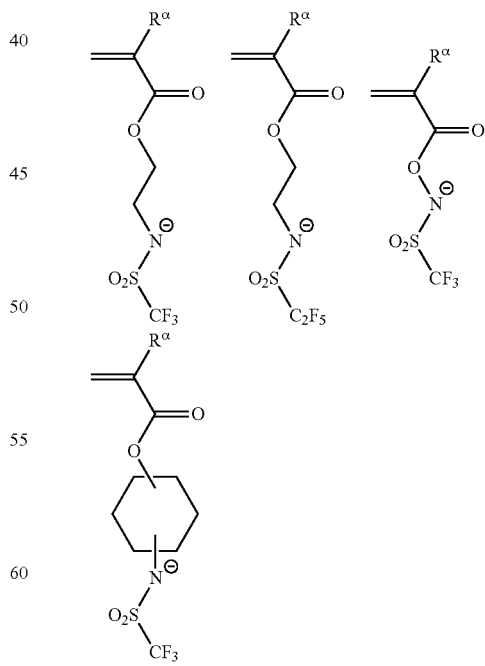

Preferred examples of the structural unit derived from the compound represented by general formula (a6-2) include a structural unit represented by any one of the following general formulae (am0-21) to (am0-23).

[Chemical formula 102]

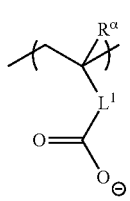
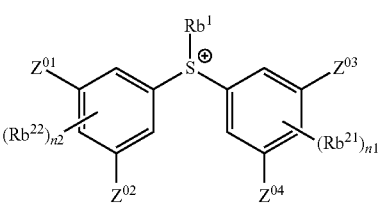
(am0-21)

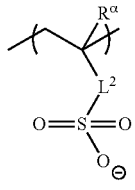
(am0-22)

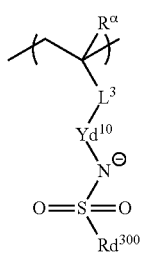
(am0-23)

In the formulae, $R^\alpha$, $Z^{01}$ to $Z^{04}$, $Rb^{21}$, $Rb^{22}$, $Rb^1$, n1, n2, $Yd^{10}$, and $Rd^{300}$ are the same as the above. $L^1$ to $L^3$ each independently represent a single bond or a divalent linking group.

Examples of the divalent linking group for $L^1$ to $L^3$ of respective formulae (am0-21) to (am0-23) include an ester bond, an alkylene group having 1 to 10 carbon atoms, a cycloalkylene group having 5 to 30 carbon atoms, a polycycloalkylene group having 5 to 30 carbon atoms, an arylene group having 6 to 10 carbon atoms, or a combination thereof.

In the component (A2), the type of the structural unit derived from the compound represented by general formula (a6-2) may be one or two or more.

In the component (A2), the ratio of the structural unit derived from the compound represented by general formula (a6-2) is preferably 0.5 mol % to 30 mol %, more preferably 1 mol % to 20 mol %, and particularly preferably 1.5 mol % to 15 mol % with respect to total structural units configuring the component (A2).

If the ratio of the structural unit derived from the compound (a6-2) is set to the lower limit or more, it is easy to reduce roughness and obtain a satisfactory resist pattern shape. In addition, solvent solubility or sensitivity is improved. If the ratio is set to the upper limit or less, a good balance can be easily achieved with the other structural unit, and sensitivity at the time of forming a resist pattern can be increased.

As the component (A2), a polymeric compound having the aforementioned structural unit (a1) is further preferably used, in addition to the structural unit (a6).

In addition, the component (A2) may further have the aforementioned structural unit (a10), the structural unit (a12), or other structural units (a structural unit (a2), or the like), in addition to the structural unit (a6) and the structural unit (a1).

The component (A2) is a copolymer having the structural unit (a6), and the copolymer is preferably
a copolymer having (a6), (a1), and (a10),
a copolymer having (a6), (a1), and (a12),
a copolymer having (a6), (a1), and (a9),
a copolymer having (a6), (a10), and (a12), or
a copolymer having (a6), (a1), (a2), and (a10).

The mass average molecular weight (Mw) (in terms of polystyrene by means of Gel Permeation Chromatography) of the component (A2) is not particularly limited, and the mass average molecular weight is preferably 1,000 to 50,000, more preferably 1,500 to 30,000, and most preferably 2,000 to 20,000. If the mass average molecular weight is equal to or less than the upper limit of the aforementioned range, solubility in a resist solvent enough to be used as a resist is obtained, and if the mass average molecular weight is equal to or more than the lower limit of the aforementioned range, dry etching resistance or a resist pattern cross-sectional shape is satisfactory.

In addition, the molecular weight dispersivity (Mw/Mn) of the component (A2) is not particularly limited, and preferably 1.0 to 5.0, more preferably 1.0 to 3.0, and most preferably 1.2 to 2.5.

Other Embodiments

The positive-type resist composition of the present invention may be a positive-type resist composition which further includes, for example, a nitrogen-containing compound component as the photo-reactive quencher, in addition to the first and second embodiments of the first aspect and the second aspect.

Nitrogen-containing Compound Component

The nitrogen-containing compound component acts as the acid diffusion control agent and is not particularly limited as long as the compound does not correspond to the components (D1) to (D2). The nitrogen-containing compound component may be arbitrarily used from the well-known compounds. Among these, aliphatic amine, in particular, secondary aliphatic amine or tertiary aliphatic amine is preferable.

The aliphatic amine is amine having at least one aliphatic group and the aliphatic group preferably has 1 to 12 carbon atoms.

Examples of the aliphatic amine include an amine in which at least one hydrogen atom of ammonia $NH_3$ is substituted with an alkyl group having equal to or less than 12 carbon atoms or a hydroxyalkyl group (alkylamine or alkyl alcohol amine), and a cyclic amine.

Examples of the alkylamine and alkyl alcohol amine include monoalkylamine such as n-hexylamine, n-heptylamine, n-octylamine, n-nonylamine, and n-decylamine; dialkylamine such as diethylamine, di-n-propylamine, di-n-heptylamine, di-n-octylamine, and dicyclohexylamine; trialkylamine such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, and tri-n-dodecylamine; and alkyl alcohol amine such as diethanolamine, triethanolamine, diisopropanolamine, triisopropanolamine, di-n-octanolamine, and tri-n-octanolamine. Among these, trialkylamine having 5 to 10 carbon atoms is still more preferable and tri-n-pentylamine or tri-n-octylamine is particularly preferable.

Examples of the cyclic amine include a heterocyclic compound including a nitrogen atom as a hetero atom. The heterocyclic compound may be monocyclic (aliphatic monocyclic amine) or polycyclic (aliphatic polycyclic amine).

Examples of the aliphatic monocyclic amine include piperidine, piperadine and the like.

The aliphatic polycyclic amine preferably has 6 to 10 carbon atoms, and examples thereof include 1,5-diazabicyclo[4.3.0]-5-nonene, 1,8-diazabicyclo[5.4.0]-7-undecene, hexamethylene tetramine, and 1,4-diazabicyclo[2.2.2]octane.

Other examples of the aliphatic amine include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, and triethanolamine triacetate, and triethanolamine triacetate is preferable.

In addition, aromatic amine may be used as the nitrogen-containing compound component.

Examples of the aromatic amine include aniline, pyridine, 4-dimethylaminopyridine, pyrrole, indole, pyrazole, imidazole, or a derivative thereof, diphenylamine, triphenylamine, tribenzylamine, 2,6-diisopropylaniline, and N-tert-butoxycarbonylpyrrolidine.

The nitrogen-containing compound component may be used alone or two or more thereof may be used in combination.

The nitrogen-containing compound component is commonly used within a range of 0.01 parts by mass to 5.0 parts by mass with respect to 100 parts by mass of the component (A). If the nitrogen-containing compound component is used in the aforementioned range, the shape of the resist pattern and the stability with a lapse of time after resist coating and before exposure are improved.

One type of the nitrogen-containing compound component may be used alone, or two or more types thereof may be used in combination.

In the case where the resist composition of the present invention contains the nitrogen-containing compound component, the content of the nitrogen-containing compound component is preferably 0.1 parts by mass to 15 parts by mass, more preferably 0.3 parts by mass to 12 parts by mass, and still more preferably 0.5 parts by mass to 12 parts by mass with respect to 100 parts by mass of the component (A). If the content of the nitrogen-containing compound component is equal to or more than the lower limit of the aforementioned range, when the component is used for the resist composition, the lithography properties such as LWR are improved. In addition, a more excellent resist pattern shape can be obtained. If the content of the nitrogen-containing compound component is equal to or less than the upper limit of the aforementioned range, the sensitivity can be maintained satisfactorily and a throughput is excellent.

Method for Forming a Resist Pattern

The third aspect of the present invention is a method for forming a resist pattern which includes forming a resist film using the positive-type resist composition according to the first or second aspect of the present invention; exposing the resist film; and developing the exposed resist film to form a resist pattern.

The method for forming a resist pattern can be carried out, for example, as follows.

First, the aforementioned resist composition is applied to the support by a spinner and subjected to a baking treatment (post applied bake (PAB)), for example, at a temperature condition of 80° C. to 150° C. for 40 seconds to 120 seconds, and preferably 60 seconds to 90 seconds to form a resist film.

Next, after selective exposure of the resist film is carried out, either by exposure through a mask having a predetermined pattern formed thereon (mask pattern) using an exposure apparatus such as an ArF exposure apparatus, an electron beam lithography apparatus or an EUV exposure apparatus, or by patterning via direct irradiation with an electron beam without using a mask pattern, baking treatment (post exposure baking (PEB)) is carried out under a temperature condition of 80° C. to 150° C. for 40 seconds to 120 seconds, and preferably 60 seconds to 90 seconds.

Next, the resist film is subjected to a developing treatment.

The developing treatment is performed by using an alkali developing solution.

After the developing treatment, it is preferable to carry out a rinsing treatment. The rinsing treatment is preferably conducted using pure water in the case of an alkali developing process, and a rinsing solution containing an organic solvent in the case of a solvent developing process.

After the developing treatment or the rinsing treatment, drying is conducted. If desired, baking treatment (post bake) can be conducted following the developing treatment. In this manner, a resist pattern can be obtained.

The developing treatment of the present invention may be an alkali developing process or a solvent developing process.

Support

The support is not particularly limited, the well-known support can be used, and examples thereof include substrates for electronic components and such substrates having wiring patterns formed thereon. Examples thereof include a substrate made of metals such as silicon wafer, copper, chromium, iron and aluminium; and a glass substrate. Examples of the material of the wiring patterns include copper, aluminium, nickel, and gold.

Further, as the support, an inorganic and/or organic film may be provided on the substrate as described above. As the inorganic film, an inorganic antireflection film (inorganic BARC) can be exemplified. As the organic film, an organic antireflection film (organic BARC) and an organic film such as a lower-layer organic film used in a multilayer resist method can be exemplified.

Here, a multilayer resist method is a method in which at least one layer of an organic film (lower-layer organic film) and at least one layer of a resist film (upper-layer resist film) are provided on a substrate, and a resist pattern formed on the upper-layer resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film, and at least one intermediate layer (thin metal film or the like) provided between the upper-layer resist film and the lower-layer organic film is formed (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beams (EB), X-rays, and soft X-rays. The resist composition is effective to KrF excimer laser, ArF excimer laser, EB or EUV, and among these, more effective to EB or EVU.

The exposure method of the resist film can be either a general exposure (dry exposure) conducted in air or an inert gas such as nitrogen, or liquid immersion exposure (liquid immersion lithography).

In liquid immersion lithography, the region between the resist film and the lens at the lowermost point of the exposure apparatus is pre-filled with a solvent (liquid immersion medium) that has a larger refractive index than the refractive index of air, and the exposure (liquid immersion exposure) is conducted in this state.

The liquid immersion medium is preferably a solvent exhibiting a refractive index larger than the refractive index of air but smaller than the refractive index of the resist film to be exposed. The refractive index of the solvent is not particularly limited as long as the index satisfies the aforementioned range.

Examples of this liquid immersion medium which exhibits a refractive index that is larger than the refractive index of air but smaller than the refractive index of the resist film include water, fluorine-based inert liquids, silicon-based solvents and hydrocarbon-based solvents.

Examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point preferably in a range of 70° C. to 180° C. and more preferably 80° C. to 160° C. A fluorine-based inert liquid having a boiling point in the aforementioned range is preferable in that the removal of the liquid immersion medium after the exposure can be conducted by a simple method.

As a fluorine-based inert liquid, a perfluoroalkyl compound in which all of the hydrogen atoms of the alkyl group are substituted with a fluorine atom is particularly preferable. Examples of these perfluoroalkyl compounds include perfluoroalkylether compounds and perfluoroalkylamine compounds.

Specifically, one example of the perfluoroalkylether compound is perfluoro(2-butyl-tetrahydrofuran) (boiling point 102° C.), and an example of the perfluoroalkylamine compound is perfluorotributylamine (boiling point 174° C.).

As the liquid immersion medium, water is preferably used in terms of cost, safety, environment and versatility.

As the alkali developing solution, a 0.1 mass % to 10 mass % aqueous solution of tetramethylammonium hydroxide (TMAH) can be exemplified.

The developing treatment can be conducted by a conventional developing method. Examples thereof include a method in which the support is immersed in the developing solution for a predetermined time (a dip method), a method in which the developing solution is cast up on the surface of the support by surface tension and maintained for a predetermined time (a puddle method), a method in which the developing solution is sprayed onto the surface of the support (a spray method), and a method in which the developing solution is continuously ejected from a developing solution ejecting nozzle while scanning at a constant rate to apply the developing solution to the support while rotating the support at a constant rate (a dynamic dispense method).

The rinsing treatment using a rinsing liquid (washing treatment) can be conducted by a conventional rinsing method. Examples of the rinsing method include a method in which the rinsing liquid is continuously applied to the support while rotating the support at a constant rate (a rotational coating method), a method in which the support is immersed in the rinsing liquid for a predetermined time (a dip method), and a method in which the rinsing liquid is sprayed onto the surface of the support (a spray method).

Photo-reactive Quencher

The fourth aspect of the present invention is a photo-reactive quencher which includes a compound (m) represented by the following general formula (m0).

[Chemical formula 103]

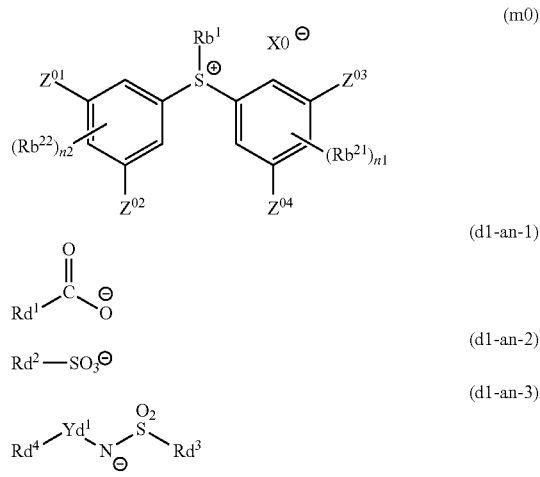

In general formula (m0), $Z^{01}$ to $Z^{04}$ each independently represent a substituent having electron withdrawing properties, $Rb^{21}$ and $Rb^{22}$ each independently represent an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^1$ represents an aryl group which may have a substituent, an alkyl group which may have a substituent, or an alkenyl group which may have a substituent, and n1 and n2 each independently represent an integer of 0 to 3.

$X0^-$ represents an organic anion represented by any one of general formulae (d1-an-1) to (d1-an-3).

In general formulae (d1-an-1) to (d1-an-3), $Rd^1$ to $Rd^4$ represent a cyclic group which may have a substituent, a chain-like alkyl group which may have a substituent, or a chain-like alkenyl group which may have a substituent.

However, two or more fluorine atoms are not bonded to a carbon atom adjacent to the S atom (shown in formula (d1-an-2)) in $Rd^2$. $Yd^1$ represents a single bond or a divalent linking group.

The description for the compound (m) included in the acid diffusion control agent of the present invention is the same as the description for the compound (m) according to the first aspect of the present invention.

Polymeric Compound

The fifth aspect of the present invention is a polymeric compound having a structural unit derived from the compound represented by the following general formula (a6-1)

[Chemical formula 104]

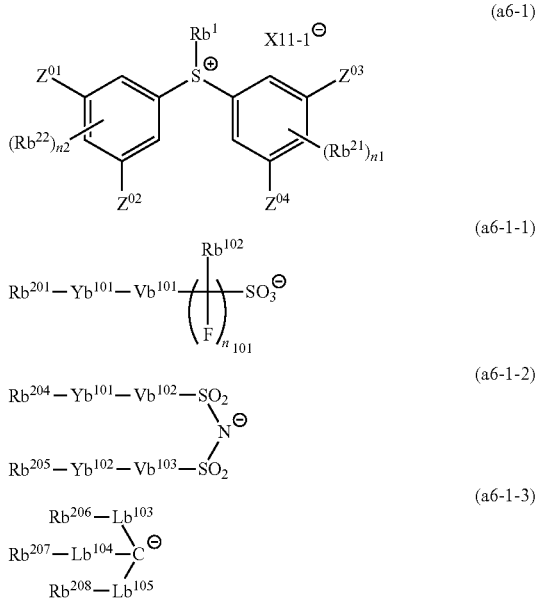

In general formula (a6-1), $Z^{01}$ to $Z^{04}$ each independently represent a substituent having electron withdrawing properties, $Rb^{21}$ and $Rb^{22}$ each independently represent an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^1$ represents an aryl group which may have a substituent, an alkyl group which may have a substituent, or an alkenyl group which may have a substituent, and n1 and n2 each independently represent an integer of 0 to 3.

$X11\text{-}1^-$ represents an organic anion represented by any one of general formulae (a6-1-1) to (a6-1-3). In formulae (a6-1-1) to (a6-1-3), $Rb^{201}$ represents a chain-like alkenyl group which may have a substituent, $Rb^{204}$ to $Rb^{205}$ each independently represent a cyclic group which may have a substituent, a chain-like alkyl group which may have a substituent, or a chain-like alkenyl group which may have a substituent, with the proviso that either $Rb^{204}$ or $Rb^{205}$ represents a chain-like alkenyl group which may have a substituent. $Rb^{206}$ to $Rb^{208}$ each independently represent a cyclic group which may have a substituent, a chain-like alkyl group which may have a substituent, or a chain-like alkenyl group which may have a substituent, with the proviso that any one of $Rb^{206}$ to $Rb^{208}$ represents a chain-like alkenyl group which may have a substituent. $Rb^{102}$ represents a fluorine atom or a fluorinated alkyl group having 1 to 5 carbon atoms. $Yb^{101}$ represents a single bond or a divalent linking group including an oxygen atom. $Vb^{101}$ to $Vb^{103}$ each independently represent a single bond, an alkylene group, a fluorinated alkylene group, an arylene group, or a fluorinated arylene group. $L^{101}$ to $L^{102}$ each independently represent a single bond or an oxygen atom. $Lb^{103}$ to $Lb^{105}$ each independently represent a single bond, —CO—, or —SO$_2$—. $n_{101}$ represents 0 or 1.

The description for the polymeric compound having a structural unit derived from the compound represented by general formula (a6-1) is the same as the description for the polymeric compound derived from the compound represented by general formula (a6-1) according to the first aspect of the present invention.

EXAMPLES

Hereinafter, the present invention will be described in detail using Examples and the present invention is not limited to the following Examples.

Production of Compound (m0)

Production Example 1

First Step

A solution obtained by diluting 28.6 g (0.48 moles) of thionyl chloride in 50 g of tetrahydrofuran was added dropwise to a tetrahydrofuran solution of 3,5-difluorophenyl magnesium bromide prepared by using 96.5 g (0.50 moles) of 1-bromo-3,5-difluorobenzene, 13.4 g (0.55 moles) of magnesium, and 400 g of tetrahydrofuran by means of a common method such that the temperature in the system does not exceed −5° C. After adding the solution dropwise, the reaction was continued for 1 hour at room temperature to complete the reaction.

The solution was added to 500 g of ion exchanged water such that the temperature does not exceed 15° C., and the resultant was stirred for 1 hour. After that, 300 g of ethyl acetate was put into thereto and the resultant was stirred for 1 hour. After the aqueous layer was removed, the resultant was washed with 300 g of ion exchanged water three times. A solvent in the organic layer was removed and the obtained brown residue was recrystallized by cyclohexane, thereby obtaining 26.0 g of bis(3,5-difluorophenyl)sulfoxide.

Hereinafter, bis(3,5-difluorophenyl)sulfoxide may be referred to as a "compound (m2)".

Second Step 6.86 g (0.025 moles) of the bis(3,5-difluorophenyl)sulfoxide synthesized in the first step was dissolved in 30 g of benzene, and 8.46 g (0.03 moles) of trifluoromethane sulfonic acid anhydride was added dropwise thereto such that the temperature in the system does not exceed −5° C.

After adding the solution dropwise, the reaction was continued for 1 hour at room temperature to complete the reaction. A supernant was removed, 50 g of ion exchanged water was added to the oily precipitate such that the temperature does not exceed 15° C., subsequently 75 g of tetrahydrofuran and 30 g of toluene were added thereto, and the resultant was stirred for 1 hour. An upper layer was removed and the remaining solution was washed with 30 g parts of toluene two times. After that, the solution was neutralized by sodium bicarbonate, 100 g of dichloromethane was added thereto to perform extraction, the aqueous layer was removed, and the organic layer was further washed with 50 g of ion exchanged water three times. When a solvent of the organic layer was removed and a crystal began being precipitated, 150 g of methyl-tertbutylether was added to the solution and a white crystal was precipitated. By filtering, fractionating, and drying this crystal under reduced pressure, 6.53 g (purity of 99.9% or more) of [bis(3,5-difluorophenyl)]phenylsulfonium trifluoromethane sulfonate was obtained, which is a target substance.

Hereinafter, [bis(3,5-difluorophenyl)]phenylsulfonium trifluoromethane sulfonate may be referred to as a "compound (m3)".

Third Step

The compound (m3) (10.0 g) obtained in the second step was dissolved in dichloromethane (200.0 g). After that, water (100.0 g) and the compound 2 (11.5 g) were added thereto and the resultant was stirred for 30 minutes. After that, then organic solvent phase was washed with water (100.0 g) three times by repeating liquid separation. The obtained organic solvent phase was added dropwise to methyl-tertiarybutylether (800.0 g) over 60 minutes, stirred for 30 minutes, and filtered. The obtained powder was dried at room temperature for 12 hours to obtain the following compound (m0)-1 (13.3 g).

[Chemical formula 105]

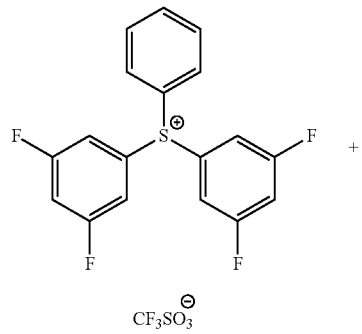

Compound (m3)

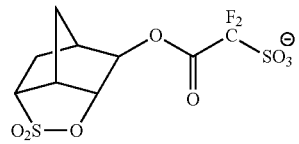

Compound 2

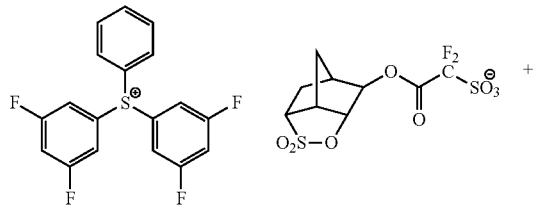

Compound (m0)-1

CF$_3$SO$_3^\ominus$ Na$^\oplus$

Production Example 2

First and Second Steps

The first step and the second step were carried out according to the same method as in the Production Example 1 except that 3,5-dimethyl-4-methoxybenzene was used instead of benzene in the second step of Production Example 1, thereby obtaining the following compound (m3-1).

Third Step

The compound (m3-1) (10.00 g) obtained according to the first step and the second step was dissolved in dichloromethane (200.0 g). After that, water (100.0 g) and the compound 2 (10.2 g) were added thereto and the resultant was stirred for 30 minutes. After that, the organic solvent phase was washed with water (100.0 g) three times by repeating liquid separation. The obtained organic solvent phase was added dropwise to methyl-tertiarybutylether (600.0 g) over 60 minutes, stirred for 30 minutes, and filtered. The obtained powder was dried at room temperature for 12 hours to obtain the following compound (m0)-5 (13.0 g).

[Chemical formula 106]

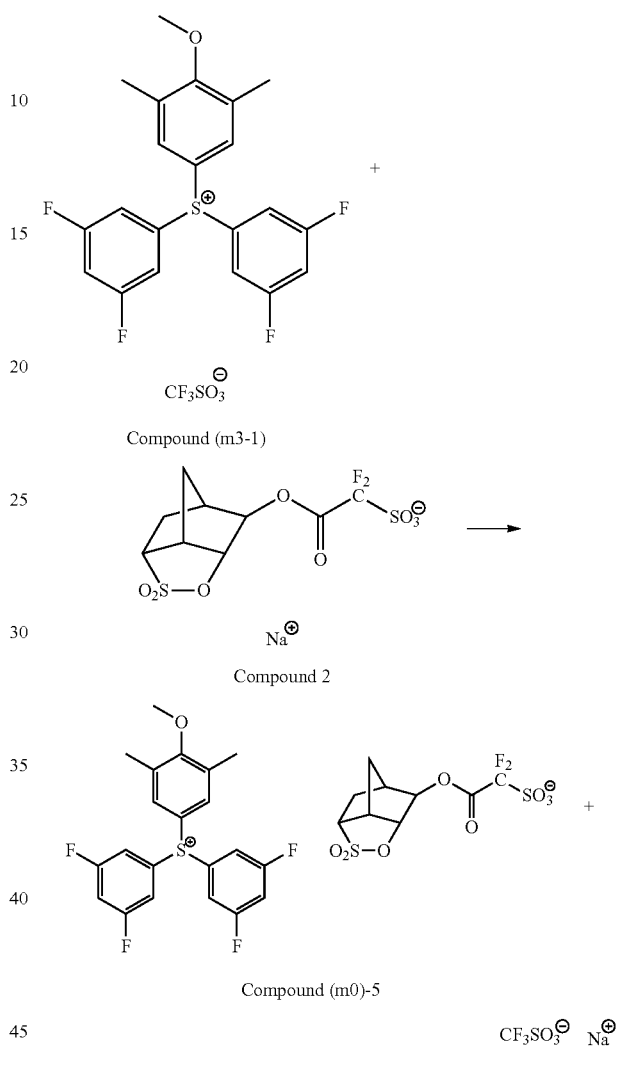

In a method similar to the aforementioned method, the following compounds (m0)-2 to (m0)-4, and (m0)-6 each were obtained. In the following, the compounds (m0)-1 to (m0)-6 are shown.

[Chemical formula 107]

(m0)-1

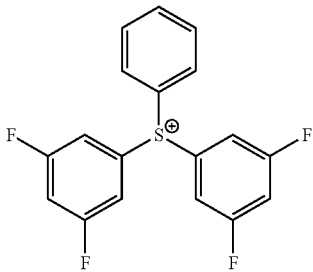

-continued

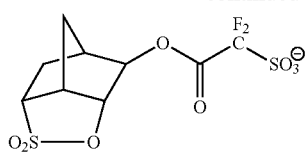

(m0)-2

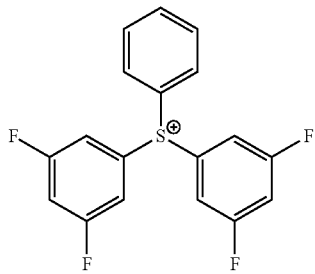

(m0)-3

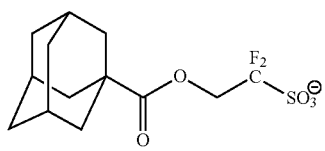

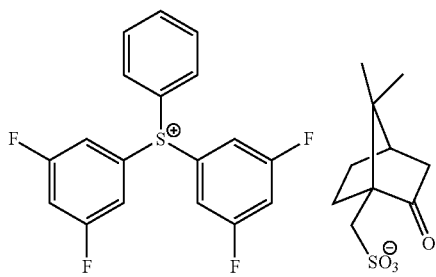

(m0)-4

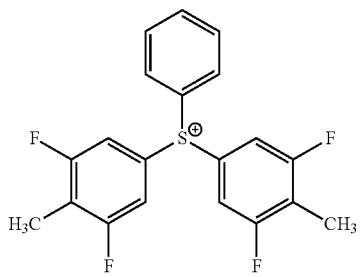

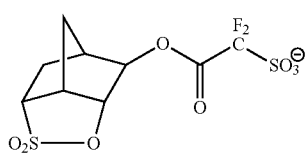

(m0)-5

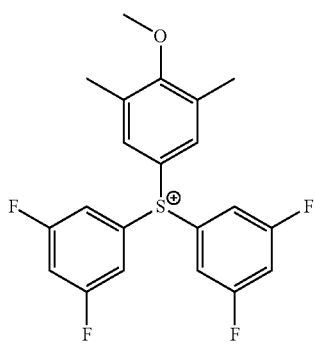

-continued

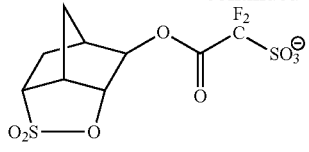

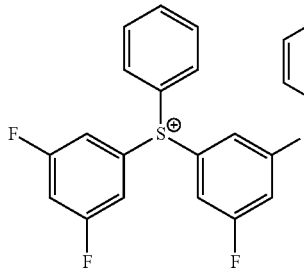

(m0)-6

Preparation of Positive-type Resist Composition

Positive-type resist compositions of Examples 1 to 12 and Comparative Examples 1 to 7 shown in the following Tables 1 and 2 were prepared, respectively.

TABLE 1

| | Component (A) | Component (B) | Component (D) | Component (S) |
|---|---|---|---|---|
| Example 1 | (A)-1 [100] | (B)-1 [14.5] | (D)-1 [3.0] | (S)-1 [6410] |
| Example 2 | (A)-1 [100] | (B)-2 [14.0] | (D)-1 [3.0] | (S)-1 [6380] |
| Example 3 | (A)-1 [100] | (B)-3 [12.0] | (D)-1 [3.0] | (S)-1 [6280] |
| Example 4 | (A)-1 [100] | (B)-4 [15.1] | (D)-1 [3.0] | (S)-1 [6440] |
| Example 5 | (A)-1 [100] | (B)-5 [14.5] | (D)-1 [3.0] | (S)-1 [6410] |
| Example 6 | (A)-2 [100] | (B)-1 [14.5] | (D)-1 [3.0] | (S)-1 [6410] |
| Example 7 | (A)-3 [100] | (B)-1 [14.5] | (D)-1 [3.0] | (S)-1 [6410] |
| Example 8 | (A)-4 [100] | (B)-1 [14.5] | (D)-1 [3.0] | (S)-1 [6410] |
| Example 9 | (A)-5 [100] | (B)-1 [14.5] | (D)-1 [3.0] | (S)-1 [6410] |
| Example 10 | (A)-6 [100] | (B)-1 [14.5] | (D)-1 [3.0] | (S)-1 [6410] |
| Example 11 | (A)-1 [100] | (B)-1 [14.5] | (D)-2 [3.5] | (S)-1 [6410] |
| Example 12 | (A)-1 [100] | (B)-10 [13.0] | (D)-2 [3.5] | (S)-1 [6410] |

TABLE 2

| | Component (A) | Component (B) | Component (D) | Component (S) |
|---|---|---|---|---|
| Comparative Example 1 | (A)-1 [100] | (B)-6 [13.4] | (D)-1 [3.0] | (S)-1 [6350] |
| Comparative Example 2 | (A)-1 [100] | (B)-7 [13.7] | (D)-1 [3.0] | (S)-1 [6370] |
| Comparative Example 3 | (A)-1 [100] | (B)-8 [15.9] | (D)-1 [3.0] | (S)-1 [6480] |
| Comparative Example 4 | (A)-1 [100] | (B)-9 [16.8] | (D)-1 [3.0] | (S)-1 [6540] |
| Comparative Example 5 | (A)-1 [100] | (B)-10 [13.0] | (D)-1 [3.0] | (S)-1 [6330] |
| Comparative Example 6 | (A)-1 [100] | (B)-10 [13.0] | (D)-3 [3.0] | (S)-1 [6330] |
| Comparative Example 7 | (A)-1 [100] | (B)-10 [13.0] | (D)-4 [3.0] | (S)-1 [6330] |

In Tables 1 and 2, each symbol means as follows. A numerical value in the brackets means a blending amount (parts by mass).

(A)-1 to (A)-6: the following polymeric compounds (A)-1 to (A)-6.

(B)-1 to (B)-10: the above compounds (m0)-1 to (m0)-5 and the following (B)-6 to (B)-10.

(D)-1, (D)-3, and (D)-4: the following compounds (D)-1, (D)-3, and (D)-4.

(D)-2: the above (m0)-6.

(S)-1: A mixed solvent of PGMEA/PGME=60/40 (mass ratio).

[Chemical formula 108]
(A)-1
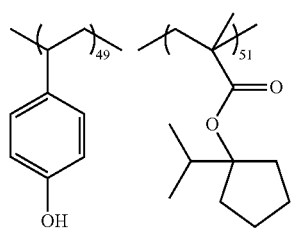
Mw = 7100
Mw/Mn = 1.64
(A)-2
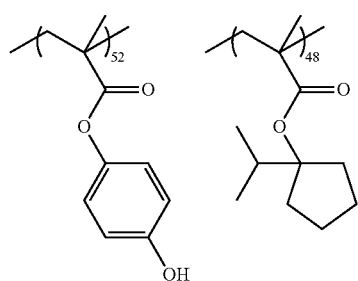
Mw = 7300
Mw/Mn = 1.68
(A)-3
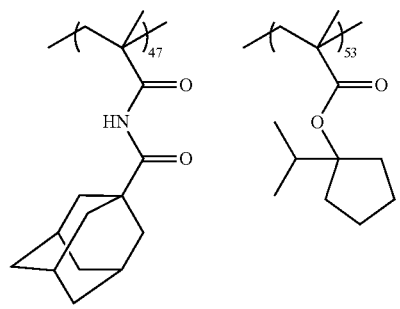
Mw = 6800
Mw/Mn = 1.69
(A)-4
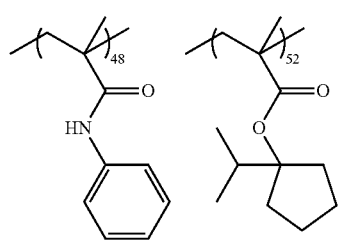
Mw = 7200
Mw/Mn = 1.71
-continued
[Chemical formula 109]
(A)-5
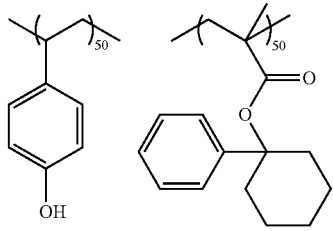
Mw = 7000
Mw/Mn = 1.66
(A)-6
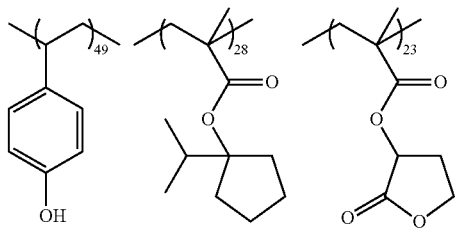
Mw = 6700
Mw/Mn = 1.63
[Chemical formula 110]
(B)-6
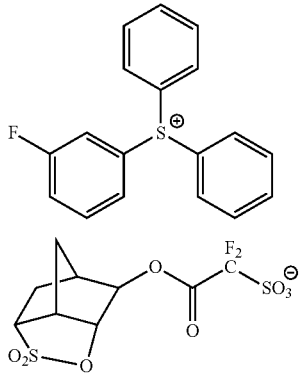
(B)-7
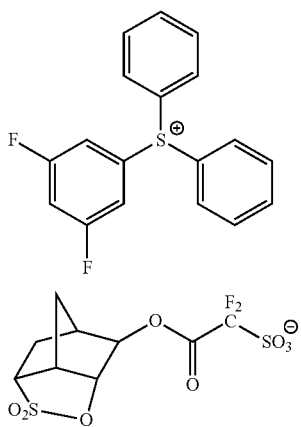

-continued (B)-8

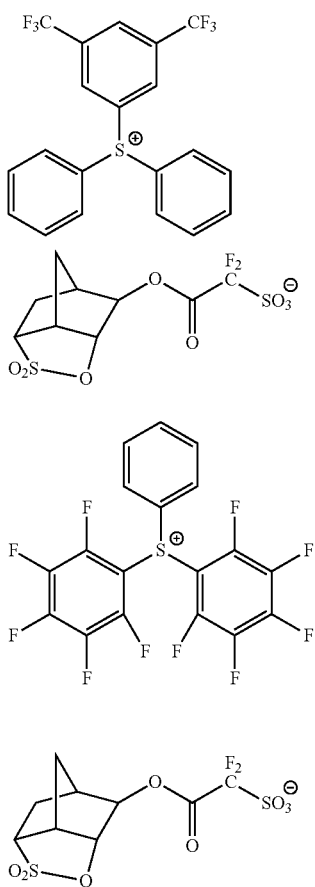

(B)-9

(B)-10

[Chemical formula 111]

(D)-1

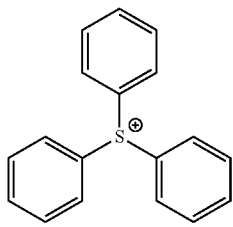

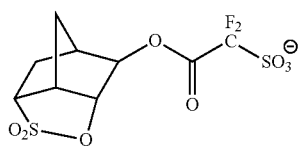

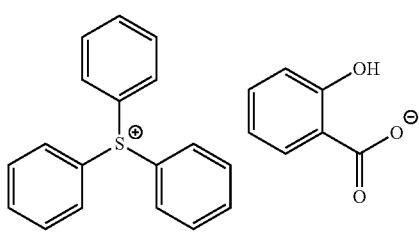

-continued

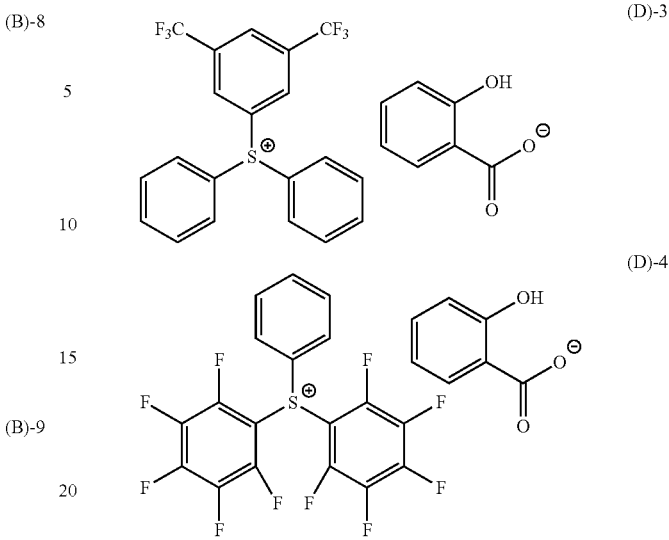

(D)-3

(D)-4

Formation of Positive-type Resist Pattern

Each of positive-type resist compositions of Examples 1 to 12 and Comparative Examples 1 to 7 was applied to an 8-inch silicon substrate subjected to a hexamethyl disilazane (HMDS) treatment by using a spinner, and the resulting substrate was prebaked (PAB) on a hot plate under a temperature condition of 100° C. for 60 seconds and dried, thereby forming a positive-type resist film having a film thickness of 50 nm.

Next, the positive-type resist film was patterned (exposed) using an electron beam lithography apparatus JEOL-JBX-9300FS (manufactured by JEOL Ltd.) at an accelerating voltage of 100 kV so as to obtain a 1:1 line and space pattern (hereinafter, "LS pattern") having a line width of 50 nm to 26 nm as a target size.

Next, alkali developing was conducted for 60 seconds using 2.38 mass % of tetramethylammonium hydroxide (TMAH) aqueous solution "NMD-3" (trade name, manufactured by TOKYO OHKA KOGYO CO., LTD.) at a temperature of 23° C.

After that, rinsing was conducted using pure water for 15 seconds and post exposure baking (PEB) was carried out at a temperature of 110° C. for 60 seconds.

As a result, a 1:1 LS pattern having a line width of 50 nm to 26 nm was formed.

Evaluation of Sensitivity (Eop)

An optimal exposure amount ($\mu C/cm^2$) in which an LS pattern having a target size is formed by the method for forming a positive-type resist pattern was obtained. The results are shown in Tables 3 and 4 as "sensitivity ($\mu C/cm^2$)".

Evaluation of Resolution

A limit resolution in the Eop, specifically, a minimum size of the pattern to be resolved without being collapsed, at the time of forming an LS pattern by gradually increasing the exposure amount from the optimal exposure amount Eop was determined using a scanning electron microscope (accelerating voltage of 800 V, trade name: S-9380, manufactured by Hitachi High-Technologies Corporation).

The results are shown in Tables 3 and 4 as "resolution (nm)".

Evaluation of LWR (Line Width Roughness)

With regard to the positive-type resist pattern formed above, 3σ was obtained, which indicates a scale of LWR.

The "3σ" indicates a value (3σ) (unit: nm) three times the standard deviation (σ) obtained from a measurement result, which was obtained by measuring a line position at 400 points of the line in the lengthwise direction using the scanning electron microscope (accelerating voltage of 800 V, trade name: S-9380, manufactured by Hitachi High-Technologies Corporation).

As the value of 3σ is smaller, roughness on the line side wall is lower, which means that a positive-type resist pattern having a uniform width can be obtained. The results are shown in Tables 3 and 4 as "LWR (nm)".

TABLE 3

| | Sensitivity (μC/cm$^2$) | Resolution (nm) | LWR (nm) |
|---|---|---|---|
| Example 1 | 65.4 | 32.0 | 5.4 |
| Example 2 | 65.8 | 32.5 | 5.6 |
| Example 3 | 65.5 | 32.2 | 5.5 |
| Example 4 | 66.0 | 32.3 | 5.7 |
| Example 5 | 65.9 | 32.4 | 5.6 |
| Example 6 | 65.6 | 32.3 | 5.6 |
| Example 7 | 65.7 | 32.5 | 5.8 |
| Example 8 | 65.6 | 32.4 | 5.7 |
| Example 9 | 64.9 | 31.0 | 5.1 |
| Example 10 | 65.7 | 32.3 | 5.6 |
| Example 11 | 66.2 | 31.7 | 5.3 |
| Example 12 | 66.1 | 32.1 | 5.5 |

TABLE 4

| | Sensitivity (μC/cm$^2$) | Resolution (nm) | LWR (nm) |
|---|---|---|---|
| Comparative Example 1 | 76.4 | 38.7 | 7.4 |
| Comparative Example 2 | 74.8 | 36.5 | 7.2 |
| Comparative Example 3 | 77.5 | 39.7 | 7.7 |
| Comparative Example 4 | 78.5 | 40.2 | 8.1 |
| Comparative Example 5 | 74.9 | 37.8 | 6.9 |
| Comparative Example 6 | 77.9 | 39.1 | 7.4 |
| Comparative Example 7 | 79.0 | 39.5 | 7.5 |

As shown in the above Tables 3 and 4, in the case where a resist pattern is formed by using the positive-type resist composition of the present invention, it is confirmed that a resist pattern which has more excellent sensitivity and further satisfactory resolution and reduced LWR compared to Comparative Examples is obtained.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A positive-type resist composition which generates an acid upon exposure and whose solubility in an alkali developing solution increases under the action of an acid, the composition comprising a base material component (A) whose solubility in an alkali developing solution increases under the action of an acid; and a compound (m) represented by the following general formula (m0):

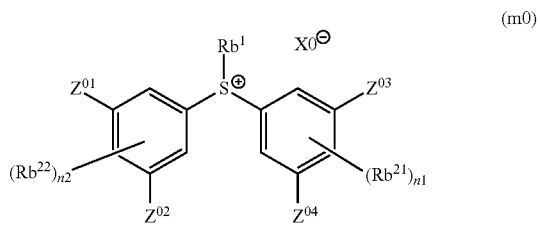

(m0)

wherein $Z^{01}$ to $Z^{04}$ each independently represents a substituent having electron withdrawing properties, $Rb^{21}$ and $Rb^{22}$ each independently represents an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^1$ represents an aryl group which may have a substituent, an alkyl group which may have a substituent, or an alkenyl group which may have a substituent, n1 and n2 each independently represents an integer of 0 to 3, and $X0^-$ represents an organic anion.

2. The positive-type resist composition according to claim 1, comprising:

a base material component (A) whose solubility in an alkali developing solution increases under the action of an acid;

an acid generator component (B1) which generates an acid upon exposure and includes the compound (m) represented by general formula (m0); and a photo-reactive quencher (D1).

3. The positive-type resist composition according to claim 1, comprising:

a base material component (A) whose solubility in an alkali developing solution increases under the action of an acid;

an acid generator component (B2) which generates an acid upon exposure; and a photo-reactive quencher (D2) which includes the compound (m) represented by general formula (m0).

4. The positive-type resist composition according to claim 1, wherein X0$^-$ in general formula (m0) represents an organic anion represented by any one of the following general formulae (d1-an-1) to (d1-an-3):

(d1-an-1)

(d1-an-2)

(d1-an-3)

wherein Rd¹ to Rd⁴ each independently represents a cyclic group which may have a substituent, a chain-like alkyl group which may have a substituent, or a chain-like alkenyl group which may have a substituent, with the proviso that two or more fluorine atoms are not bonded to a carbon atom adjacent to the S atom in Rd² of formula (d1-an-2), and Yd¹ is a single bond or a divalent linking group.

5. The positive-type resist composition according to claim 2, wherein X0⁻ in general formula (m0) represents an organic anion represented by any one of the following general formulae (d1-an-1) to (d1-an-3):

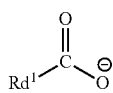 (d1-an-1)

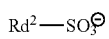 (d1-an-2)

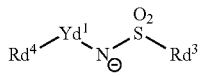 (d1-an-3)

wherein Rd¹ to Rd⁴ each independently represents a cyclic group which may have a substituent, a chain-like alkyl group which may have a substituent, or a chain-like alkenyl group which may have a substituent, with the proviso that two or more fluorine atoms are not bonded to a carbon atom adjacent to the S atom in Rd² of formula (d1-an-2), and Yd¹ is a single bond or a divalent linking group.

6. The positive-type resist composition according to claim 3, wherein X0⁻ in general formula (m0) represents an organic anion represented by any one of the following general formulae (d1-an-1) to (d1-an-3):

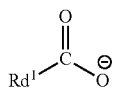 (d1-an-1)

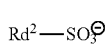 (d1-an-2)

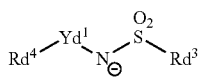 (d1-an-3)

wherein Rd¹ to Rd⁴ each independently represents a cyclic group which may have a substituent, a chain-like alkyl group which may have a substituent, or a chain-like alkenyl group which may have a substituent, with the proviso that two or more fluorine atoms are not bonded to a carbon atom adjacent to the S atom in Rd² of formula (d1-an-2), and Yd¹ is a single bond or a divalent linking group.

7. The positive-type resist composition according to claim 1, wherein the base material component (A) includes a resin component (A1) which has a structural unit (a9) represented by general formula (a9-1) or a structural unit (a10) including an aromatic hydrocarbon group having a hydroxy group:

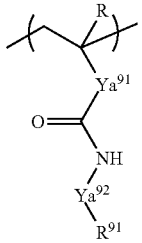 (a9-1)

wherein R represents a hydrogen atom, an alkyl group having 1 to 5 carbon atoms, or a halogenated alkyl group having 1 to 5 carbon atoms, $Ya^{91}$ represents a single bond or a divalent linking group, $R^{91}$ represents a hydrocarbon group which may have a substituent, and $Ya^{92}$ represents a divalent linking group.

8. The positive-type resist composition according to claim 2, wherein the base material component (A) includes a resin component (A1) which has a structural unit (a9) represented by general formula (a9-1) or a structural unit (a10) including an aromatic hydrocarbon group having a hydroxy group:

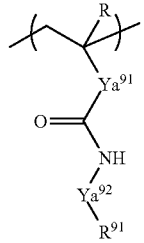 (a9-1)

wherein R represents a hydrogen atom, an alkyl group having 1 to 5 carbon atoms, or a halogenated alkyl group having 1 to 5 carbon atoms, $Ya^{91}$ represents a single bond or a divalent linking group, $R^{91}$ represents a hydrocarbon group which may have a substituent, and $Ya^{92}$ represents a divalent linking group.

9. The positive-type resist composition according to claim 3, wherein the base material component (A) includes a resin component (A1) which has a structural unit (a9) represented by general formula (a9-1) or a structural unit (a10) including an aromatic hydrocarbon group having a hydroxy group:

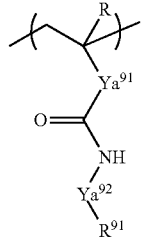 (a9-1)

wherein R represents a hydrogen atom, an alkyl group having 1 to 5 carbon atoms, or a halogenated alkyl group having 1 to 5 carbon atoms, $Ya^{91}$ represents a single bond or a divalent linking group, $R^{91}$ represents a hydrocarbon group which may have a substituent, and $Ya^{92}$ represents a divalent linking group.

10. The positive-type resist composition according to claim 4, wherein the base material component (A) includes a resin component (A1) which has a structural unit (a9) represented by general formula (a9-1) or a structural unit (a10) including an aromatic hydrocarbon group having a hydroxy group:

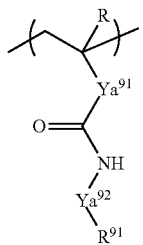

(a9-1)

wherein R represents a hydrogen atom, an alkyl group having 1 to 5 carbon atoms, or a halogenated alkyl group having 1 to 5 carbon atoms, $Ya^{91}$ represents a single bond or a divalent linking group, $R^{91}$ represents a hydrocarbon group which may have a substituent, and $Ya^{92}$ represents a divalent linking group.

11. The positive-type resist composition according to claim 5, wherein the base material component (A) includes a resin component (A1)which has a structural unit (a9) represented by general formula (a9-1) or a structural unit (a10) including an aromatic hydrocarbon group having a hydroxy group:

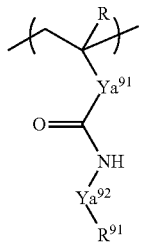

(a9-1)

wherein R represents a hydrogen atom, an alkyl group having 1 to 5 carbon atoms, or a halogenated alkyl group having 1 to 5 carbon atoms, $Ya^{91}$ represents a single bond or a divalent linking group, $R^{91}$ represents a hydrocarbon group which may have a substituent, and $Ya^{92}$ represents a divalent linking group.

12. The positive-type resist composition according to claim 6, wherein the base material component (A) includes a resin component (A1) which has a structural unit (a9) represented by general formula (a9-1) or a structural unit (a10) including an aromatic hydrocarbon group having a hydroxy group:

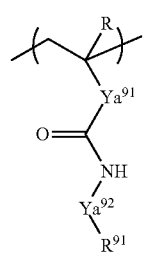

(a9-1)

wherein R represents a hydrogen atom, an alkyl group having 1 to 5 carbon atoms, or a halogenated alkyl group having 1 to 5 carbon atoms, $Ya^{91}$ represents a single bond or a divalent linking group, $R^{91}$ represents a hydrocarbon group which may have a substituent, and $Ya^{92}$ represents a divalent linking group.

13. A positive-type resist composition which generates an acid upon exposure and whose solubility in an alkali developing solution increases under the action of an acid, the composition comprising a base material component (A) whose solubility in an alkali developing solution increases under the action of an acid and which includes a resin component (A2) including a polymeric compound having a structural unit (a6) derived from a compound represented by the following general formula (a6-1):

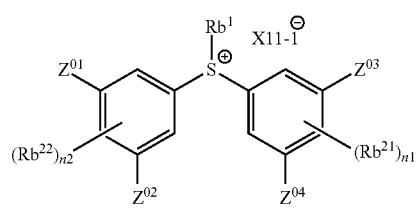

(a6-1)

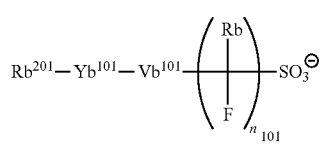

(a6-1-1)

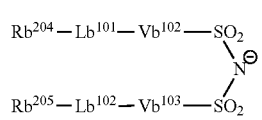

(a6-1-2)

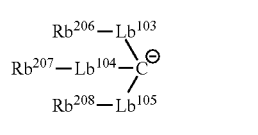

(a6-1-3)

wherein $Z^{01}$ to $Z^{04}$ each independently represents a substituent having electron withdrawing properties, $Rb^{21}$ and $Rb^{22}$ each independently represents an alkyl group, an alicyclic hydrocarbon group which may have a substituent, or a hydroxyl group, with the proviso that the substituent which $Rb^{21}$ and $Rb^{22}$ may have does not have a substituent having electron withdrawing properties, $Rb^1$ represents an aryl group which may have a substituent, an alkyl group which may have a substituent, or an alkenyl group which may have a substituent, n1 and n2 each independently represents an integer of 0 to 3, and X11-1⁻ represents an organic anion represented by any one of general formulae (a6-1-1) to (a6-1-3), and, in general formulae (a6-1-1) to (a6-1-3), $Rb^{201}$ represents a chain-like alkenyl group which may have a substituent, $Rb^{204}$ represents a cyclic group which may have a substituent, a chain-like alkyl group which may have a substituent, or a chain-like alkenyl group which may have a substituent, $Rb^{205}$ represents a chain-like alkenyl group which may have a substituent $Rb^{206}$ to $Rb^{208}$ each independently represents a cyclic group which may have a substituent, a chain-like alkyl group which may have a substituent, or a chain-like alkenyl group which may have a substituent, with the proviso that at least one of $Rb^{206}$ to $Rb^{208}$ represents a chain-like alkenyl group which may have a substituent, $Rb^{102}$ represents a fluorine atom or a fluorinated alkyl group having 1 to 5 carbon atoms, $Yb^{101}$ represents a single bond, or a divalent linking group including an oxygen atom, $Vb^{101}$ to $Vb^{103}$ each independently represents a single bond, an alkylene group, a fluorinated alkylene group, an arylene group, or a fluorinated arylene group, $Lb^{101}$ and $Lb^{102}$ each independently represents a single bond or an oxygen atom, $Lb^{103}$ to $Lb^{105}$ each independently represents a single bond, —CO—, or —SO$_2$—, and $n_{101}$ is 0 or 1.

14. A method for forming a resist pattern, comprising:
forming a resist film using the positive-type resist composition according to any one of claims 1 to 13 on a support;
exposing the resist film; and
developing the exposed resist film to form a resist pattern.

15. A photo-reactive quencher comprising
a compound (md) represented by the following general formula (m0-d):

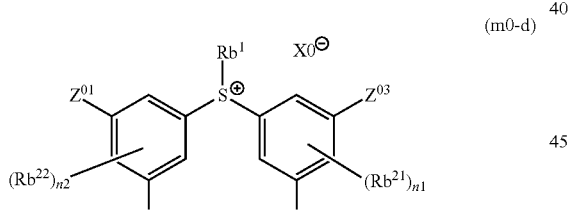

(m0-d)

(d1-an-1)

(d1-an-2)

(d1-an-3)

$Z^{01}$ to $Z^{04}$ each independently represents a substituent having electron withdrawing properties, $Rb^{21}$ and $Rb^{22}$ each independently represents an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^1$ represents an aryl group which may have a substituent, an alkyl group which may have a substituent, or an alkenyl group which may have a substituent, n1 and n2 each independently represents an integer of 0 to 3, and X0⁻ represents an organic anion represented by any one of general formulae (d1-an-1) to (d1-an-3), in general formulae (d1-an-1) to (d1-an-3), $Rd^1$ to $Rd^4$ represents a cyclic group which may have a substituent, a chain-like alkyl group which may have a substituent, or a chain-like alkenyl group which may have a substituent, with the proviso that two or more fluorine atoms are not bonded to a carbon atom adjacent to the S atom in $Rd^2$ of formula (d1-an-2), and $Yd^1$ represents a single bond or a divalent linking group.

16. A polymeric compound comprising a structural unit derived from a compound represented by the following general formula (a6-1):

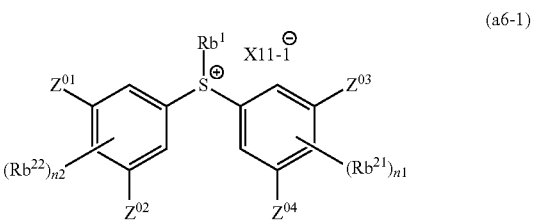

(a6-1)

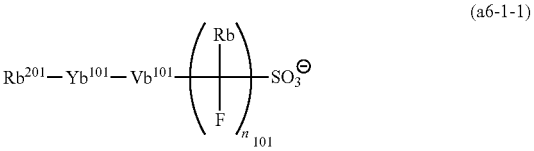

(a6-1-1)

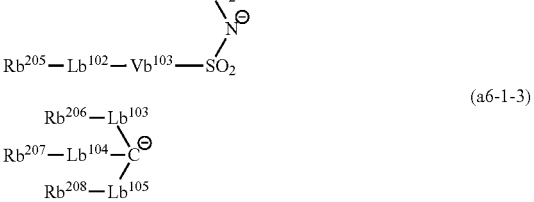

(a6-1-2)

$Rb^{206}$—$Lb^{103}$
$Rb^{207}$—$Lb^{104}$—$C^{⊖}$
$Rb^{208}$—$Lb^{105}$ (a6-1-3)

wherein $Z^{01}$ to $Z^{04}$ each independently represents a substituent having electron withdrawing properties, $Rb^{21}$ and $Rb^{22}$ each independently represent an alkyl group, an alicyclic hydrocarbon group which may have a substituent, or a hydroxyl group, with the proviso that the substituent which $Rb^{21}$ and $Rb^{22}$ may have does not include a substituent having electron withdrawing properties, $Rb^1$ represents an aryl group which may have a substituent, an alkyl group which may have a substituent, or an alkenyl group which may have a substituent, n1 and n2 each independently represents an integer of 0 to 3, and X11-1⁻ represents an organic anion represented by any one of general formulae (a6-1-1) to (a6-1-3), in general formulae (a6-1-1) to (a6-1-3), $Rb^{201}$ represents a chain-like alkenyl group which may have a substituent, $Rb^{204}$ represents a cyclic group which may have a substituent, a chain-like alkyl group which may have a substituent, or a chain-like alkenyl group which may have a substituent, $Rb^{205}$ represents a chain-like alkenyl group which may have a substituent, $Rb^{206}$ to $Rb^{208}$ each independently represents a cyclic group which may have a substituent, a chain-like alkyl group which may have a substituent, or a chain-like alkenyl group which may have a substituent, with the proviso that at least one of $Rb^{206}$ to $Rb^{208}$ represents a chain-like alkenyl group which may have a substituent, $Rb^{102}$ represents a fluorine atom, or a fluorinated alkyl group having 1 to 5 carbon atoms, $Yb^{101}$ represents a single bond, or a divalent linking group including an oxygen atom, $Vb^{101}$ to $Vb^{103}$ each independently represents a single bond, an alkylene group, a fluorinated alkylene group, an arylene group, or a fluorinated arylene group, $Lb^{101}$ and $Lb^{102}$ each independently represents a single bond or an oxygen atom, $Lb^{103}$ to $Lb^{105}$ each independently represents a single bond, —CO—, or —SO$_2$—, and $n_{101}$ is 0 or 1.

\* \* \* \* \*